US008541006B2

(12) United States Patent
Leid et al.

(10) Patent No.: US 8,541,006 B2
(45) Date of Patent: Sep. 24, 2013

(54) METHODS AND DEVICES FOR THE DETECTION OF BIOFILM

(75) Inventors: Jeffrey G. Leid, Flagstaff, AZ (US); Timothy L. Vail, Parks, AZ (US); Jennifer M. Kofonow, Philadelphia, PA (US); Mark E. Shirtliff, Ellicott City, MD (US); Rebecca A. Brady, Laurel, MD (US)

(73) Assignees: University of Maryland, Baltimore, Baltimore, MD (US); The Arizona Board of Regents, a body corporate acting for and on behalf of Northern Arizona University, Flagstaff, AZ (US)

( * ) Notice: Subject to any disclaimer, the term of this patent is extended or adjusted under 35 U.S.C. 154(b) by 243 days.

(21) Appl. No.: 12/671,398

(22) PCT Filed: Jul. 30, 2008

(86) PCT No.: PCT/US2008/071633
§ 371 (c)(1),
(2), (4) Date: Mar. 12, 2010

(87) PCT Pub. No.: WO2009/018369
PCT Pub. Date: Feb. 5, 2009

(65) Prior Publication Data
US 2010/0285496 A1    Nov. 11, 2010

Related U.S. Application Data

(60) Provisional application No. 60/952,786, filed on Jul. 30, 2007, provisional application No. 60/974,258, filed on Sep. 21, 2007.

(51) Int. Cl.
*A61K 39/085*    (2006.01)
*A61K 39/02*    (2006.01)
*A61K 39/00*    (2006.01)

(52) U.S. Cl.
USPC ....... 424/237.1; 424/9.1; 424/9.2; 424/130.1; 424/139.1; 424/163.1; 424/164.1; 424/185.1; 424/234.1

(58) Field of Classification Search
USPC ................ 424/9.1, 9.2, 130.1, 139.1, 163.1, 424/164.1, 184.1, 185.1, 234.1, 237.1
See application file for complete search history.

(56) References Cited

U.S. PATENT DOCUMENTS

| | | | |
|---|---|---|---|
| 6,583,275 B1 * | 6/2003 | Doucette-Stamm et al. | 536/23.1 |
| 7,220,401 B2 | 5/2007 | Lanza et al. | |
| 7,863,032 B2 * | 1/2011 | Berka et al. | 435/209 |
| 2004/0248856 A1 | 12/2004 | Lanza et al. | |
| 2006/0173362 A1 | 8/2006 | Toms et al. | |
| 2007/0059245 A1 | 3/2007 | Young et al. | |
| 2007/0154965 A1 | 7/2007 | Zhang et al. | |
| 2011/0171123 A1 | 7/2011 | Shirtliff et al. | |

FOREIGN PATENT DOCUMENTS

| | | |
|---|---|---|
| WO | 2008-096279 | 8/2008 |
| WO | 2008-105902 | 9/2008 |

OTHER PUBLICATIONS

Brady et al. Identification of *Staphylococcus aureus* proteins recognized by the antibody-mediated immune response to a bioflim infection. Infect. Immun. 74, 3415-3426 (2006). American Society for Microbiology, Washington, D.C.
Cosgrove et al. The impact of methicillin resistance in *Staphylococcus aureus* bacteremia on patient outcomes: mortality, length of stay, and hospital charges. Infect. Control Hosp. Epidemiol. 26, 166-174 (2005). The Univeristy of Chicago Press, Chicago, IL.
Costeron et al. The application of bioflim science to the study and control of chronic bacterial infections. J. Clin. Invest. 112, 1466-1477 (2003). American Society for Clinical Investigation, Ann Arbor, Michigan.
Jefferson et al. Use of confocal microscopy to analyze the rate of vancomycin penetration through *Staphylococcus aureus* biofilms. Antimicrob Agents Chemother. 49, 2467-2473 (2005). American Society for Microbiology, Washington, D.C.
Jesaitis et al., Compromised host defense on *Pseudomonas aeruginosa* biofilms: characterization of neutrophil and bioflim interactions. J. Immunol. 171, 4329-4339 (2003). The American Association of Immunologists, Bethesda, Maryland.
Kobayashi et al. Brief ultrasonication improves detection of biofilm-formative bacteria around a metal implant. Clin. Orthop. Relat. Res. 457, 210-213 (2007). The Association of Bone and Joint Surgeons, Rosemont, IL.
Lambert et al. Enzyme-linked immunosorbent assay for the detection of antibodies to exocellular proteins of *Staphylococcus aureus* in bone infection. FEMS Microbiology Letters. 100, 67-70 (1992). Wiley-Blackwell, United Kingdom., United Kingdom.
Leid et al. Immunology of Staphylococcal bioflim infections in the eye: new tools to study endophthalmitis. DNA Cell Biol. 21, 405-413 (2002). Mary Ann Liebert, Inc., New Rochelle, NY.
Leid et al. Human Leukocytes Adhere to, Penetrate, and Respond to *Staphylococcus aureus* Biofilms. Infect. Immun. 70, 6339-6345 (2002). American Society for Microbiology, Washington, D.C.
Leid et al. The exopolusaccharide alginate protects *Pseudomonas aeruginosa* bioflim bacteria from IFN-gamma-mediated macrophage killing. J. Immunol. 175, 7512-7518 (2005). The American Association of Immunologists, Bethesda, Maryland.
Mack et al. Bioflim formation in medical device-related infection. Int. J. Artif. Organs. 29, 343-359 (2006). European Society for Artificial Organs, Italy.
O'Toole et al. Biofilm Formation as Microbial Development. Annu. Rev. Microbiol. 54, 49-79 (2000). Annual Reviews, Palo Alto, CA.
Parsek et al. Bacterial Bioflims: An Emerging Link to Disease Pathogenesis. Annu. Rev. Microbiol. 57, 677-701 (2003). Annual Reviews, Palo Alto, CA.
Sanderson et al. Bacterial bioflims on the sinus mucosa of hnman subjects with chronic rhinosinusitis. Laryngoscope. 116, 1121-1126 (2006). Wiley-Blackwell, United Kingdom.

(Continued)

Primary Examiner — Rodney P. Swartz
(74) *Attorney, Agent, or Firm* — Nevrivy Patent Law Group P.L.L.C.

(57) ABSTRACT

The present invention provides methods and kits for biofilm detection.

20 Claims, 6 Drawing Sheets

(56) References Cited

OTHER PUBLICATIONS

Selan et al. Diagnosis of vascular graft infections with antibodies against staphylococcal slime antigens. Lancet. 359, 2166-2168 (2002). Elsevier Limited, The Netherlands.

Shirtliff et al. Molecular interactions in biofilms. Chem. Biol. 9, 859-871 (2002). Elsevier Limited, The Netherlands.

Trampuz et al. Diagnosis and treatment of infections associated with fracture-fixation devices. Injury. 37, S59-S66 (2006). Elsevier Limited, The Netherlands.

Tyski et al. Lipase versus teichoic acid and alpha-toxin as antigen in an enzyme immunoassay for serological diagnosis of *Staphylococcus aureus* infections. Eur. J. Clin. Microbiol. Infect. Dis. 10, 447-449 (1991), Springer, Germany.

Veeh et al. Detection of *Staphylococcus aureus* bioflim on tampons and menses components. J. Infect. Dis. 188, 519-530 (2003). Oxford Journals, United Kingdom.

Watkin et al. The serological diagnosis of staphylococcal infective endocarditis. J. Infect. 53, 301-307 (2006). Elsevier Limited, The Netherlands.

Ymele-Leki et al. Erosion from *Staphylococcus aureus* biofilms grown under physiologically relevant fluid shear forces yields bacterial cells with reduced avidity to collagen. Appl. Environ. Microbiol. 73, 1834-1841 (2007). American Society for Microbiology, Washington, D.C.

Suci et al. High Density Targeting of a Viral Multifunctional Nanoplatform to a Pathogenic, Biofilm-Forming Bacterium, Chemistry and Biology, 14, 387-398 (Apr. 2007). Elsevier Limited, The Netherlands.

Rafiq et al. Serological Detection of Gram-positive bacterial infection around prosthesis. Journal of Bone and Joint Surgery, 82-B, 1156-1161 (2000). British Editorial Society for Bone and Joint Surgery, United Kingdom.

NCBI submission YP_039889. Retrieved from the Internet Jul. 31, 2012: <http://www.ncbi.nlm.nih.gov/protein/YP_039889>.

Office Action from co-pending U.S. Appl. No. 13/061,142, mailed Jul. 18, 2012.

\* cited by examiner

A) ELISA (Ag01)

B) ELISA (Ag02)

C) ELISA (Ag03)

SEQUENCE LISTING

<160> NUMBER OF SEQ ID NOS: 53

<210> SEQ ID NO 1
<211> LENGTH: 261
<212> TYPE: PRT
<213> ORGANISM: Staphylococcus aureus

<400> SEQUENCE: 1

Met Met Gly Asn Ile Lys Ser Phe Ala Leu Tyr Ile Ser Ile Leu Leu
1               5                   10                  15

Leu Ile Val Val Val Ala Gly Cys Gly Lys Ser Asp Lys Thr Lys Glu
            20                  25                  30

Asp Ser Lys Glu Glu Gln Ile Lys Lys Ser Phe Ala Lys Thr Leu Asp
        35                  40                  45

Met Tyr Pro Ile Lys Asn Leu Glu Asp Leu Tyr Asp Lys Glu Gly Tyr
    50                  55                  60

Arg Asp Gly Glu Phe Lys Lys Gly Asp Lys Gly Thr Trp Thr Leu Leu
65                  70                  75                  80

Thr Ser Phe Ser Lys Ser Asn Lys Pro Asp Glu Ile Asp Asp Glu Gly
                85                  90                  95

Met Val Leu Tyr Leu Asn Arg Asn Thr Lys Lys Ala Thr Gly Tyr Tyr
            100                 105                 110

Phe Val Asn Lys Ile Tyr Asp Asp Ile Ser Lys Asn Gln Asn Glu Lys
        115                 120                 125

Lys Tyr Arg Val Glu Leu Lys Asn Asn Lys Ile Val Leu Leu Asp Asn
    130                 135                 140

Val Glu Asp Glu Lys Leu Lys Gln Lys Ile Glu Asn Phe Lys Phe Phe
145                 150                 155                 160

Ser Gln Tyr Ala Asp Phe Lys Asp Leu Lys Asn Tyr Gln Asp Gly Ser
                165                 170                 175

Ile Thr Thr Asn Glu Asn Ile Pro Ser Tyr Glu Ala Glu Tyr Lys Leu
            180                 185                 190

Asn Asn Ser Asp Glu Asn Val Lys Lys Leu Arg Asp Ile Tyr Pro Ile
        195                 200                 205

Thr Thr Lys Lys Ala Pro Ile Leu Lys Leu His Ile Asp Gly Asp Ile
    210                 215                 220

Lys Gly Ser Ser Val Gly Tyr Lys Lys Ile Glu Tyr Lys Phe Ser Lys
225                 230                 235                 240

Val Lys Asp Gln Glu Thr Thr Leu Arg Asp Tyr Leu Asn Phe Gly Pro
                245                 250                 255

Ser Asp Glu Asp Ser
            260

<210> SEQ ID NO 2
<211> LENGTH: 168
<212> TYPE: PRT
<213> ORGANISM: Staphylococcus aureus

<400> SEQUENCE: 2

Met Asn Thr Ile Lys Asn Thr Ile Tyr Thr Glu Ala Ile Phe Ser Lys
1               5                   10                  15

Asp Glu Lys His Arg Tyr Leu Leu Lys Lys Thr Trp Asp Glu Lys Lys
            20                  25                  30

Pro Ala Cys Thr Val Ile Thr Met Tyr Pro His Leu Asp Gly Val Leu
        35                  40                  45

-continued

Ser Leu Asp Leu Thr Thr Val Leu Ile Leu Asn Gln Leu Ala Asn Ser
    50                  55                  60

Glu Arg Tyr Gly Ala Val Tyr Leu Val Asn Leu Phe Ser Asn Ile Lys
 65                  70                  75                  80

Thr Pro Glu Asn Leu Lys His Ile Lys Glu Pro Tyr Asp Lys His Thr
                 85                  90                  95

Asp Ile His Leu Met Lys Ala Ile Ser Glu Ser Asp Thr Val Ile Leu
            100                 105                 110

Ala Tyr Gly Ala Tyr Ala Lys Arg Pro Val Val Glu Arg Val Glu
            115                 120                 125

Gln Val Met Glu Met Leu Lys Pro His Lys Lys Val Lys Lys Leu
130                 135                 140

Ile Asn Pro Ala Thr Asn Glu Ile Met His Pro Leu Asn Pro Lys Ala
145                 150                 155                 160

Arg Gln Lys Trp Thr Leu Lys Ala
                165

<210> SEQ ID NO 3
<211> LENGTH: 1257
<212> TYPE: PRT
<213> ORGANISM: Staphylococcus aureus

<400> SEQUENCE: 3

Met Ala Lys Lys Phe Asn Tyr Lys Leu Pro Ser Met Val Ala Leu Thr
 1               5                  10                  15

Leu Val Gly Ser Ala Val Thr Ala His Gln Val Gln Ala Ala Glu Thr
                20                  25                  30

Thr Gln Asp Gln Thr Thr Asn Lys Asn Val Leu Asp Ser Asn Lys Val
            35                  40                  45

Lys Ala Thr Thr Glu Gln Ala Lys Ala Glu Val Lys Asn Pro Thr Gln
 50                  55                  60

Asn Ile Ser Gly Thr Gln Val Tyr Gln Asp Pro Ala Ile Val Gln Pro
 65                  70                  75                  80

Lys Ala Ala Asn Lys Thr Gly Asn Ala Gln Val Asn Gln Lys Val Asp
                 85                  90                  95

Thr Thr Gln Val Asn Gly Asp Thr Arg Ala Thr Gln Ser Thr Thr Ser
            100                 105                 110

Asn Asn Ala Lys Pro Val Thr Lys Ser Thr Asn Thr Thr Ala Pro Lys
            115                 120                 125

Thr Asn Asn Asn Val Thr Ser Ala Gly Tyr Ser Leu Val Asp Asp Glu
130                 135                 140

Asp Asp Asn Ser Glu Asn Gln Ile Asn Pro Glu Leu Ile Lys Ser Ala
145                 150                 155                 160

Ala Lys Pro Ala Ala Leu Glu Thr Gln Tyr Lys Ala Ala Pro Lys
            165                 170                 175

Ala Thr Pro Val Ala Pro Lys Ala Lys Thr Glu Ala Thr Pro Lys Val
            180                 185                 190

Thr Thr Phe Ser Ala Ser Ala Gln Pro Arg Ser Ala Ala Ala Pro
            195                 200                 205

Lys Thr Ser Leu Pro Lys Tyr Lys Pro Gln Val Asn Ser Ser Ile Asn
210                 215                 220

Asp Tyr Ile Arg Lys Asn Asn Leu Lys Ala Pro Lys Ile Glu Glu Asp
225                 230                 235                 240

Tyr Thr Ser Tyr Phe Pro Lys Tyr Ala Tyr Arg Asn Gly Val Gly Arg
                245                 250                 255

-continued

Pro Glu Gly Ile Val His Asp Thr Ala Asn Asp Arg Ser Thr Ile
            260                 265                 270

Asn Gly Glu Ile Ser Tyr Met Lys Asn Asn Tyr Gln Asn Ala Phe Val
275                 280                 285

His Ala Phe Val Asp Gly Asp Arg Ile Ile Glu Thr Ala Pro Thr Asp
290                 295                 300

Tyr Leu Ser Trp Gly Val Gly Ala Val Gly Asn Pro Arg Phe Ile Asn
305                 310                 315                 320

Val Glu Ile Val His Thr His Asp Tyr Ala Ser Phe Ala Arg Ser Met
            325                 330                 335

Asn Asn Tyr Ala Asp Tyr Ala Ala Thr Gln Leu Gln Tyr Tyr Gly Leu
            340                 345                 350

Lys Pro Asp Ser Ala Glu Tyr Asp Gly Asn Gly Thr Val Trp Thr His
            355                 360                 365

Tyr Ala Val Ser Lys Tyr Leu Gly Gly Thr Asp His Ala Asp Pro His
            370                 375                 380

Gly Tyr Leu Arg Ser His Asn Tyr Ser Tyr Asp Gln Leu Tyr Asp Leu
385                 390                 395                 400

Ile Asn Glu Lys Tyr Leu Ile Lys Met Gly Lys Val Ala Pro Trp Gly
                405                 410                 415

Thr Gln Ser Thr Thr Thr Pro Thr Thr Pro Ser Lys Pro Ser Thr Pro
            420                 425                 430

Ser Lys Pro Ser Thr Pro Ser Thr Gly Lys Leu Thr Val Ala Ala Asn
            435                 440                 445

Asn Gly Val Ala Gln Ile Lys Pro Thr Asn Ser Gly Leu Tyr Thr Thr
450                 455                 460

Val Tyr Asp Lys Thr Gly Lys Ala Thr Asn Glu Val Gln Lys Thr Phe
465                 470                 475                 480

Ala Val Ser Lys Thr Ala Thr Leu Gly Asn Gln Lys Phe Tyr Leu Val
                485                 490                 495

Gln Asp Tyr Asn Ser Gly Asn Lys Phe Gly Trp Val Lys Glu Gly Asp
            500                 505                 510

Val Val Tyr Asn Thr Ala Lys Ser Pro Val Asn Val Asn Gln Ser Tyr
            515                 520                 525

Ser Ile Lys Pro Gly Thr Lys Leu Tyr Thr Val Pro Trp Gly Thr Ser
530                 535                 540

Lys Gln Val Ala Gly Ser Val Ser Gly Ser Gly Asn Gln Thr Phe Lys
545                 550                 555                 560

Ala Ser Lys Gln Gln Gln Ile Asp Lys Ser Ile Tyr Leu Tyr Gly Ser
                565                 570                 575

Val Asn Gly Lys Ser Gly Trp Val Ser Lys Ala Tyr Leu Val Asp Thr
            580                 585                 590

Ala Lys Pro Thr Pro Thr Pro Thr Pro Lys Pro Ser Thr Pro Thr Thr
            595                 600                 605

Asn Asn Lys Leu Thr Val Ser Ser Leu Asn Gly Val Ala Gln Ile Asn
            610                 615                 620

Ala Lys Asn Asn Gly Leu Phe Thr Thr Val Tyr Asp Lys Thr Gly Lys
625                 630                 635                 640

Pro Thr Lys Glu Val Gln Lys Thr Phe Ala Val Thr Lys Glu Ala Ser
                645                 650                 655

Leu Gly Gly Asn Lys Phe Tyr Leu Val Lys Asp Tyr Asn Ser Pro Thr
            660                 665                 670

Leu Ile Gly Trp Val Lys Gln Gly Asp Val Ile Tyr Asn Asn Ala Lys
            675                 680                 685

```
Ser Pro Val Asn Val Met Gln Thr Tyr Thr Val Lys Pro Gly Thr Lys
    690                 695                 700

Leu Tyr Ser Val Pro Trp Gly Thr Tyr Lys Gln Glu Ala Gly Ala Val
705                 710                 715                 720

Ser Gly Thr Gly Asn Gln Thr Phe Lys Ala Thr Lys Gln Gln Ile
        725                 730                 735

Asp Lys Ser Ile Tyr Leu Tyr Gly Thr Val Asn Gly Lys Ser Gly Trp
        740                 745                 750

Ile Ser Lys Ala Tyr Leu Ala Val Pro Ala Ala Pro Lys Lys Ala Val
    755                 760                 765

Ala Gln Pro Lys Thr Ala Val Lys Ala Tyr Ala Val Thr Lys Pro Gln
    770                 775                 780

Thr Thr Gln Thr Val Ser Lys Ile Ala Gln Val Lys Pro Asn Asn Thr
785                 790                 795                 800

Gly Ile Arg Ala Ser Val Tyr Glu Lys Thr Ala Lys Asn Gly Ala Lys
                805                 810                 815

Tyr Ala Asp Arg Thr Phe Tyr Val Thr Lys Glu Arg Ala His Gly Asn
                820                 825                 830

Glu Thr Tyr Val Leu Leu Asn Asn Thr Ser His Asn Ile Pro Leu Gly
        835                 840                 845

Trp Phe Asn Val Lys Asp Leu Asn Val Gln Asn Leu Gly Lys Glu Val
850                 855                 860

Lys Thr Thr Gln Lys Tyr Thr Val Asn Arg Ser Asn Asn Gly Leu Ser
865                 870                 875                 880

Met Val Pro Trp Gly Thr Lys Asn Gln Val Ile Leu Thr Gly Asn Asn
                885                 890                 895

Ile Ala Gln Gly Thr Phe Asn Ala Thr Lys Gln Val Ser Val Gly Lys
            900                 905                 910

Asp Val Tyr Leu Tyr Gly Thr Ile Asn Asn Arg Thr Gly Trp Val Asn
        915                 920                 925

Ser Lys Asp Leu Thr Ala Pro Thr Ala Val Lys Pro Thr Thr Ser Ala
    930                 935                 940

Ala Lys Asp Tyr Asn Tyr Thr Tyr Val Ile Lys Asn Gly Asn Gly Tyr
945                 950                 955                 960

Tyr Tyr Val Thr Pro Asn Ser Asp Thr Ala Lys Tyr Ser Leu Lys Ala
                965                 970                 975

Phe Asn Glu Gln Pro Phe Ala Val Val Lys Glu Gln Val Ile Asn Gly
            980                 985                 990

Gln Thr Trp Tyr Tyr Gly Lys Leu Ser Asn Gly Lys Leu Ala Trp Ile
        995                 1000                1005

Lys Ser Thr Asp Leu Ala Lys Glu Leu Ile Lys Tyr Asn Gln Ile
    1010                1015                1020

Gly Met Thr Leu Asn Gln Val Ala Gln Ile Gln Ala Gly Leu Gln
    1025                1030                1035

Tyr Lys Pro Gln Val Gln Arg Val Pro Gly Lys Trp Thr Asp Ala
    1040                1045                1050

Asn Phe Asn Asp Val Lys His Ala Met Asp Thr Lys Arg Leu Ala
    1055                1060                1065

Gln Asp Pro Ala Leu Lys Tyr Gln Phe Leu Arg Leu Asp Gln Pro
    1070                1075                1080

Gln Asn Ile Ser Ile Asp Lys Ile Asn Gln Phe Leu Lys Gly Lys
    1085                1090                1095

Gly Val Leu Glu Asn Gln Gly Ala Ala Phe Asn Lys Ala Ala Gln
```

```
                  1100               1105              1110
Met Tyr Gly Ile Asn Glu Val Tyr Leu Ile Ser His Ala Leu Leu
    1115               1120              1125

Glu Thr Gly Asn Gly Thr Ser Gln Leu Ala Lys Gly Ala Asp Val
    1130               1135              1140

Val Asn Asn Lys Val Val Thr Asn Ser Asn Thr Lys Tyr His Asn
    1145               1150              1155

Val Phe Gly Ile Ala Ala Tyr Asp Asn Asp Pro Leu Arg Glu Gly
    1160               1165              1170

Ile Lys Tyr Ala Lys Gln Ala Gly Trp Asp Thr Val Ser Lys Ala
    1175               1180              1185

Ile Val Gly Gly Ala Lys Phe Ile Gly Asn Ser Tyr Val Lys Ala
    1190               1195              1200

Gly Gln Asn Thr Leu Tyr Lys Met Arg Trp Asn Pro Ala His Pro
    1205               1210              1215

Gly Thr His Gln Tyr Ala Thr Asp Val Asp Trp Ala Asn Ile Asn
    1220               1225              1230

Ala Lys Ile Ile Lys Gly Tyr Tyr Asp Lys Ile Gly Glu Val Gly
    1235               1240              1245

Lys Tyr Phe Asp Ile Pro Gln Tyr Lys
    1250               1255

<210> SEQ ID NO 4
<211> LENGTH: 395
<212> TYPE: PRT
<213> ORGANISM: Staphylococcus simulans

<400> SEQUENCE: 4

Ala Asn Gln Val Gln Pro Leu Asn Lys Tyr Pro Val Val Phe Val His
1               5                   10                  15

Gly Phe Leu Gly Leu Val Gly Asp Asn Ala Pro Ala Leu Tyr Pro Asn
            20                  25                  30

Tyr Trp Gly Gly Asn Lys Phe Lys Val Ile Glu Glu Leu Arg Lys Gln
        35                  40                  45

Gly Tyr Asn Val His Gln Ala Ser Val Ser Ala Phe Gly Ser Asn Tyr
    50                  55                  60

Asp Arg Ala Val Glu Leu Tyr Tyr Tyr Ile Lys Gly Gly Arg Val Asp
65                  70                  75                  80

Tyr Gly Ala Ala His Ala Ala Lys Tyr Gly His Glu Arg Tyr Gly Lys
                85                  90                  95

Thr Tyr Lys Gly Ile Met Pro Asn Trp Glu Pro Gly Lys Lys Val His
            100                 105                 110

Leu Val Gly His Ser Met Gly Gly Gln Thr Ile Arg Leu Met Glu Glu
        115                 120                 125

Phe Leu Arg Asn Gly Asn Lys Glu Glu Ile Ala Tyr His Lys Ala His
    130                 135                 140

Gly Gly Glu Ile Ser Pro Leu Phe Thr Gly Gly His Asn Asn Met Val
145                 150                 155                 160

Ala Ser Ile Thr Thr Leu Ala Thr Pro His Asn Gly Ser Gln Ala Ala
                165                 170                 175

Asp Lys Phe Gly Asn Thr Glu Ala Val Arg Lys Ile Met Phe Ala Leu
            180                 185                 190

Asn Arg Phe Met Gly Asn Lys Tyr Ser Asn Ile Asp Leu Gly Leu Thr
        195                 200                 205

Gln Trp Gly Phe Lys Gln Leu Pro Asn Glu Ser Tyr Ile Asp Tyr Ile
```

```
            210                 215                 220
Lys Arg Val Ser Lys Ser Lys Ile Trp Thr Ser Asp Asp Asn Ala Ala
225                 230                 235                 240

Tyr Asp Leu Thr Leu Asp Gly Ser Ala Lys Leu Asn Asn Met Thr Ser
                245                 250                 255

Met Asn Pro Asn Ile Thr Tyr Thr Thr Tyr Thr Gly Val Ser Ser His
                260                 265                 270

Thr Gly Pro Leu Gly Tyr Glu Asn Pro Asp Leu Gly Thr Phe Phe Leu
                275                 280                 285

Met Asp Thr Thr Ser Arg Ile Ile Gly His Asp Ala Arg Glu Glu Trp
                290                 295                 300

Arg Lys Asn Asp Gly Val Val Pro Val Ile Ser Ser Leu His Pro Ser
305                 310                 315                 320

Asn Gln Pro Phe Val Asn Val Thr Asn Asp Glu Pro Ala Thr Arg Arg
                325                 330                 335

Gly Ile Trp Gln Val Lys Pro Ile Ile Gln Gly Trp Asp His Val Asp
                340                 345                 350

Phe Ile Gly Val Asp Phe Leu Asp Phe Lys Arg Lys Gly Ala Glu Leu
                355                 360                 365

Ala Asn Phe Tyr Thr Gly Ile Ile Asn Asp Leu Leu Arg Val Glu Ala
                370                 375                 380

Thr Glu Ser Lys Gly Thr Gln Leu Lys Ala Ser
385                 390                 395

<210> SEQ ID NO 5
<211> LENGTH: 319
<212> TYPE: PRT
<213> ORGANISM: Staphylococcus aureus

<400> SEQUENCE: 5

Met Lys Thr Arg Ile Val Ser Ser Val Thr Thr Thr Leu Leu Leu Gly
1               5                   10                  15

Ser Ile Leu Met Asn Pro Val Ala Asn Ala Ala Asp Ser Asp Ile Asn
                20                  25                  30

Ile Lys Thr Gly Thr Thr Asp Ile Gly Ser Asn Thr Thr Val Lys Thr
                35                  40                  45

Gly Asp Leu Val Thr Tyr Asp Lys Glu Asn Gly Met His Lys Lys Val
50                  55                  60

Phe Tyr Ser Phe Ile Asp Asp Lys Asn His Asn Lys Lys Leu Leu Val
65                  70                  75                  80

Ile Arg Thr Lys Gly Thr Ile Ala Gly Gln Tyr Arg Val Tyr Ser Glu
                85                  90                  95

Glu Gly Ala Asn Lys Ser Gly Leu Ala Trp Pro Ser Ala Phe Lys Val
                100                 105                 110

Gln Leu Gln Leu Pro Asp Asn Glu Val Ala Gln Ile Ser Asp Tyr Tyr
                115                 120                 125

Pro Arg Asn Ser Ile Asp Thr Lys Glu Tyr Met Ser Thr Leu Thr Tyr
                130                 135                 140

Gly Phe Asn Gly Asn Val Thr Gly Asp Asp Thr Gly Lys Ile Gly Gly
145                 150                 155                 160

Leu Ile Gly Ala Asn Val Ser Ile Gly His Thr Leu Lys Tyr Val Gln
                165                 170                 175

Pro Asp Phe Lys Thr Ile Leu Glu Ser Pro Thr Asp Lys Lys Val Gly
                180                 185                 190

Trp Lys Val Ile Phe Asn Asn Met Val Asn Gln Asn Trp Gly Pro Tyr
```

-continued

```
                195                 200                 205
Asp Arg Asp Ser Trp Asn Pro Val Tyr Gly Asn Gln Leu Phe Met Lys
210                 215                 220

Thr Arg Asn Gly Ser Met Lys Ala Ala Glu Asn Phe Leu Asp Pro Asn
225                 230                 235                 240

Lys Ala Ser Ser Leu Leu Ser Ser Gly Phe Ser Pro Asp Phe Ala Thr
                245                 250                 255

Val Ile Thr Met Asp Arg Lys Ala Ser Lys Gln Gln Thr Asn Ile Asp
                260                 265                 270

Val Ile Tyr Glu Arg Val Arg Asp Asp Tyr Gln Leu His Trp Thr Ser
                275                 280                 285

Thr Asn Trp Lys Gly Thr Asn Thr Lys Asp Lys Trp Thr Asp Arg Ser
290                 295                 300

Ser Glu Arg Tyr Lys Ile Asp Trp Glu Lys Glu Met Thr Asn
305                 310                 315

<210> SEQ ID NO 6
<211> LENGTH: 943
<212> TYPE: PRT
<213> ORGANISM: Staphylococcus aureus

<400> SEQUENCE: 6

Met Leu Gly Val Ile Asn Arg Met Ala Lys Lys Phe Asn Tyr Lys Leu
1               5                   10                  15

Pro Ser Met Val Ala Leu Thr Leu Val Gly Ser Ala Val Thr Ala His
                20                  25                  30

Gln Val Gln Ala Ala Glu Thr Thr Gln Asp Gln Thr Thr Asn Lys Asn
            35                  40                  45

Val Leu Asp Ser Asn Lys Val Lys Ala Thr Thr Glu Gln Ala Lys Ala
        50                  55                  60

Glu Val Lys Asn Pro Thr Gln Asn Ile Ser Gly Thr Gln Val Tyr Gln
65                  70                  75                  80

Asp Pro Ala Ile Val Gln Pro Lys Thr Ala Asn Asn Lys Thr Gly Asn
                85                  90                  95

Ala Gln Val Ser Gln Lys Val Asp Thr Ala Gln Val Asn Gly Asp Thr
            100                 105                 110

Arg Ala Asn Gln Ser Ala Thr Thr Asn Asn Thr Gln Pro Val Ala Lys
        115                 120                 125

Ser Thr Ser Thr Thr Ala Pro Lys Thr Asn Thr Asn Val Thr Asn Ala
130                 135                 140

Gly Tyr Ser Leu Val Asp Asp Glu Asp Asn Ser Glu His Gln Ile
145                 150                 155                 160

Asn Pro Glu Leu Ile Lys Ser Ala Ala Lys Pro Ala Ala Leu Glu Thr
                165                 170                 175

Gln Tyr Lys Ala Ala Pro Lys Ala Lys Thr Glu Ala Thr Pro Lys
            180                 185                 190

Val Thr Thr Phe Ser Ala Ser Ala Gln Pro Arg Ser Val Ala Ala Thr
        195                 200                 205

Pro Lys Thr Ser Leu Pro Lys Tyr Lys Pro Gln Val Asn Ser Ser Ile
210                 215                 220

Asn Asp Tyr Ile Arg Lys Asn Leu Lys Ala Pro Lys Ile Glu Glu
225                 230                 235                 240

Asp Tyr Thr Ser Tyr Phe Pro Lys Tyr Ala Tyr Arg Asn Gly Val Gly
                245                 250                 255

Arg Pro Glu Gly Ile Val Val His Asp Thr Ala Asn Asp Arg Ser Thr
```

```
                 260             265             270
Ile Asn Gly Glu Ile Ser Tyr Met Lys Asn Asn Tyr Gln Asn Ala Phe
            275             280             285
Val His Ala Phe Val Asp Gly Asp Arg Ile Ile Glu Thr Ala Pro Thr
            290             295             300
Asp Tyr Leu Ser Trp Gly Val Gly Ala Val Gly Asn Pro Arg Phe Ile
305             310             315             320
Asn Val Glu Ile Val His Thr His Asp Tyr Ala Ser Phe Ala Arg Ser
            325             330             335
Met Asn Asn Tyr Ala Asp Tyr Ala Ala Thr Gln Leu Gln Tyr Tyr Gly
            340             345             350
Leu Lys Pro Asp Ser Ala Glu Tyr Asp Gly Asn Gly Thr Val Trp Thr
            355             360             365
His Tyr Ala Val Ser Lys Tyr Leu Gly Gly Thr Asp His Ala Asp Pro
            370             375             380
His Gly Tyr Leu Arg Ser His Asn Tyr Ser Tyr Asp Gln Leu Tyr Asp
385             390             395             400
Leu Ile Asn Glu Lys Tyr Leu Ile Lys Met Gly Lys Val Ala Pro Trp
                405             410             415
Gly Thr Gln Phe Thr Thr Thr Pro Thr Pro Ser Lys Pro Thr Thr
                420             425             430
Pro Ser Lys Pro Ser Thr Gly Lys Leu Thr Val Ala Ala Asn Asn Gly
            435             440             445
Val Ala Gln Ile Lys Pro Thr Asn Ser Gly Leu Tyr Thr Thr Val Tyr
            450             455             460
Asp Lys Thr Gly Lys Ala Thr Asn Glu Val Gln Lys Thr Phe Ala Val
465             470             475             480
Ser Lys Thr Ala Thr Leu Gly Asn Gln Lys Phe Tyr Leu Val Gln Asp
                485             490             495
Tyr Asn Ser Gly Asn Lys Phe Gly Trp Val Lys Glu Gly Asp Val Val
                500             505             510
Tyr Asn Thr Ala Lys Ser Pro Val Asn Val Asn Gln Ser Tyr Ser Ile
            515             520             525
Lys Ser Gly Thr Lys Leu Tyr Thr Val Pro Trp Gly Thr Ser Lys Gln
            530             535             540
Val Ala Gly Ser Val Ser Gly Ser Gly Asn Gln Thr Phe Lys Ala Ser
545             550             555             560
Lys Gln Gln Gln Ile Asp Lys Ser Ile Tyr Leu Tyr Gly Ser Val Asn
                565             570             575
Gly Lys Ser Gly Trp Val Ser Lys Ala Tyr Leu Val Asp Thr Ala Lys
            580             585             590
Pro Thr Pro Thr Pro Ile Pro Lys Pro Ser Thr Pro Thr Thr Asn Asn
            595             600             605
Lys Leu Thr Val Ser Ser Leu Asn Gly Val Ala Gln Ile Asn Ala Lys
            610             615             620
Asn Asn Gly Leu Phe Thr Thr Val Tyr Asp Lys Thr Gly Lys Pro Thr
625             630             635             640
Lys Glu Val Gln Lys Thr Phe Ala Val Thr Lys Glu Ala Ser Leu Gly
                645             650             655
Gly Asn Lys Phe Tyr Leu Val Lys Asp Tyr Asn Ser Pro Thr Leu Ile
                660             665             670
Gly Trp Val Lys Gln Gly Asp Val Ile Tyr Asn Asn Ala Lys Ser Pro
            675             680             685
```

Val Asn Val Met Gln Thr Tyr Thr Val Lys Pro Gly Thr Lys Leu Tyr
            690                 695                 700

Ser Val Pro Trp Gly Thr Tyr Lys Gln Glu Ala Gly Ala Val Ser Gly
705                 710                 715                 720

Thr Gly Asn Gln Thr Phe Lys Ala Thr Lys Gln Gln Ile Asp Lys
                725                 730                 735

Ser Ile Tyr Leu Phe Gly Thr Val Asn Gly Lys Ser Gly Trp Val Ser
                740                 745                 750

Lys Ala Tyr Leu Ala Val Pro Ala Ala Pro Lys Lys Ala Val Ala Gln
            755                 760                 765

Pro Lys Thr Ala Val Lys Ala Tyr Thr Val Thr Lys Pro Gln Thr Thr
            770                 775                 780

Gln Thr Val Ser Lys Ile Ala Gln Val Lys Pro Asn Asn Thr Gly Ile
785                 790                 795                 800

Arg Ala Ser Val Tyr Glu Lys Thr Ala Lys Asn Gly Ala Lys Tyr Ala
                805                 810                 815

Asp Arg Thr Phe Tyr Val Thr Lys Glu Arg Ala His Gly Asn Glu Thr
                820                 825                 830

Tyr Val Leu Leu Asn Asn Thr Ser His Asn Ile Pro Leu Gly Trp Phe
            835                 840                 845

Asn Val Lys Asp Leu Asn Val Gln Asn Leu Gly Lys Glu Val Lys Thr
850                 855                 860

Thr Gln Lys Tyr Thr Val Asn Lys Ser Asn Asn Gly Leu Ser Met Val
865                 870                 875                 880

Pro Trp Gly Thr Lys Asn Gln Val Ile Leu Thr Gly Asn Asn Ile Ala
                885                 890                 895

Gln Gly Thr Phe Asn Ala Thr Lys Gln Val Ser Val Gly Lys Asp Val
            900                 905                 910

Tyr Tyr Thr Val Leu Leu Ile Thr Ala Leu Val Gly Lys Ala Lys Asp
            915                 920                 925

Leu Pro His Gln Leu Gly Asn Gln Leu His Gln Leu Pro Lys Ile
            930                 935                 940

<210> SEQ ID NO 7
<211> LENGTH: 166
<212> TYPE: PRT
<213> ORGANISM: Staphylococcus aureus

<400> SEQUENCE: 7

Met Ile Thr Tyr Lys Asn Ile Leu Ile Ala Val Asp Gly Ser His Glu
1               5                   10                  15

Ala Glu Trp Ala Phe Asn Arg Ala Val Gly Val Ala Lys Arg Asn Asp
                20                  25                  30

Ala Lys Leu Thr Ile Val Asn Val Ile Asp Ser Arg Thr Tyr Ser Ser
            35                  40                  45

Tyr Glu Val Tyr Asp Ala Gln Phe Thr Glu Lys Ser Lys His Phe Ala
        50                  55                  60

Glu Glu Leu Leu Asn Gly Tyr Lys Glu Val Ala Thr Asn Ala Gly Val
65                  70                  75                  80

Lys Asp Val Glu Thr Arg Leu Glu Phe Gly Ser Pro Lys Ser Ile Ile
                85                  90                  95

Pro Lys Lys Leu Ala His Glu Ile Asn Ala Asp Leu Ile Met Ser Gly
                100                 105                 110

Thr Ser Gly Leu Asn Ala Val Glu Arg Phe Ile Val Gly Ser Val Ser
            115                 120                 125

```
Glu Ser Ile Val Arg His Ala Pro Cys Asp Val Leu Val Arg Thr
            130                 135                 140

Glu Glu Leu Pro Ala Asp Phe Gln Pro Gln Val Ala Thr Thr Gln Leu
145                 150                 155                 160

Arg Glu Lys Tyr Gln Asn
                165

<210> SEQ ID NO 8
<211> LENGTH: 199
<212> TYPE: PRT
<213> ORGANISM: Staphylococcus aureus

<400> SEQUENCE: 8

Met Ala Phe Glu Leu Pro Lys Leu Pro Tyr Ala Phe Asp Ala Leu Glu
1               5                   10                  15

Pro His Phe Asp Lys Glu Thr Met Glu Ile His His Asp Arg His His
                20                  25                  30

Asn Thr Tyr Val Thr Lys Leu Asn Ala Ala Val Glu Gly Thr Asp Leu
            35                  40                  45

Glu Ser Lys Ser Ile Glu Glu Ile Val Ala Asn Leu Asp Ser Val Pro
50                  55                  60

Ala Asn Ile Gln Thr Ala Val Arg Asn Asn Gly Gly His Leu Asn
65                  70                  75                  80

His Ser Leu Phe Trp Glu Leu Leu Ser Pro Asn Ser Glu Glu Lys Gly
                85                  90                  95

Thr Val Val Glu Lys Ile Lys Glu Gln Trp Gly Ser Leu Glu Glu Phe
            100                 105                 110

Lys Lys Glu Phe Ala Asp Lys Ala Ala Ala Arg Phe Gly Ser Gly Trp
        115                 120                 125

Ala Trp Leu Val Val Asn Asn Gly Gln Leu Glu Ile Val Thr Thr Pro
130                 135                 140

Asn Gln Asp Asn Pro Leu Thr Gly Leu Lys Thr Pro Ile Leu Gly Leu
145                 150                 155                 160

Asp Val Trp Glu His Ala Tyr Tyr Leu Lys Tyr Gln Asn Lys Arg Pro
                165                 170                 175

Asp Tyr Ile Gly Ala Phe Trp Asn Val Val Asn Trp Glu Lys Val Asp
            180                 185                 190

Glu Leu Tyr Asn Ala Thr Lys
            195

<210> SEQ ID NO 9
<211> LENGTH: 228
<212> TYPE: PRT
<213> ORGANISM: Staphylococcus aureus

<400> SEQUENCE: 9

Met Pro Lys Leu Ile Leu Cys Arg His Gly Gln Ser Glu Trp Asn Ala
1               5                   10                  15

Lys Asn Leu Phe Thr Gly Trp Glu Asp Val Asn Leu Ser Glu Gln Gly
                20                  25                  30

Ile Asn Glu Ala Thr Arg Ala Gly Glu Lys Val Arg Glu Asn Asn Ile
            35                  40                  45

Ala Ile Asp Val Ala Phe Thr Ser Leu Leu Thr Arg Ala Leu Asp Thr
50                  55                  60

Thr His Tyr Ile Leu Thr Glu Ser Lys Gln Gln Trp Ile Pro Val Tyr
65                  70                  75                  80

Lys Ser Trp Arg Leu Asn Glu Arg His Tyr Gly Gly Leu Gln Gly Leu
```

```
                    85                  90                  95
Asn Lys Asp Asp Ala Arg Lys Glu Phe Gly Glu Glu Gln Val His Ile
            100                 105                 110

Trp Arg Arg Ser Tyr Asp Val Lys Pro Pro Ala Glu Thr Glu Glu Gln
        115                 120                 125

Arg Glu Ala Tyr Leu Ala Asp Arg Arg Tyr Asn His Leu Asp Lys Arg
    130                 135                 140

Met Met Pro Tyr Ser Glu Ser Leu Lys Asp Thr Leu Val Arg Val Ile
145                 150                 155                 160

Pro Phe Trp Thr Asp His Ile Ser Gln Tyr Leu Leu Asp Gly Gln Thr
                165                 170                 175

Val Leu Val Ser Ala His Gly Asn Ser Ile Arg Ala Leu Ile Lys Tyr
            180                 185                 190

Leu Glu Asp Val Ser Asp Glu Asp Ile Ile Asn Tyr Glu Ile Lys Thr
        195                 200                 205

Gly Ala Pro Leu Val Tyr Glu Leu Thr Asp Asp Leu Gly Val Ile Asp
    210                 215                 220

Lys Tyr Tyr Leu
225

<210> SEQ ID NO 10
<211> LENGTH: 189
<212> TYPE: PRT
<213> ORGANISM: Staphylococcus aureus

<400> SEQUENCE: 10

Met Ser Leu Ile Asn Lys Glu Ile Leu Pro Phe Thr Ala Gln Ala Phe
1               5                   10                  15

Asp Pro Lys Lys Asp Gln Phe Lys Glu Val Thr Gln Glu Asp Leu Lys
            20                  25                  30

Gly Ser Trp Ser Val Val Cys Phe Tyr Pro Ala Asp Phe Ser Phe Val
        35                  40                  45

Cys Pro Thr Glu Leu Glu Asp Leu Gln Asn Gln Tyr Glu Glu Leu Gln
    50                  55                  60

Lys Leu Gly Val Asn Val Phe Ser Val Ser Thr Asp Thr His Phe Val
65                  70                  75                  80

His Lys Ala Trp His Asp His Ser Asp Ala Ile Ser Lys Ile Thr Tyr
                85                  90                  95

Thr Met Ile Gly Asp Pro Ser Gln Thr Ile Thr Arg Asn Phe Asp Val
            100                 105                 110

Leu Asp Glu Ala Thr Gly Leu Ala Gln Arg Gly Thr Phe Ile Ile Asp
        115                 120                 125

Pro Asp Gly Val Val Gln Ala Ser Glu Ile Asn Ala Asp Gly Ile Gly
    130                 135                 140

Arg Asp Ala Ser Thr Leu Ala His Lys Ile Lys Ala Ala Gln Tyr Val
145                 150                 155                 160

Arg Lys Asn Pro Gly Glu Val Cys Pro Ala Lys Trp Glu Glu Gly Ala
                165                 170                 175

Lys Thr Leu Gln Pro Gly Leu Asp Leu Val Gly Lys Ile
            180                 185

<210> SEQ ID NO 11
<211> LENGTH: 446
<212> TYPE: PRT
<213> ORGANISM: Staphylococcus aureus

<400> SEQUENCE: 11
```

```
Met Pro Lys Arg Thr Phe Thr Lys Asp Asp Ile Arg Lys Phe Ala Glu
1               5                   10                  15

Glu Glu Asn Val Arg Tyr Leu Arg Leu Gln Phe Thr Asp Ile Leu Gly
            20                  25                  30

Thr Ile Lys Asn Val Glu Val Pro Val Ser Gln Leu Glu Lys Val Leu
            35                  40                  45

Asp Asn Glu Met Met Phe Asp Gly Ser Ser Ile Glu Gly Phe Val Arg
        50                  55                  60

Ile Glu Glu Ser Asp Met Tyr Leu His Pro Asp Leu Asp Thr Trp Val
65                  70                  75                  80

Ile Phe Pro Trp Thr Ala Gly Gln Gly Lys Val Ala Arg Leu Ile Cys
                85                  90                  95

Asp Val Tyr Lys Thr Asp Gly Thr Pro Phe Glu Gly Asp Pro Arg Ala
            100                 105                 110

Asn Leu Lys Arg Val Leu Lys Glu Met Glu Asp Leu Gly Phe Thr Asp
            115                 120                 125

Phe Asn Leu Gly Pro Glu Pro Glu Phe Phe Leu Phe Lys Leu Asp Glu
        130                 135                 140

Lys Gly Glu Pro Thr Leu Glu Leu Asn Asp Asp Gly Gly Tyr Phe Asp
145                 150                 155                 160

Leu Ala Pro Thr Asp Leu Gly Glu Asn Cys Arg Arg Asp Ile Val Leu
                165                 170                 175

Glu Leu Glu Asp Met Gly Phe Asp Ile Glu Ala Ser His His Glu Val
            180                 185                 190

Ala Pro Gly Gln His Glu Ile Asp Phe Lys Tyr Ala Asp Ala Val Thr
        195                 200                 205

Ala Cys Asp Asn Ile Gln Thr Phe Lys Leu Val Val Lys Thr Ile Ala
        210                 215                 220

Arg Lys His Asn Leu His Ala Thr Phe Met Pro Lys Pro Leu Phe Gly
225                 230                 235                 240

Val Asn Gly Ser Gly Met His Phe Asn Val Ser Leu Phe Lys Gly Lys
                245                 250                 255

Glu Asn Ala Phe Phe Asp Pro Asn Thr Glu Met Gly Leu Thr Glu Thr
            260                 265                 270

Ala Tyr Gln Phe Thr Ala Gly Val Leu Lys Asn Ala Arg Gly Phe Thr
        275                 280                 285

Ala Val Cys Asn Pro Leu Val Asn Ser Tyr Lys Arg Leu Val Pro Gly
        290                 295                 300

Tyr Glu Ala Pro Cys Tyr Ile Ala Trp Ser Gly Lys Asn Arg Ser Pro
305                 310                 315                 320

Leu Ile Arg Val Pro Ser Ser Arg Gly Leu Ser Thr Arg Ile Glu Val
                325                 330                 335

Arg Ser Val Asp Pro Ala Ala Asn Pro Tyr Met Ala Leu Ala Ala Ile
            340                 345                 350

Leu Glu Ala Gly Leu Asp Gly Ile Lys Asn Lys Leu Lys Val Pro Glu
        355                 360                 365

Pro Val Asn Gln Asn Ile Tyr Glu Met Asn Arg Glu Glu Arg Glu Ala
        370                 375                 380

Val Gly Ile Gln Asp Leu Pro Ser Thr Leu Tyr Thr Ala Leu Lys Ala
385                 390                 395                 400

Met Arg Glu Asn Glu Val Ile Lys Lys Ala Leu Gly Asn His Ile Tyr
            405                 410                 415

Asn Gln Phe Ile Asn Ser Lys Ser Ile Glu Trp Asp Tyr Tyr Arg Thr
```

```
                420                 425                 430
Gln Val Ser Glu Trp Glu Arg Asp Gln Tyr Met Lys Gln Tyr
        435                 440                 445

<210> SEQ ID NO 12
<211> LENGTH: 195
<212> TYPE: PRT
<213> ORGANISM: Staphylococcus aureus

<400> SEQUENCE: 12

Met Asn Leu Ile Pro Thr Val Ile Glu Thr Thr Asn Arg Gly Glu Arg
1               5                   10                  15

Ala Tyr Asp Ile Tyr Ser Arg Leu Leu Lys Asp Arg Ile Ile Met Leu
            20                  25                  30

Gly Ser Gln Ile Asp Asp Asn Val Ala Asn Ser Ile Val Ser Gln Leu
        35                  40                  45

Leu Phe Leu Gln Ala Gln Asp Ser Glu Lys Asp Ile Tyr Leu Tyr Ile
    50                  55                  60

Asn Ser Pro Gly Gly Ser Val Thr Ala Gly Phe Ala Ile Tyr Asp Thr
65                  70                  75                  80

Ile Gln His Ile Lys Pro Asp Val Gln Thr Ile Cys Ile Gly Met Ala
                85                  90                  95

Ala Ser Met Gly Ser Phe Leu Leu Ala Ala Gly Ala Lys Gly Lys Arg
            100                 105                 110

Phe Ala Leu Pro Asn Ala Glu Val Met Ile His Gln Pro Leu Gly Gly
        115                 120                 125

Ala Gln Gly Gln Ala Thr Glu Ile Glu Ile Ala Ala Asn His Ile Leu
    130                 135                 140

Lys Thr Arg Glu Lys Leu Asn Arg Ile Leu Ser Glu Arg Thr Gly Gln
145                 150                 155                 160

Ser Ile Glu Lys Ile Gln Lys Asp Thr Asp Arg Asp Asn Phe Leu Thr
                165                 170                 175

Ala Glu Glu Ala Lys Glu Tyr Gly Leu Ile Asp Glu Val Met Val Pro
            180                 185                 190

Glu Thr Lys
        195

<210> SEQ ID NO 13
<211> LENGTH: 309
<212> TYPE: PRT
<213> ORGANISM: Staphylococcus aureus

<400> SEQUENCE: 13

Met Lys Lys Leu Val Pro Leu Leu Ala Leu Leu Leu Val Ala
1               5                   10                  15

Ala Cys Gly Thr Gly Gly Lys Gln Ser Ser Asp Lys Ser Asn Gly Lys
            20                  25                  30

Leu Lys Val Val Thr Thr Asn Ser Ile Leu Tyr Asp Met Ala Lys Asn
        35                  40                  45

Val Gly Gly Asp Asn Val Asp Ile His Ser Ile Val Pro Val Gly Gln
    50                  55                  60

Asp Pro His Glu Tyr Glu Val Lys Pro Lys Asp Ile Lys Lys Leu Thr
65                  70                  75                  80

Asp Ala Asp Val Ile Leu Tyr Asn Gly Leu Asn Leu Glu Thr Gly Asn
                85                  90                  95

Gly Trp Phe Glu Lys Ala Leu Glu Gln Ala Gly Lys Ser Leu Lys Asp
            100                 105                 110
```

Lys Lys Val Ile Ala Val Ser Lys Asp Val Lys Pro Ile Tyr Leu Asn
            115                 120                 125

Gly Glu Glu Gly Asn Lys Asp Lys Gln Asp Pro His Ala Trp Leu Ser
        130                 135                 140

Leu Asp Asn Gly Ile Lys Tyr Val Lys Thr Ile Gln Gln Thr Phe Ile
145                 150                 155                 160

Asp Asn Asp Lys Lys His Lys Ala Asp Tyr Glu Lys Gln Gly Asn Lys
                165                 170                 175

Tyr Ile Ala Gln Leu Glu Lys Leu Asn Asn Asp Ser Lys Asp Lys Phe
            180                 185                 190

Asn Asp Ile Pro Lys Glu Gln Arg Ala Met Ile Thr Ser Glu Gly Ala
        195                 200                 205

Phe Lys Tyr Phe Ser Lys Gln Tyr Gly Ile Thr Pro Gly Tyr Ile Trp
    210                 215                 220

Glu Ile Asn Thr Glu Lys Gln Gly Thr Pro Glu Gln Met Arg Gln Ala
225                 230                 235                 240

Ile Glu Phe Val Lys Lys His Lys Leu Lys His Leu Leu Val Glu Thr
                245                 250                 255

Ser Val Asp Lys Lys Ala Met Glu Ser Leu Ser Glu Glu Thr Lys Lys
            260                 265                 270

Asp Ile Phe Gly Glu Val Tyr Thr Asp Ser Ile Gly Lys Glu Gly Thr
        275                 280                 285

Lys Gly Asp Ser Tyr Tyr Lys Met Met Lys Ser Asn Ile Glu Thr Val
    290                 295                 300

His Gly Ser Met Lys
305

<210> SEQ ID NO 14
<211> LENGTH: 681
<212> TYPE: PRT
<213> ORGANISM: Staphylococcus aureus

<400> SEQUENCE: 14

Met Met Lys Ser Gln Asn Lys Tyr Ser Ile Arg Lys Phe Ser Val Gly
1               5                   10                  15

Ala Ser Ser Ile Leu Ile Ala Thr Leu Leu Phe Leu Ser Gly Gly Gln
            20                  25                  30

Ala Gln Ala Ala Glu Lys Gln Val Asn Met Gly Asn Ser Gln Glu Asp
        35                  40                  45

Thr Val Thr Ala Gln Ser Ile Gly Asp Gln Gln Thr Arg Glu Asn Ala
    50                  55                  60

Asn Tyr Gln Arg Glu Asn Gly Val Asp Glu Gln His Thr Glu Asn
65                  70                  75                  80

Leu Thr Lys Asn Leu His Asn Asp Lys Thr Ile Ser Glu Glu Asn His
                85                  90                  95

Arg Lys Thr Asp Asp Leu Asn Lys Asp Gln Leu Lys Asp Asp Lys Asn
            100                 105                 110

Ser Ser Leu Asn Asn Lys Asn Ile Gln Arg Asp Thr Thr Lys Asn Asn
        115                 120                 125

Asn Ala Asn Pro Ser Asp Val Asn Gln Gly Leu Glu Gln Ala Ile Asn
    130                 135                 140

Asp Gly Lys Gln Ser Lys Val Ala Ser Gln Gln Ser Lys Glu Val
145                 150                 155                 160

Asp Asn Ser Gln Asp Ser Asn Ala Asn Asn Leu Pro Ser Gln Ser
                165                 170                 175

```
Leu Thr Lys Glu Ala Pro Ser Leu Asn Lys Ser Asp Gln Thr Ser Gln
            180                 185                 190

Arg Glu Ile Val Asn Glu Thr Glu Ile Glu Lys Val Gln Pro Gln Gln
        195                 200                 205

Asn Asn Gln Ala Asn Asp Lys Ile Thr Asn His Phe Asn Asn Glu
210                 215                 220

Gln Glu Val Lys Pro Gln Lys Asp Glu Lys Thr Leu Ser Val Ser Asp
225                 230                 235                 240

Leu Lys Asn Asn Gln Lys Ser Pro Val Glu Pro Thr Lys Asp Asn Asp
            245                 250                 255

Lys Lys Asn Gly Leu Asn Leu Leu Lys Ser Ser Ala Val Ala Thr Leu
            260                 265                 270

Pro Asn Lys Gly Thr Lys Glu Leu Thr Ala Lys Ala Lys Asp Asp Gln
            275                 280                 285

Thr Asn Lys Val Ala Lys Gln Gly Gln Tyr Lys Asn Gln Asp Pro Ile
            290                 295                 300

Val Leu Val His Gly Phe Asn Gly Phe Thr Asp Asp Ile Asn Pro Ser
305                 310                 315                 320

Val Leu Ala His Tyr Trp Gly Gly Asn Lys Met Asn Ile Arg Gln Asp
            325                 330                 335

Leu Glu Glu Asn Gly Tyr Lys Ala Tyr Glu Ala Ser Ile Ser Ala Phe
            340                 345                 350

Gly Ser Asn Tyr Asp Arg Ala Val Glu Leu Tyr Tyr Ile Lys Gly
            355                 360                 365

Gly Arg Val Asp Tyr Gly Ala Ala His Ala Ala Lys Tyr Gly His Glu
            370                 375                 380

Arg Tyr Gly Lys Thr Tyr Glu Gly Ile Tyr Lys Asp Trp Lys Pro Gly
385                 390                 395                 400

Gln Lys Val His Leu Val Gly His Ser Met Gly Gly Gln Thr Ile Arg
            405                 410                 415

Gln Leu Glu Glu Leu Leu Arg Asn Gly Asn Arg Glu Glu Ile Glu Tyr
            420                 425                 430

Gln Lys Lys His Gly Gly Glu Ile Ser Pro Leu Phe Lys Gly Asn Asn
            435                 440                 445

Asp Asn Met Ile Ser Ser Ile Thr Thr Leu Gly Thr Pro His Asn Gly
450                 455                 460

Thr His Ala Ser Asp Leu Ala Gly Asn Glu Ala Leu Val Arg Gln Ile
465                 470                 475                 480

Val Phe Asp Ile Gly Lys Met Phe Gly Asn Lys Asn Ser Arg Val Asp
            485                 490                 495

Phe Gly Leu Ala Gln Trp Gly Leu Lys Gln Lys Pro Asn Glu Ser Tyr
            500                 505                 510

Ile Asp Tyr Val Lys Arg Val Lys Gln Ser Asn Leu Trp Lys Ser Lys
            515                 520                 525

Asp Asn Gly Phe Tyr Asp Leu Thr Arg Glu Gly Ala Thr Asp Leu Asn
            530                 535                 540

Arg Lys Thr Ser Leu Asn Pro Asn Ile Val Tyr Lys Thr Tyr Thr Gly
545                 550                 555                 560

Glu Ala Thr His Lys Ala Leu Asn Ser Asp Arg Gln Lys Ala Asp Leu
            565                 570                 575

Asn Met Phe Phe Pro Phe Val Ile Thr Gly Asn Leu Ile Gly Lys Ala
            580                 585                 590

Thr Glu Lys Glu Trp Arg Glu Asn Asp Gly Leu Val Ser Val Ile Ser
```

```
                        595                 600                 605
Ser Gln His Pro Phe Asn Gln Ala Tyr Thr Asn Ala Thr Asp Lys Ile
    610                 615                 620

Gln Lys Gly Ile Trp Gln Val Thr Pro Thr Lys His Asp Trp Asp His
625                 630                 635                 640

Val Asp Phe Val Gly Gln Asp Ser Ser Asp Thr Val Arg Thr Arg Glu
                645                 650                 655

Glu Leu Gln Asp Phe Trp His His Leu Ala Asp Leu Val Lys Thr
    660                 665                 670

Glu Lys Val Thr Asp Thr Lys Gln Ala
        675                 680

<210> SEQ ID NO 15
<211> LENGTH: 394
<212> TYPE: PRT
<213> ORGANISM: Staphylococcus aureus

<400> SEQUENCE: 15

Met Ala Lys Glu Lys Phe Asp Arg Ser Lys Glu His Ala Asn Ile Gly
1               5                   10                  15

Thr Ile Gly His Val Asp His Gly Lys Thr Thr Leu Thr Ala Ala Ile
                20                  25                  30

Ala Thr Val Leu Ala Lys Asn Gly Asp Ser Val Ala Gln Ser Tyr Asp
            35                  40                  45

Met Ile Asp Asn Ala Pro Glu Glu Lys Glu Arg Gly Ile Thr Ile Asn
        50                  55                  60

Thr Ser His Ile Glu Tyr Gln Thr Asp Lys Arg His Tyr Ala His Val
65                  70                  75                  80

Asp Cys Pro Gly His Ala Asp Tyr Val Lys Asn Met Ile Thr Gly Ala
                85                  90                  95

Ala Gln Met Asp Gly Gly Ile Leu Val Val Ser Ala Ala Asp Gly Pro
            100                 105                 110

Met Pro Gln Thr Arg Glu His Ile Leu Leu Ser Arg Asn Val Gly Val
        115                 120                 125

Pro Ala Leu Val Val Phe Leu Asn Lys Val Asp Met Val Asp Asp Glu
    130                 135                 140

Glu Leu Leu Glu Leu Val Glu Met Glu Val Arg Asp Leu Leu Ser Glu
145                 150                 155                 160

Tyr Asp Phe Pro Gly Asp Asp Val Pro Val Ile Ala Gly Ser Ala Leu
                165                 170                 175

Lys Ala Leu Glu Gly Asp Ala Gln Tyr Glu Glu Lys Ile Leu Glu Leu
            180                 185                 190

Met Glu Ala Val Asp Thr Tyr Ile Pro Thr Pro Glu Arg Asp Ser Asp
        195                 200                 205

Lys Pro Phe Met Met Pro Val Glu Asp Val Phe Ser Ile Thr Gly Arg
    210                 215                 220

Gly Thr Val Ala Thr Gly Arg Val Glu Arg Gly Gln Ile Lys Val Gly
225                 230                 235                 240

Glu Glu Val Glu Ile Ile Gly Leu His Asp Thr Ser Lys Thr Thr Val
                245                 250                 255

Thr Gly Val Glu Met Phe Arg Lys Leu Leu Asp Tyr Ala Glu Ala Gly
            260                 265                 270

Asp Asn Ile Gly Ala Leu Leu Arg Gly Val Ala Arg Glu Asp Val Gln
        275                 280                 285

Arg Gly Gln Val Leu Ala Ala Pro Gly Ser Ile Thr Pro His Thr Glu
```

```
                290                 295                 300
Phe Lys Ala Glu Val Tyr Val Leu Ser Lys Asp Glu Gly Gly Arg His
305                 310                 315                 320

Thr Pro Phe Phe Ser Asn Tyr Arg Pro Gln Phe Tyr Phe Arg Thr Thr
                325                 330                 335

Asp Val Thr Gly Val Val His Leu Pro Glu Gly Thr Glu Met Val Met
                340                 345                 350

Pro Gly Asp Asn Val Glu Met Thr Val Glu Leu Ile Ala Pro Ile Ala
                355                 360                 365

Ile Glu Asp Gly Thr Arg Phe Ser Ile Arg Glu Gly Arg Thr Val
370                 375                 380

Gly Ser Gly Val Val Thr Glu Ile Ile Lys
385                 390

<210> SEQ ID NO 16
<211> LENGTH: 662
<212> TYPE: PRT
<213> ORGANISM: Staphylococcus aureus

<400> SEQUENCE: 16

Met Phe Asn Glu Lys Asp Gln Leu Ala Val Asp Thr Leu Arg Ala Leu
1               5                   10                  15

Ser Ile Asp Thr Ile Glu Lys Ala Asn Ser Gly His Pro Gly Leu Pro
                20                  25                  30

Met Gly Ala Ala Pro Met Ala Tyr Thr Leu Trp Thr Arg His Leu Asn
                35                  40                  45

Phe Asn Pro Gln Ser Lys Asp Tyr Phe Asn Arg Asp Arg Phe Val Leu
50                  55                  60

Ser Ala Gly His Gly Ser Ala Leu Leu Tyr Ser Leu His Val Ser
65                  70                  75                  80

Gly Ser Leu Glu Leu Glu Glu Leu Lys Gln Phe Arg Gln Trp Gly Ser
                85                  90                  95

Lys Thr Pro Gly His Pro Glu Tyr Arg His Thr Asp Gly Val Glu Val
                100                 105                 110

Thr Thr Gly Pro Leu Gly Gln Gly Phe Ala Met Ser Val Gly Leu Ala
                115                 120                 125

Leu Ala Glu Asp His Leu Ala Gly Lys Phe Asn Lys Glu Gly Tyr Asn
130                 135                 140

Val Val Asp His Tyr Thr Tyr Val Leu Ala Ser Asp Gly Asp Leu Met
145                 150                 155                 160

Glu Gly Ile Ser His Glu Ala Ala Ser Phe Ala Gly His Asn Lys Leu
                165                 170                 175

Ser Lys Leu Val Val Leu Tyr Asp Ser Asn Asp Ile Ser Leu Asp Gly
                180                 185                 190

Glu Leu Asn Lys Ala Phe Ser Glu Asn Thr Lys Ala Arg Phe Glu Ala
                195                 200                 205

Tyr Gly Trp Asn Tyr Leu Leu Val Lys Asp Gly Asn Asp Leu Glu Glu
210                 215                 220

Ile Asp Lys Ala Ile Thr Thr Ala Lys Ser Gln Glu Gly Pro Thr Ile
225                 230                 235                 240

Ile Glu Val Lys Thr Thr Ile Gly Phe Gly Ser Pro Asn Lys Ala Gly
                245                 250                 255

Thr Asn Gly Val His Gly Ala Pro Leu Gly Glu Val Glu Arg Lys Leu
                260                 265                 270

Thr Phe Glu Asn Tyr Gly Leu Asp Pro Glu Lys Arg Phe Asn Val Ser
```

```
                275                 280                 285
Glu Glu Val Tyr Glu Ile Phe Gln Asn Thr Met Leu Lys Arg Ala Asn
290                 295                 300

Glu Asp Glu Ser Gln Trp Asn Ser Leu Leu Glu Lys Tyr Ala Glu Thr
305                 310                 315                 320

Tyr Pro Glu Leu Ala Glu Phe Lys Leu Ala Ile Ser Gly Lys Leu
            325                 330                 335

Pro Lys Asn Tyr Lys Asp Glu Leu Pro Arg Phe Glu Leu Gly His Asn
            340                 345                 350

Gly Ala Ser Arg Ala Asp Ser Gly Thr Val Ile Gln Ala Ile Ser Lys
            355                 360                 365

Thr Val Pro Ser Phe Phe Gly Ser Ala Asp Leu Ala Gly Ser Asn
            370                 375                 380

Lys Ser Asn Val Asn Asp Ala Thr Asp Tyr Ser Glu Thr Pro Glu
385                 390                 395                 400

Gly Lys Asn Val Trp Phe Gly Val Arg Glu Phe Ala Met Gly Ala Ala
                405                 410                 415

Val Asn Gly Met Ala Ala His Gly Gly Leu His Pro Tyr Gly Ala Thr
            420                 425                 430

Phe Phe Val Phe Ser Asp Tyr Leu Lys Pro Ala Leu Arg Leu Ser Ser
        435                 440                 445

Ile Met Gly Leu Asn Ala Thr Phe Ile Phe Thr His Asp Ser Ile Ala
450                 455                 460

Val Gly Glu Asp Gly Pro Thr His Glu Pro Ile Glu Gln Leu Ala Gly
465                 470                 475                 480

Leu Arg Ala Ile Pro Asn Met Asn Val Ile Arg Pro Ala Asp Gly Asn
                485                 490                 495

Glu Thr Arg Val Ala Trp Glu Val Ala Leu Glu Ser Glu Ser Thr Pro
            500                 505                 510

Thr Ser Leu Val Leu Thr Arg Gln Asn Leu Pro Val Leu Asp Val Pro
        515                 520                 525

Glu Asp Val Val Glu Glu Gly Val Arg Lys Gly Ala Tyr Thr Val Tyr
530                 535                 540

Gly Ser Glu Glu Thr Pro Glu Phe Leu Leu Leu Ala Ser Gly Ser Glu
545                 550                 555                 560

Val Ser Leu Ala Val Glu Ala Ala Lys Asp Leu Glu Lys Gln Gly Lys
                565                 570                 575

Ser Val Arg Val Val Ser Met Pro Asn Trp Asn Ala Phe Glu Gln Gln
            580                 585                 590

Ser Glu Glu Tyr Lys Glu Ser Val Ile Pro Ser Ser Val Thr Lys Arg
595                 600                 605

Val Ala Ile Glu Met Ala Ser Pro Leu Gly Trp His Lys Tyr Val Gly
610                 615                 620

Thr Ala Gly Lys Val Ile Ala Ile Asp Gly Phe Gly Ala Ser Ala Pro
625                 630                 635                 640

Gly Asp Leu Val Val Glu Lys Tyr Gly Phe Thr Lys Glu Asn Ile Leu
                645                 650                 655

Asn Gln Val Met Ser Leu
                660

<210> SEQ ID NO 17
<211> LENGTH: 253
<212> TYPE: PRT
<213> ORGANISM: Staphylococcus aureus
```

```
<400> SEQUENCE: 17

Met Arg Thr Pro Ile Ile Ala Gly Asn Trp Lys Met Asn Lys Thr Val
1               5                   10                  15

Gln Glu Ala Lys Asp Phe Val Asn Ala Leu Pro Thr Leu Pro Asp Ser
            20                  25                  30

Lys Glu Val Glu Ser Val Ile Cys Ala Pro Ala Ile Gln Leu Asp Ala
        35                  40                  45

Leu Thr Thr Ala Val Lys Glu Gly Lys Ala Gln Gly Leu Glu Ile Gly
    50                  55                  60

Ala Gln Asn Thr Tyr Phe Glu Asp Asn Gly Ala Phe Thr Gly Glu Thr
65                  70                  75                  80

Ser Pro Val Ala Leu Ala Asp Leu Gly Val Lys Tyr Val Val Ile Gly
                85                  90                  95

His Ser Glu Arg Arg Glu Leu Phe His Glu Thr Asp Glu Glu Ile Asn
            100                 105                 110

Lys Lys Ala His Ala Ile Phe Lys His Gly Met Thr Pro Ile Ile Cys
        115                 120                 125

Val Gly Glu Thr Asp Glu Glu Arg Glu Ser Gly Lys Ala Asn Asp Val
    130                 135                 140

Val Gly Glu Gln Val Lys Lys Ala Val Ala Gly Leu Ser Glu Asp Gln
145                 150                 155                 160

Leu Lys Ser Val Val Ile Ala Tyr Glu Pro Ile Trp Ala Ile Gly Thr
                165                 170                 175

Gly Lys Ser Ser Thr Ser Glu Asp Ala Asn Glu Met Cys Ala Phe Val
            180                 185                 190

Arg Gln Thr Ile Ala Asp Leu Ser Ser Lys Glu Val Ser Glu Ala Thr
        195                 200                 205

Arg Ile Gln Tyr Gly Gly Ser Val Lys Pro Asn Asn Ile Lys Glu Tyr
    210                 215                 220

Met Ala Gln Thr Asp Ile Asp Gly Ala Leu Val Gly Gly Ala Ser Leu
225                 230                 235                 240

Lys Val Glu Asp Phe Val Gln Leu Leu Glu Gly Ala Lys
                245                 250

<210> SEQ ID NO 18
<211> LENGTH: 291
<212> TYPE: PRT
<213> ORGANISM: Staphylococcus aureus

<400> SEQUENCE: 18

Ala Val Tyr Ala Ser Arg Ala Asn Leu Lys Thr Val Met Ile Glu Arg
1               5                   10                  15

Gly Ile Pro Gly Gly Gln Met Ala Asn Thr Glu Glu Val Glu Asn Phe
            20                  25                  30

Pro Gly Phe Glu Met Ile Thr Gly Pro Asp Leu Ser Thr Lys Met Phe
        35                  40                  45

Glu His Ala Lys Lys Phe Gly Ala Val Tyr Gln Tyr Gly Asp Ile Lys
    50                  55                  60

Ser Val Glu Asp Lys Gly Glu Tyr Lys Val Ile Asn Phe Gly Asn Lys
65                  70                  75                  80

Glu Leu Thr Ala Lys Ala Val Ile Ile Ala Thr Gly Ala Glu Tyr Lys
                85                  90                  95

Lys Ile Gly Val Pro Gly Glu Gln Glu Leu Gly Gly Arg Gly Val Ser
            100                 105                 110

Tyr Cys Ala Val Cys Asp Gly Ala Phe Phe Lys Asn Lys Arg Leu Phe
```

```
                115                 120                 125
Val Ile Gly Gly Gly Asp Ser Ala Val Glu Glu Gly Thr Phe Leu Thr
        130                 135                 140

Lys Phe Ala Asp Lys Val Thr Ile Val His Arg Arg Asp Glu Leu Arg
145                 150                 155                 160

Ala Gln Arg Ile Leu Gln Asp Arg Ala Phe Lys Asn Asp Lys Ile Asp
                165                 170                 175

Phe Ile Trp Ser His Thr Leu Lys Ser Ile Asn Glu Lys Asp Gly Lys
            180                 185                 190

Val Gly Ser Val Thr Leu Thr Ser Thr Lys Asp Gly Ser Glu Glu Thr
        195                 200                 205

His Glu Ala Asp Gly Val Phe Ile Tyr Ile Gly Met Lys Pro Leu Thr
    210                 215                 220

Ala Pro Phe Lys Asp Leu Gly Ile Thr Asn Asp Val Gly Tyr Ile Val
225                 230                 235                 240

Thr Lys Asp Asp Met Thr Thr Ser Val Pro Gly Ile Phe Ala Ala Gly
                245                 250                 255

Asp Val Arg Asp Lys Gly Leu Arg Gln Ile Val Thr Ala Thr Gly Asp
            260                 265                 270

Gly Ser Ile Ala Ala Gln Ser Ala Glu Tyr Ile Glu His Leu Asn
        275                 280                 285

Asp Gln Ala
        290

<210> SEQ ID NO 19
<211> LENGTH: 412
<212> TYPE: PRT
<213> ORGANISM: Staphylococcus aureus

<400> SEQUENCE: 19

Met Ser Tyr Ile Thr Lys Gln Asp Lys Val Ile Ala Glu Ala Ile Glu
1               5                   10                  15

Arg Glu Phe Gln Arg Gln Asn Ser Asn Ile Glu Leu Ile Ala Ser Glu
                20                  25                  30

Asn Phe Val Ser Glu Ala Val Met Glu Ala Gln Gly Ser Val Leu Thr
            35                  40                  45

Asn Lys Tyr Ala Glu Gly Tyr Pro Gly Arg Arg Tyr Tyr Gly Gly Cys
        50                  55                  60

Glu Phe Val Asp Val Thr Glu Ser Ile Ala Ile Asp Arg Ala Lys Ala
65                  70                  75                  80

Leu Phe Gly Ala Glu His Val Asn Val Gln Pro His Ser Gly Ser Gln
                85                  90                  95

Ala Asn Met Ala Val Tyr Leu Val Ala Leu Glu Met Gly Asp Thr Val
            100                 105                 110

Leu Gly Met Asn Leu Ser His Gly Gly His Leu Thr His Gly Ala Pro
        115                 120                 125

Val Asn Phe Ser Gly Lys Phe Tyr Asn Phe Val Glu Tyr Gly Val Asp
    130                 135                 140

Lys Asp Thr Glu Arg Ile Asn Tyr Asp Glu Val Arg Lys Leu Ala Leu
145                 150                 155                 160

Glu His Lys Pro Lys Leu Ile Val Ala Gly Ala Ser Ala Tyr Ser Arg
                165                 170                 175

Thr Ile Asp Phe Lys Lys Phe Lys Glu Ile Ala Asp Glu Val Asn Ala
            180                 185                 190

Lys Leu Met Val Asp Met Ala His Ile Ala Gly Leu Val Ala Ala Gly
```

```
                    195                 200                 205
Leu His Pro Asn Pro Val Glu Tyr Ala Asp Phe Val Thr Thr Thr Thr
210                 215                 220

His Lys Thr Leu Arg Gly Pro Arg Gly Gly Met Ile Leu Cys Lys Glu
225                 230                 235                 240

Glu Tyr Lys Lys Asp Ile Asp Lys Thr Ile Phe Pro Gly Ile Gln Gly
                245                 250                 255

Gly Pro Leu Glu His Val Ile Ala Ala Lys Ala Val Ala Phe Gly Glu
                260                 265                 270

Ala Leu Glu Asn Asn Phe Lys Thr Tyr Gln Gln Gln Val Val Lys Asn
                275                 280                 285

Ala Lys Val Leu Ala Glu Ala Leu Ile Asn Glu Gly Phe Arg Ile Val
                290                 295                 300

Ser Gly Gly Thr Asp Asn His Leu Val Ala Val Asp Val Lys Gly Ser
305                 310                 315                 320

Ile Gly Leu Thr Gly Lys Glu Ala Glu Thr Leu Asp Ser Val Gly
                325                 330                 335

Ile Thr Cys Asn Lys Asn Thr Ile Pro Phe Asp Gln Glu Lys Pro Phe
                340                 345                 350

Val Thr Ser Gly Ile Arg Leu Gly Thr Pro Ala Ala Thr Thr Arg Gly
                355                 360                 365

Phe Asp Glu Lys Ala Phe Glu Val Ala Lys Ile Ile Ser Leu Ala
370                 375                 380

Leu Lys Asn Ser Lys Asp Glu Glu Lys Leu Gln Gln Ala Lys Glu Arg
385                 390                 395                 400

Val Ala Lys Leu Thr Ala Glu Tyr Pro Leu Tyr Gln
                405                 410

<210> SEQ ID NO 20
<211> LENGTH: 296
<212> TYPE: PRT
<213> ORGANISM: Staphylococcus aureus

<400> SEQUENCE: 20

Met Leu Leu Gly Ser His Val Ser Met Ser Gly Lys Lys Met Leu Glu
1               5                   10                  15

Gly Ser Ala Ile Glu Ala Tyr Glu Tyr Gly Glu Thr Thr Phe Met Ile
                20                  25                  30

Tyr Thr Gly Ala Pro Gln Asn Thr Arg Arg Lys Ser Ile Glu Asp Leu
            35                  40                  45

Asn Ile Thr Lys Gly His Glu Val Met Glu Lys Tyr Gly Leu Ser Asn
50                  55                  60

Ile Val Val His Ala Pro Tyr Ile Ile Asn Ile Ala Asn Thr Thr Lys
65                  70                  75                  80

Pro Glu Thr Phe Asn Leu Gly Val Asp Phe Leu Gln Gln Glu Ile Glu
                85                  90                  95

Arg Thr Gln Ala Ile Gly Ala Lys Asp Ile Val Leu His Pro Gly Ala
            100                 105                 110

His Val Gly Ala Gly Val Asp Ala Gly Ile Asn Lys Ile Ile Glu Gly
        115                 120                 125

Leu Asn Glu Val Leu Thr Asn Asp Asn Val Arg Ile Ala Leu Glu
        130                 135                 140

Thr Met Ala Gly Lys Gly Thr Glu Ile Gly Arg Ser Phe Glu Glu Leu
145                 150                 155                 160

Ala Arg Ile Ile Asp Gly Val His Asn Asn Glu Arg Leu Ser Val Cys
```

```
                       165                 170                 175
Phe Asp Thr Cys His Thr His Asp Ala Gly Tyr Asn Val Lys Glu Asp
            180                 185                 190

Phe Asp Gly Val Leu Asn Glu Phe Asp Lys Ile Ile Gly Val Asp Arg
        195                 200                 205

Ile Lys Val Val His Val Asn Asp Ser Lys Asn Asp Arg Gly Ala Gln
    210                 215                 220

Lys Asp Arg His Glu Asn Ile Gly Phe Gly Tyr Ile Gly Phe Asp Ala
225                 230                 235                 240

Leu Asn Tyr Ile Val His His Asp Ser Phe Lys Asp Ile Pro Lys Ile
                245                 250                 255

Leu Glu Thr Pro Tyr Val Gly Glu Asp Lys Lys Asn Lys Lys Pro Pro
            260                 265                 270

Tyr Lys Leu Glu Ile Glu Met Leu Lys Gln Gln Gln Phe Asp Pro Glu
        275                 280                 285

Leu Lys Asn Lys Val Met Gln Gln
    290                 295

<210> SEQ ID NO 21
<211> LENGTH: 318
<212> TYPE: PRT
<213> ORGANISM: Staphylococcus aureus

<400> SEQUENCE: 21

Met Tyr Asn Pro Phe Asp Glu Ala Tyr His Gly Leu Cys Glu Glu Ile
1               5                   10                  15

Leu Glu Ile Gly Asn Arg Arg Asp Asp Arg Thr His Thr Gly Thr Ile
            20                  25                  30

Ser Lys Phe Gly His Gln Leu Arg Phe Asp Leu Thr Lys Gly Phe Pro
        35                  40                  45

Leu Leu Thr Thr Lys Lys Val Ser Phe Lys Leu Val Ala Thr Glu Leu
    50                  55                  60

Leu Trp Phe Ile Lys Gly Asp Thr Asn Ile Gln Tyr Leu Leu Lys Tyr
65                  70                  75                  80

Asn Asn Asn Ile Trp Asn Glu Trp Ala Phe Glu Asn Tyr Val Gln Ser
                85                  90                  95

Asp Asp Tyr His Gly Pro Asp Met Thr Asp Phe Gly His Arg Ser Gln
            100                 105                 110

Gln Asp Pro Glu Phe Asn Glu Gln Tyr Lys Glu Glu Met Lys Lys Phe
        115                 120                 125

Lys Glu Arg Ile Leu Asn Asp Asp Ala Phe Ala Lys Lys Tyr Gly Asn
    130                 135                 140

Leu Gly Asn Val Tyr Gly Lys Gln Trp Arg Asp Trp Glu Asp Lys Asn
145                 150                 155                 160

Gly Asn His Tyr Asp Gln Leu Lys Ser Val Ile Gln Gln Ile Lys Thr
                165                 170                 175

Asn Pro Asn Ser Arg Arg His Ile Val Ser Ala Trp Asn Pro Thr Glu
            180                 185                 190

Ile Asp Ser Met Ala Leu Pro Pro Cys His Thr Met Phe Gln Phe Tyr
        195                 200                 205

Val Gln Glu Gly Lys Leu Asn Cys Gln Leu Tyr Gln Arg Ser Ala Asp
    210                 215                 220

Ile Phe Leu Gly Val Pro Phe Asn Ile Ala Ser Tyr Ala Leu Leu Thr
225                 230                 235                 240

His Leu Val Ala Lys Glu Cys Gly Leu Glu Val Gly Glu Phe Ile His
```

```
                    245                 250                 255
Thr Phe Gly Asp Ala His Ile Tyr Ser Asn His Met Asp Ala Ile His
            260                 265                 270

Thr Gln Leu Ser Arg Asp Ser Tyr Leu Pro Pro Gln Leu Lys Ile Asn
            275                 280                 285

Thr Asp Lys Ser Ile Phe Asp Ile Asn Tyr Glu Asp Leu Glu Leu Ile
            290                 295                 300

Asn Tyr Glu Ser His Pro Ala Ile Lys Ala Pro Ile Ala Val
305                 310                 315

<210> SEQ ID NO 22
<211> LENGTH: 238
<212> TYPE: PRT
<213> ORGANISM: Staphylococcus aureus

<400> SEQUENCE: 22

Met Lys Tyr Ala Gly Ile Leu Ala Gly Gly Ile Gly Ser Arg Met Gly
1               5                   10                  15

Asn Val Pro Leu Pro Lys Gln Phe Leu Asp Leu Asp Asn Lys Pro Ile
            20                  25                  30

Leu Ile His Thr Leu Glu Lys Phe Ile Leu Ile Asn Asp Phe Glu Lys
        35                  40                  45

Ile Ile Ile Ala Thr Pro Gln Gln Trp Met Thr His Thr Lys Asp Thr
50                  55                  60

Leu Arg Lys Phe Lys Ile Ser Asp Glu Arg Ile Glu Val Ile Gln Gly
65                  70                  75                  80

Gly Ser Asp Arg Asn Asp Thr Ile Met Asn Ile Val Lys His Ile Glu
                85                  90                  95

Ser Thr Asn Gly Ile Asn Asp Asp Val Ile Val Thr His Asp Ala
            100                 105                 110

Val Arg Pro Phe Leu Thr His Arg Ile Ile Lys Glu Asn Ile Gln Ala
            115                 120                 125

Ala Leu Glu Tyr Gly Ala Val Asp Thr Val Ile Asp Ala Ile Asp Thr
        130                 135                 140

Ile Val Thr Ser Lys Asp Asn Gln Thr Ile Asp Ala Ile Pro Val Arg
145                 150                 155                 160

Asn Glu Met Tyr Gln Gly Gln Thr Pro Gln Ser Phe Asn Ile Asn Leu
                165                 170                 175

Leu Lys Glu Ser Tyr Ala Gln Leu Ser Asp Glu Gln Lys Ser Ile Leu
            180                 185                 190

Ser Asp Ala Cys Lys Ile Ile Val Glu Thr Asn Lys Pro Val Arg Leu
        195                 200                 205

Val Lys Gly Glu Leu Tyr Asn Ile Lys Val Thr Thr Pro Tyr Asp Leu
    210                 215                 220

Lys Val Ala Asn Ala Ile Ile Arg Gly Gly Ile Ala Asp Asp
225                 230                 235

<210> SEQ ID NO 23
<211> LENGTH: 317
<212> TYPE: PRT
<213> ORGANISM: Staphylococcus aureus

<400> SEQUENCE: 23

Met Glu Lys Val Tyr Val Ala Gly Ala Ile Pro Glu Val Gly Leu Lys
1               5                   10                  15

Leu Leu Gln Glu His Phe Glu Val Glu Met Tyr Glu Gly Lys Gly Leu
            20                  25                  30
```

```
Val Asp Lys Asp Thr Leu Ile Lys Gly Val Lys Asn Ala Thr Ala Leu
            35                  40                  45

Ile Ser Leu Leu Ser Thr Asn Val Asp Lys Asp Val Ile Asp Ala Gly
 50                  55                  60

Lys Asp Leu Lys Ile Ile Ala Asn Tyr Gly Gly Phe Asn Asn Ile
 65                  70                  75                  80

Asp Ile Glu Tyr Ala Arg Glu Lys Ser Ile Asp Val Thr Asn Thr Pro
                     85                  90                  95

Lys Ala Ser Thr Asn Ala Thr Ala Asp Leu Thr Ile Gly Leu Val Leu
                    100                 105                 110

Ala Val Ala Arg Arg Ile Val Glu Gly Asp Gln Leu Ser Arg Thr Thr
                115                 120                 125

Gly Phe Asp Gly Trp Ala Pro Leu Phe Phe Arg Gly Arg Glu Val Ser
            130                 135                 140

Gly Lys Thr Ile Gly Ile Ile Gly Leu Gly Glu Ile Gly Ser Ala Val
145                 150                 155                 160

Ala Arg Arg Ala Arg Ala Phe Asp Met Asp Val Leu Tyr Thr Gly Pro
                165                 170                 175

Asn Arg Lys Glu Glu Lys Glu Arg Glu Ile Gly Ala Lys Tyr Val Asp
                180                 185                 190

Leu Asp Thr Leu Leu Lys Asn Ala Asp Phe Ile Thr Ile Asn Ala Ala
                195                 200                 205

Tyr Asn Pro Lys Met His His Leu Ile Asp Thr Glu Gln Phe Lys Met
                210                 215                 220

Met Lys Ser Thr Ala Tyr Leu Ile Asn Ala Ser Arg Gly Pro Ile Val
225                 230                 235                 240

His Glu Gln Ala Leu Val Gln Ala Leu Lys Asp Asn Glu Ile Glu Gly
                245                 250                 255

Ala Ala Leu Asp Val Tyr Glu Phe Glu Pro Asp Ile Thr Asp Asp Leu
                260                 265                 270

Lys Ser Leu Asn Asn Val Val Leu Thr Pro His Ile Gly Asn Ala Thr
                275                 280                 285

Phe Glu Ala Arg Asp Met Met Ser Lys Ile Val Ala Asn Ala Ala Ile
                290                 295                 300

Ser Ala Val Gln Gly Glu Lys Pro Gln Phe Val Val Asn
305                 310                 315

<210> SEQ ID NO 24
<211> LENGTH: 336
<212> TYPE: PRT
<213> ORGANISM: Staphylococcus aureus

<400> SEQUENCE: 24

Met Thr Glu Ile Gln Lys Pro Tyr Asp Leu Lys Gly Arg Ser Leu Leu
1               5                   10                  15

Lys Glu Ser Asp Phe Thr Lys Ala Glu Phe Glu Gly Leu Ile Asp Phe
                20                  25                  30

Ala Ile Thr Leu Lys Glu Tyr Lys Lys Asn Gly Ile Lys His His Tyr
            35                  40                  45

Leu Ser Gly Lys Asn Ile Ala Leu Leu Phe Glu Lys Asn Ser Thr Arg
 50                  55                  60

Thr Arg Ala Ala Phe Thr Val Ala Ser Ile Asp Leu Gly Ala His Pro
 65                  70                  75                  80

Glu Phe Leu Gly Lys Asn Asp Ile Gln Leu Gly Lys Lys Glu Ser Val
                85                  90                  95
```

Glu Asp Thr Ala Lys Val Leu Gly Arg Met Phe Asp Gly Ile Glu Phe
                100                 105                 110

Arg Gly Phe Ser Gln Gln Ala Val Glu Asp Leu Ala Lys Phe Ser Gly
            115                 120                 125

Val Pro Val Trp Asn Gly Leu Thr Asp Asp Trp His Pro Thr Gln Met
130                 135                 140

Leu Ala Asp Phe Met Thr Ile Lys Glu Asn Phe Gly Tyr Leu Glu Gly
145                 150                 155                 160

Ile Asn Leu Thr Tyr Val Gly Asp Gly Arg Asn Asn Ile Ala His Ser
                165                 170                 175

Leu Met Val Ala Gly Ala Met Leu Gly Val Asn Val Arg Ile Cys Thr
            180                 185                 190

Pro Lys Ser Leu Asn Pro Lys Glu Ala Tyr Val Asp Ile Ala Lys Glu
        195                 200                 205

Lys Ala Ser Gln Tyr Gly Gly Ser Ile Met Ile Thr Asp Asn Ile Ala
    210                 215                 220

Glu Ala Val Glu Asn Thr Asp Ala Ile Tyr Thr Asp Val Trp Val Ser
225                 230                 235                 240

Met Gly Glu Glu Ser Glu Phe Glu Gln Arg Ile Asn Leu Leu Lys Asp
                245                 250                 255

Tyr Gln Val Asn Gln Gln Met Phe Asp Leu Thr Gly Lys Asp Ser Thr
            260                 265                 270

Ile Phe Leu His Cys Leu Pro Ala Phe His Asp Thr Asn Thr Leu Tyr
        275                 280                 285

Gly Gln Glu Ile Tyr Glu Lys Tyr Gly Leu Ala Glu Met Glu Val Thr
    290                 295                 300

Asp Gln Ile Phe Arg Ser Glu His Ser Lys Val Phe Gln Ala Glu
305                 310                 315                 320

Asn Arg Met His Thr Ile Lys Ala Val Met Ala Ala Thr Leu Gly Ser
                325                 330                 335

<210> SEQ ID NO 25
<211> LENGTH: 336
<212> TYPE: PRT
<213> ORGANISM: Staphylococcus aureus

<400> SEQUENCE: 25

Met Arg Ala Ala Val Val Thr Lys Asp His Lys Val Ser Ile Glu Asp
1               5                   10                  15

Lys Lys Leu Arg Ala Leu Lys Pro Gly Glu Ala Leu Val Gln Thr Glu
            20                  25                  30

Tyr Cys Gly Val Cys His Thr Asp Leu His Val Lys Asn Ala Asp Phe
        35                  40                  45

Gly Asp Val Thr Gly Val Thr Leu Gly His Glu Gly Ile Gly Lys Val
    50                  55                  60

Ile Glu Val Ala Glu Asp Val Glu Ser Leu Lys Ile Gly Asp Arg Val
65                  70                  75                  80

Ser Ile Ala Trp Met Phe Glu Ser Cys Gly Arg Cys Glu Tyr Cys Thr
                85                  90                  95

Thr Gly Arg Glu Thr Leu Cys Arg Ser Val Lys Asn Ala Gly Tyr Thr
            100                 105                 110

Val Asp Gly Ala Met Ala Glu Gln Val Ile Val Thr Ala Asp Tyr Ala
        115                 120                 125

Val Lys Val Pro Glu Lys Leu Asp Pro Ala Ala Ala Ser Ser Ile Thr
    130                 135                 140

```
Cys Ala Gly Val Thr Thr Tyr Lys Ala Val Lys Val Ser Asn Val Lys
145                 150                 155                 160

Pro Gly Gln Trp Leu Gly Val Phe Gly Ile Gly Leu Gly Asn Leu
            165                 170                 175

Ala Leu Gln Tyr Ala Lys Asn Val Met Gly Ala Lys Ile Val Ala Phe
            180                 185                 190

Asp Ile Asn Asp Asp Lys Leu Ala Phe Ala Lys Glu Leu Gly Ala Asp
                195                 200                 205

Ala Ile Ile Asn Ser Lys Asp Val Asp Pro Val Ala Glu Val Met Lys
            210                 215                 220

Leu Thr Asp Asn Lys Gly Leu Asp Ala Thr Val Val Thr Ser Val Ala
225                 230                 235                 240

Lys Thr Pro Phe Asn Gln Ala Val Asp Val Lys Ala Gly Ala Arg
                245                 250                 255

Val Val Ala Val Gly Leu Pro Val Asp Lys Met Asn Leu Asp Ile Pro
            260                 265                 270

Arg Leu Val Leu Asp Gly Ile Glu Val Val Gly Ser Leu Val Gly Thr
            275                 280                 285

Arg Gln Asp Leu Arg Glu Ala Phe Glu Phe Ala Ala Glu Asn Lys Val
290                 295                 300

Thr Pro Lys Val Gln Leu Arg Lys Leu Glu Glu Ile Asn Asp Ile Phe
305                 310                 315                 320

Glu Glu Met Glu Asn Gly Thr Ile Thr Gly Arg Met Val Ile Lys Phe
                325                 330                 335

<210> SEQ ID NO 26
<211> LENGTH: 281
<212> TYPE: PRT
<213> ORGANISM: Staphylococcus haemolyticus

<400> SEQUENCE: 26

Met Lys Lys Leu Ile Phe Leu Ile Val Ile Ala Leu Val Leu Ser Ala
1               5                   10                  15

Cys Asn Ser Asn Ser Ser His Ala Lys Glu Leu Asn Asp Leu Glu Lys
            20                  25                  30

Lys Tyr Asn Ala His Ile Gly Val Tyr Ala Leu Asp Thr Lys Ser Gly
        35                  40                  45

Lys Glu Val Lys Phe Asn Ser Asp Lys Arg Phe Ala Tyr Ala Ser Thr
    50                  55                  60

Ser Lys Ala Ile Asn Ser Ala Ile Leu Leu Glu Gln Val Pro Tyr Asn
65                  70                  75                  80

Lys Leu Asn Lys Lys Val His Ile Asn Lys Asp Asp Ile Val Ala Tyr
                85                  90                  95

Ser Pro Ile Leu Glu Lys Tyr Val Gly Lys Asp Ile Thr Leu Lys Ala
            100                 105                 110

Leu Ile Glu Ala Ser Met Thr Tyr Ser Asp Asn Thr Ala Asn Asn Lys
        115                 120                 125

Ile Ile Lys Glu Ile Gly Gly Ile Lys Lys Val Lys Gln Arg Leu Lys
    130                 135                 140

Glu Leu Gly Asp Lys Val Thr Asn Pro Val Arg Tyr Glu Ile Glu Leu
145                 150                 155                 160

Asn Tyr Tyr Ser Pro Lys Ser Lys Asp Thr Ser Thr Pro Ala Ala
                165                 170                 175

Phe Gly Lys Thr Leu Asn Lys Leu Ile Ala Asn Gly Lys Leu Ser Lys
            180                 185                 190
```

```
Glu Asn Lys Lys Phe Leu Leu Asp Leu Met Leu Asn Asn Lys Ser Gly
            195                 200                 205

Asp Thr Leu Ile Lys Asp Gly Val Pro Lys Asp Tyr Lys Val Ala Asp
            210                 215                 220

Lys Ser Gly Gln Ala Ile Thr Tyr Ala Ser Arg Asn Asp Val Ala Phe
225                 230                 235                 240

Val Tyr Pro Lys Gly Gln Ser Glu Pro Ile Val Leu Val Ile Phe Thr
            245                 250                 255

Asn Lys Asp Asn Lys Ser Asp Lys Pro Asn Asp Lys Leu Ile Ser Glu
            260                 265                 270

Thr Ala Lys Ser Val Met Lys Glu Phe
            275                 280

<210> SEQ ID NO 27
<211> LENGTH: 140
<212> TYPE: PRT
<213> ORGANISM: Staphylococcus aureus

<400> SEQUENCE: 27

Met Ala Ile His Tyr Glu Thr Lys Ala Thr Asn Val Gly Gly Arg Lys
1               5                   10                  15

Gly His Val Tyr Thr Asp Asp Arg Ala Leu Asp Ile Asp Ile Val Pro
            20                  25                  30

Pro Ala Gln Ala Asp Gly Lys Ala Thr Asn Pro Glu Gln Leu Phe Ala
        35                  40                  45

Ala Gly Tyr Ala Ser Cys Phe Asn Gly Ala Phe Asp Leu Ile Leu Lys
    50                  55                  60

Gln Asn Lys Val Arg Asp Ala His Pro Glu Val Thr Leu Thr Val Arg
65                  70                  75                  80

Leu Glu Asp Asp Ser Asp Ser Glu Ser Pro Lys Leu Ser Val Ser Ile
                85                  90                  95

Asp Ala Thr Ile Lys Asn Val Ile Ser Gln Glu Ala Glu Lys Tyr
            100                 105                 110

Leu Gln Met Ala His Glu Phe Cys Pro Tyr Ser Lys Ala Thr Gln Gly
            115                 120                 125

Asn Ile Asn Val Asp Leu Asn Val Asn Val Val Asp
            130                 135                 140

<210> SEQ ID NO 28
<211> LENGTH: 224
<212> TYPE: PRT
<213> ORGANISM: Staphylococcus aureus

<400> SEQUENCE: 28

Met Ile Asn Lys Asn Asp Ile Val Ala Asp Val Val Thr Asp Tyr Pro
1               5                   10                  15

Lys Ala Ala Asp Ile Phe Arg Ser Val Gly Ile Asp Phe Cys Cys Gly
            20                  25                  30

Gly Gln Val Ser Ile Glu Ala Ala Ala Leu Gly Lys Lys Asn Val Asp
        35                  40                  45

Leu Asn Glu Leu Leu Gln Arg Leu Asn Asp Val Asn Lys Thr Asn Thr
    50                  55                  60

Pro Gly Ser Leu Asn Pro Lys Phe Leu Asn Val Ser Ser Leu Ile Gln
65                  70                  75                  80

Tyr Ile Gln Ser Ala Tyr His Glu Pro Leu Arg Glu Glu Phe Lys Asn
                85                  90                  95
```

```
Leu Thr Pro Tyr Val Thr Lys Leu Ser Lys Val His Gly Pro Asn His
                100                 105                 110

Pro Tyr Leu Val Glu Leu Lys Glu Thr Tyr Asp Thr Phe Lys Asn Gly
            115                 120                 125

Met Leu Glu His Met Gln Lys Glu Asp Val Asp Phe Pro Lys Leu
130                 135                 140

Ile Lys Tyr Glu Gln Gly Glu Val Val Asp Asp Ile Asn Thr Val Ile
145                 150                 155                 160

Asp Asp Leu Val Ser Asp His Ile Ala Thr Gly Glu Leu Leu Val Lys
                165                 170                 175

Met Ser Glu Leu Thr Ser Ser Tyr Glu Pro Pro Ile Glu Ala Cys Gly
            180                 185                 190

Thr Trp Arg Leu Val Tyr Gln Arg Leu Lys Ala Leu Glu Val Leu Thr
        195                 200                 205

His Glu His Val His Leu Glu Asn His Val Leu Phe Lys Lys Val Ser
    210                 215                 220

<210> SEQ ID NO 29
<211> LENGTH: 183
<212> TYPE: PRT
<213> ORGANISM: Staphylococcus aureus

<400> SEQUENCE: 29

Met Leu Thr Met Lys Asp Ile Ile Arg Asp Gly His Pro Thr Leu Arg
1               5                   10                  15

Gln Lys Ala Ala Glu Leu Glu Leu Pro Leu Thr Lys Glu Gly Lys Glu
            20                  25                  30

Thr Leu Ile Ala Met Arg Glu Phe Leu Val Asn Ser Gln Asp Glu Glu
        35                  40                  45

Ile Ala Lys Arg Tyr Gly Leu Arg Ser Gly Val Gly Leu Ala Ala Pro
    50                  55                  60

Gln Ile Asn Ile Ser Lys Arg Met Ile Ala Val Leu Ile Pro Asp Asp
65                  70                  75                  80

Gly Ser Gly Lys Ser Tyr Asp Tyr Met Leu Val Asn Pro Lys Ile Val
                85                  90                  95

Ser His Ser Val Gln Glu Ala Tyr Leu Pro Thr Gly Glu Gly Cys Leu
            100                 105                 110

Ser Val Asp Asp Asn Val Ala Gly Leu Val His Arg His Asn Arg Ile
        115                 120                 125

Thr Ile Lys Ala Lys Asp Ile Glu Gly Asn Asp Ile Gln Leu Arg Leu
    130                 135                 140

Lys Gly Tyr Pro Ala Ile Val Phe Gln His Glu Ile Asp His Leu Asn
145                 150                 155                 160

Gly Val Met Phe Tyr Asp His Ile Asp Lys Asp His Pro Leu Gln Pro
                165                 170                 175

His Thr Asp Ala Val Glu Val
            180

<210> SEQ ID NO 30
<211> LENGTH: 346
<212> TYPE: PRT
<213> ORGANISM: Staphylococcus aureus

<400> SEQUENCE: 30

Met Thr Thr Asn Thr Val Thr Leu Gln Thr Ala His Ile Val Ser Leu
1               5                   10                  15

Gly Asp Ile Glu Glu Ala Lys Ala Ser Ile Lys Pro Phe Ile Arg Arg
```

```
                        20                  25                  30
Thr Pro Leu Ile Lys Ser Met Tyr Leu Ser Gln Ser Ile Thr Lys Gly
            35                  40                  45

Asn Val Phe Leu Lys Leu Glu Asn Met Gln Phe Thr Gly Ser Phe Lys
        50                  55                  60

Phe Arg Gly Ala Ser Asn Lys Ile Asn His Leu Thr Asp Glu Gln Lys
 65                  70                  75                  80

Glu Lys Gly Ile Ile Ala Ser Ala Gly Asn His Ala Gln Gly Val
                85                  90                  95

Ala Leu Thr Ala Lys Leu Leu Gly Ile Asp Ala Thr Ile Val Met Pro
            100                 105                 110

Glu Thr Ala Pro Gln Ala Lys Gln Gln Ala Thr Lys Gly Tyr Gly Ala
        115                 120                 125

Lys Val Ile Leu Lys Gly Lys Asn Phe Asn Glu Thr Arg Leu Tyr Met
            130                 135                 140

Glu Glu Leu Ala Lys Glu Asn Gly Met Thr Ile Val His Pro Tyr Asp
145                 150                 155                 160

Asp Lys Phe Val Met Ala Gly Gln Gly Thr Ile Gly Leu Glu Ile Leu
                165                 170                 175

Asp Asp Ile Trp Asn Val Asn Thr Val Ile Val Pro Val Gly Gly Gly
            180                 185                 190

Gly Leu Ile Ala Gly Ile Ala Thr Ala Leu Lys Ser Phe Asn Pro Ser
        195                 200                 205

Ile His Ile Ile Gly Val Gln Ser Glu Asn Val His Gly Met Ala Glu
            210                 215                 220

Ser Phe Tyr Lys Arg Asp Leu Thr Glu His Arg Val Asp Ser Thr Ile
225                 230                 235                 240

Ala Asp Gly Cys Asp Val Lys Val Pro Gly Glu Gln Thr Tyr Glu Val
                245                 250                 255

Val Lys His Leu Val Asp Glu Phe Ile Leu Val Thr Glu Glu Glu Ile
            260                 265                 270

Glu His Ala Met Lys Asp Leu Met Gln Arg Ala Lys Ile Ile Thr Glu
        275                 280                 285

Gly Ala Gly Ala Leu Pro Thr Ala Ala Ile Leu Ser Gly Lys Ile Asn
    290                 295                 300

Asn Lys Trp Leu Glu Asp Lys Asn Val Val Ala Leu Val Ser Gly Gly
305                 310                 315                 320

Asn Val Asp Leu Thr Arg Val Ser Gly Val Ile Glu His Gly Leu Asn
                325                 330                 335

Ile Ala Asp Thr Ser Lys Gly Val Val Gly
            340                 345

<210> SEQ ID NO 31
<211> LENGTH: 372
<212> TYPE: PRT
<213> ORGANISM: Staphylococcus aureus

<400> SEQUENCE: 31

Met Lys Ile Gly Ile Pro Arg Glu Ile Lys Asn Asn Glu Asn Arg Val
 1               5                  10                  15

Gly Leu Ser Pro Ser Gly Val His Ala Leu Val Glu Ser Gly His Thr
                20                  25                  30

Val Leu Val Glu Thr Asn Ala Gly Ser Gly Ser Phe Phe Glu Asp Val
            35                  40                  45

Asp Tyr Lys Glu Ala Gly Ala Glu Ile Val Ala Glu Gln Ala Lys Val
```

```
                    50                  55                  60
Trp Asp Val Asp Met Val Ile Lys Val Lys Glu Pro Leu Ser Glu
 65                  70                  75                  80

Tyr Pro Tyr Phe Lys Glu Gly Leu Val Leu Phe Thr Tyr Leu His Leu
                     85                  90                  95

Ala Asn Glu Glu Lys Leu Thr Gln Ala Leu Ile Asp Arg Lys Val Ile
                    100                 105                 110

Ser Ile Ala Tyr Glu Thr Val Gln Leu Pro Asp Arg Ser Leu Pro Leu
                115                 120                 125

Leu Ser Pro Met Ser Glu Val Ala Gly Arg Met Ser Ala Gln Val Gly
    130                 135                 140

Ala Glu Phe Leu Gln Lys Leu Asn Gly Met Gly Ile Leu Leu Gly
145                 150                 155                 160

Gly Val Pro Gly Val Pro Lys Gly Lys Val Thr Ile Ile Gly Gly Gly
                    165                 170                 175

Gln Ala Gly Thr Asn Ala Ala Lys Ile Ala Leu Gly Leu Gly Ala Asp
                180                 185                 190

Val Thr Ile Leu Asp Val Asn Pro Lys Arg Leu Gln Gln Leu Asp Asp
            195                 200                 205

Leu Phe Gly Gly Arg Val His Thr Ile Met Ser Asn Pro Leu Asn Ile
210                 215                 220

Glu Leu Tyr Val Lys Gln Ser Asp Leu Val Ile Gly Ala Val Leu Ile
225                 230                 235                 240

Pro Gly Ala Lys Ala Pro Arg Leu Val Thr Glu Asp Met Ile Lys Gln
                    245                 250                 255

Met Lys Asn Gly Ser Val Ile Ile Asp Ile Ala Ile Asp Gln Gly Gly
                260                 265                 270

Ile Phe Glu Thr Thr Asp Lys Ile Thr Thr His Asp Pro Thr Tyr
            275                 280                 285

Ile Lys His Gly Val Val His Tyr Ala Val Ala Asn Met Pro Gly Ala
            290                 295                 300

Val Pro Arg Thr Ser Thr Leu Ala Leu Asn Asn Ala Thr Leu Pro Tyr
305                 310                 315                 320

Ala Leu Met Leu Ala Asn Lys Gly Tyr Arg Glu Ala Phe Lys Ser Asn
                    325                 330                 335

Gln Pro Leu Ser Leu Gly Leu Asn Thr Tyr Lys Gly His Val Thr Asn
                340                 345                 350

Lys Gly Val Ala Glu Ala Phe Glu Met Glu Tyr Lys Ser Val Glu Glu
            355                 360                 365

Ala Leu Gln Leu
    370

<210> SEQ ID NO 32
<211> LENGTH: 491
<212> TYPE: PRT
<213> ORGANISM: Staphylococcus aureus

<400> SEQUENCE: 32

Met Asn Phe Lys Leu Asn Asn Thr Leu Ser Asn Glu Ile Asn Thr Leu
 1               5                  10                  15

Ile Ile Gly Ile Pro Glu His Leu Asn Gln Leu Glu Arg Ile Ser Phe
                20                  25                  30

Asn His Ile Asp Ile Thr Glu Ser Leu Glu Arg Leu Lys His Gln His
            35                  40                  45

Ile Ile Gly Ser Lys Val Gly Lys Ile Tyr Thr Thr Ala Phe Asp Val
```

```
                50                  55                  60
Gln Asp Gln Thr Tyr Arg Leu Ile Thr Val Gly Leu Gly Asn Leu Lys
 65                  70                  75                  80

Ala Arg Ser Tyr Gln Asp Met Leu Lys Ile Trp Gly His Leu Phe Gln
                     85                  90                  95

Tyr Ile Lys Ser Glu His Ile Glu Asp Thr Tyr Leu Leu Met Asp Ser
                100                 105                 110

Phe Ile Ser Lys Tyr Asp Gln Leu Ser Asp Val Leu Met Ala Cys Gly
                115                 120                 125

Ile Gln Ser Glu Arg Ala Thr Tyr Glu Phe Asp His Tyr Lys Ser Ser
130                 135                 140

Lys Lys Ala Pro Phe Lys Thr Asn Leu Asn Leu Ile Ser Glu Ser Leu
145                 150                 155                 160

Ile Glu Leu Asp Phe Ile His Glu Gly Ile Ser Ile Gly Gln Ser Ile
                165                 170                 175

Asn Leu Ala Arg Asp Phe Ser Asn Met Pro Pro Asn Val Leu Thr Pro
                180                 185                 190

Gln Thr Phe Ala Glu Asp Ile Val Asn His Phe Lys Asn Thr Lys Val
                195                 200                 205

Lys Val Asp Val Lys Asp Tyr Asp Thr Leu Val Ser Glu Gly Phe Gly
210                 215                 220

Leu Leu Gln Ala Val Gly Lys Gly Ser Lys His Lys Pro Arg Leu Val
225                 230                 235                 240

Thr Ile Thr Tyr Asn Gly Lys Asp Lys Asp Val Ala Pro Ile Ala Leu
                245                 250                 255

Val Gly Lys Gly Ile Thr Tyr Asp Ser Gly Gly Tyr Ser Ile Lys Thr
                260                 265                 270

Lys Asn Gly Met Ala Thr Met Lys Phe Asp Met Cys Gly Ala Ala Asn
                275                 280                 285

Val Val Gly Ile Ile Glu Ala Ala Ser Arg Leu Gln Leu Pro Val Asn
290                 295                 300

Ile Val Gly Val Leu Ala Cys Ala Glu Asn Met Ile Asn Glu Ala Ser
305                 310                 315                 320

Met Lys Pro Asp Asp Val Phe Thr Ala Leu Ser Gly Glu Thr Val Glu
                325                 330                 335

Val Met Asn Thr Asp Ala Glu Gly Arg Leu Val Leu Ala Asp Ala Val
                340                 345                 350

Tyr Tyr Ala Asn Gln Tyr Gln Pro Ser Val Ile Met Asp Phe Ala Thr
                355                 360                 365

Leu Thr Gly Ala Ala Ile Val Ala Leu Gly Asp Asp Lys Ala Ala Ala
370                 375                 380

Phe Glu Ser Asn Ser Lys Val Ile Leu Asn Asp Ile Leu Gln Ile Ser
385                 390                 395                 400

Ser Lys Val Asp Glu Met Val Phe Glu Leu Pro Ile Thr Ala Thr Glu
                405                 410                 415

Arg Ala Ser Ile Asn His Ser Asp Ile Ala Asp Leu Val Asn His Thr
                420                 425                 430

Asn Gly Gln Gly Lys Ala Leu Phe Ala Ala Ser Phe Val Thr His Phe
                435                 440                 445

Ser Gly Gln Thr Pro His Ile His Phe Asp Ile Ala Gly Pro Ala Thr
                450                 455                 460

Thr Asn Lys Ala Ser Tyr Asn Gly Pro Lys Gly Pro Thr Gly Phe Met
465                 470                 475                 480
```

```
Ile Pro Thr Ile Val Gln Trp Leu Lys Gln Gln
                485                 490
```

<210> SEQ ID NO 33
<211> LENGTH: 555
<212> TYPE: PRT
<213> ORGANISM: Staphylococcus aureus

<400> SEQUENCE: 33

```
Met Thr His Leu Ser Asp Leu Asp Ile Ala Asn Gln Ser Thr Leu Gln
1               5                   10                  15

Pro Ile Lys Asp Ile Ala Ala Ser Val Gly Ile Ser Glu Asp Ala Leu
            20                  25                  30

Glu Pro Tyr Gly His Tyr Lys Ala Lys Ile Asp Ile Asn Lys Ile Thr
        35                  40                  45

Pro Arg Glu Asn Lys Gly Lys Val Val Leu Val Thr Ala Met Ser Pro
50                  55                  60

Thr Pro Ala Gly Glu Gly Lys Ser Thr Val Thr Val Gly Leu Ala Asp
65                  70                  75                  80

Ala Phe His Glu Leu Asn Lys Asn Val Met Val Ala Leu Arg Glu Pro
                85                  90                  95

Ala Leu Gly Pro Thr Phe Gly Ile Lys Gly Gly Ala Thr Gly Gly Gly
            100                 105                 110

Tyr Ala Gln Val Leu Pro Met Glu Asp Ile Asn Leu His Phe Asn Gly
        115                 120                 125

Asp Phe His Ala Ile Thr Thr Ala Asn Asn Ala Leu Ser Ala Phe Ile
    130                 135                 140

Asp Asn His Ile His Gln Gly Asn Glu Leu Gly Ile Asp Gln Arg Arg
145                 150                 155                 160

Ile Glu Trp Lys Arg Val Leu Asp Met Asn Asp Arg Ala Leu Arg His
                165                 170                 175

Val Asn Val Gly Leu Gly Gly Pro Thr Asn Gly Val Pro Arg Glu Asp
            180                 185                 190

Gly Phe Asn Ile Thr Val Ala Ser Glu Ile Met Ala Ile Leu Cys Leu
        195                 200                 205

Ser Arg Ser Ile Lys Asp Leu Lys Asp Lys Ile Ser Arg Ile Thr Ile
    210                 215                 220

Gly Tyr Thr Arg Asp Arg Lys Pro Val Thr Val Ala Asp Leu Lys Val
225                 230                 235                 240

Gln Gly Ala Leu Ala Met Ile Leu Lys Asp Ala Ile Lys Pro Asn Leu
                245                 250                 255

Val Gln Ser Ile Glu Gly Thr Pro Ala Leu Val His Gly Gly Pro Phe
            260                 265                 270

Ala Asn Ile Ala His Gly Cys Asn Ser Ile Leu Ala Thr Glu Thr Ala
        275                 280                 285

Arg Asp Leu Ala Asp Ile Val Val Thr Glu Ala Gly Phe Gly Ser Asp
    290                 295                 300

Leu Gly Ala Glu Lys Phe Met Asp Ile Lys Ala Arg Glu Ala Gly Phe
305                 310                 315                 320

Asp Pro Ala Ala Val Val Val Ala Thr Ile Arg Ala Leu Lys Met
                325                 330                 335

His Gly Gly Val Ala Lys Asp Asn Leu Lys Glu Glu Asn Val Glu Ala
            340                 345                 350

Val Lys Ala Gly Ile Val Asn Leu Glu Arg His Val Asn Asn Ile Lys
        355                 360                 365
```

```
Lys Phe Gly Val Glu Pro Val Val Ala Ile Asn Ala Phe Ile His Asp
            370                 375                 380

Thr Asp Ala Glu Val Glu Tyr Val Lys Ser Trp Ala Lys Glu Asn Asn
385                 390                 395                 400

Val Arg Ile Ala Leu Thr Glu Val Trp Glu Lys Gly Lys Gly Lys Gly
                405                 410                 415

Val Asp Leu Ala Asn Glu Val Leu Glu Val Ile Asp Gln Pro Asn Ser
            420                 425                 430

Phe Lys Pro Leu Tyr Glu Leu Glu Leu Pro Leu Glu Gln Lys Ile Glu
                435                 440                 445

Lys Ile Val Thr Glu Ile Tyr Gly Gly Ser Lys Val Thr Phe Ser Ser
450                 455                 460

Lys Ala Gln Lys Gln Leu Lys Gln Phe Lys Glu Asn Gly Trp Asp Asn
465                 470                 475                 480

Tyr Pro Val Cys Met Ala Lys Thr Gln Tyr Ser Phe Ser Asp Asp Gln
                485                 490                 495

Thr Leu Leu Gly Ala Pro Ser Gly Phe Glu Ile Thr Ile Arg Glu Leu
                500                 505                 510

Glu Ala Lys Thr Gly Ala Gly Phe Ile Val Ala Leu Thr Gly Ala Ile
            515                 520                 525

Met Thr Met Pro Gly Leu Pro Lys Lys Pro Ala Ala Leu Asn Met Asp
530                 535                 540

Val Thr Asp Asp Gly His Ala Ile Gly Leu Phe
545                 550                 555

<210> SEQ ID NO 34
<211> LENGTH: 322
<212> TYPE: PRT
<213> ORGANISM: Staphylococcus aureus

<400> SEQUENCE: 34

Met Lys Lys Ile Ala Val Leu Thr Ser Gly Gly Asp Ser Pro Gly Met
1               5                   10                  15

Asn Ala Ala Val Arg Ala Val Val Arg Thr Ala Ile Tyr Asn Glu Ile
            20                  25                  30

Glu Val Tyr Gly Val Tyr His Gly Tyr Gln Gly Leu Leu Asn Asp Asp
        35                  40                  45

Ile His Lys Leu Glu Leu Gly Ser Val Gly Asp Thr Ile Gln Arg Gly
    50                  55                  60

Gly Thr Phe Leu Tyr Ser Ala Arg Cys Pro Glu Phe Lys Glu Gln Glu
65                  70                  75                  80

Val Arg Lys Val Ala Ile Glu Asn Leu Arg Lys Arg Gly Ile Glu Gly
                85                  90                  95

Leu Val Val Ile Gly Gly Asp Gly Ser Tyr Arg Gly Ala Gln Arg Ile
            100                 105                 110

Ser Glu Glu Cys Lys Glu Ile Gln Thr Ile Gly Ile Pro Gly Thr Ile
        115                 120                 125

Asp Asn Asp Ile Asn Gly Thr Asp Phe Thr Ile Gly Phe Asp Thr Ala
    130                 135                 140

Leu Asn Thr Ile Ile Gly Leu Val Asp Lys Ile Arg Asp Thr Ala Ser
145                 150                 155                 160

Ser His Ala Arg Thr Phe Ile Ile Glu Ala Met Gly Arg Asp Cys Gly
                165                 170                 175

Asp Leu Ala Leu Trp Ala Gly Leu Ser Val Gly Ala Glu Thr Ile Val
            180                 185                 190
```

```
Val Pro Glu Val Lys Thr Asp Ile Lys Glu Ile Ala Asp Lys Ile Glu
        195                 200                 205

Gln Gly Ile Lys Arg Gly Lys Lys His Ser Ile Val Leu Val Ala Glu
        210                 215                 220

Gly Cys Met Thr Ala Gln Asp Cys Gln Lys Glu Leu Ser Gln Tyr Ile
225                 230                 235                 240

Asn Val Asp Asn Arg Val Ser Val Leu Gly His Val Gln Arg Gly Gly
                245                 250                 255

Ser Pro Thr Gly Ala Asp Arg Val Leu Ala Ser Arg Leu Gly Gly Tyr
                260                 265                 270

Ala Val Asp Leu Leu Met Gln Gly Glu Thr Ala Lys Gly Val Gly Ile
        275                 280                 285

Lys Asn Asn Lys Ile Val Ala Thr Ser Phe Asp Glu Ile Phe Asp Gly
290                 295                 300

Lys Asp His Lys Phe Asp Tyr Ser Leu Tyr Glu Leu Ala Asn Lys Leu
305                 310                 315                 320

Ser Ile

<210> SEQ ID NO 35
<211> LENGTH: 422
<212> TYPE: PRT
<213> ORGANISM: Staphylococcus aureus

<400> SEQUENCE: 35

Met Pro Glu Val Lys Val Pro Glu Leu Ala Glu Ser Ile Thr Glu Gly
1               5                   10                  15

Thr Ile Ala Glu Trp Leu Lys Asn Val Gly Asp Ser Val Glu Lys Gly
            20                  25                  30

Glu Ala Ile Leu Glu Leu Glu Thr Asp Lys Val Asn Val Glu Val Val
        35                  40                  45

Ser Glu Glu Ala Gly Val Leu Ser Glu Gln Leu Ala Ser Glu Gly Asp
    50                  55                  60

Thr Val Glu Val Gly Gln Ala Ile Ala Ile Gly Glu Gly Ser Gly
65                  70                  75                  80

Asn Ala Ser Lys Glu Asn Ser Asn Asp Asn Thr Pro Gln Gln Asn Glu
                85                  90                  95

Glu Thr Asn Asn Lys Lys Glu Val Thr Thr Asn Asn Ser Val Asp Lys
            100                 105                 110

Ala Glu Val Asn Gln Ala Asn Asp Asn Gln Gln Arg Ile Asn Ala
        115                 120                 125

Thr Pro Ser Ala Arg Arg Tyr Ala Arg Glu Asn Gly Val Asn Leu Ala
    130                 135                 140

Glu Val Ser Pro Lys Thr Asn Asp Val Val Arg Lys Glu Asp Ile Asp
145                 150                 155                 160

Lys Lys Gln Gln Ala Pro Ala Ser Thr Gln Thr Thr Gln Ala Pro
                165                 170                 175

Ala Lys Glu Glu Lys Lys Tyr Asn Gln Tyr Pro Thr Lys Pro Val Ile
            180                 185                 190

Arg Glu Lys Met Ser Arg Arg Lys Thr Ala Ala Lys Lys Leu Leu
        195                 200                 205

Glu Val Ser Asn Asn Thr Ala Met Leu Thr Thr Phe Asn Glu Val Asp
    210                 215                 220

Met Thr Asn Val Met Glu Leu Arg Lys Arg Lys Glu Gln Phe Met
225                 230                 235                 240

Lys Asp His Asp Gly Thr Lys Leu Gly Phe Met Ser Phe Phe Thr Lys
```

```
                    245                 250                 255
Ala Ser Val Ala Ala Leu Lys Lys Tyr Pro Glu Val Asn Ala Glu Ile
                260                 265                 270

Asp Gly Asp Asp Met Ile Thr Lys Gln Tyr Tyr Asp Ile Gly Val Ala
            275                 280                 285

Val Ser Thr Asp Asp Gly Leu Leu Val Pro Phe Val Arg Asp Cys Asp
        290                 295                 300

Lys Lys Asn Phe Ala Glu Ile Glu Ala Glu Ile Ala Asn Leu Ala Val
305                 310                 315                 320

Lys Ala Arg Glu Lys Lys Leu Gly Leu Asp Asp Met Val Asn Gly Ser
                325                 330                 335

Phe Thr Ile Thr Asn Gly Gly Ile Phe Gly Ser Met Met Ser Thr Pro
            340                 345                 350

Ile Ile Asn Gly Asn Gln Ala Ala Ile Leu Gly Met His Ser Ile Ile
        355                 360                 365

Thr Arg Pro Ile Ala Ile Asp Gln Asp Thr Ile Glu Asn Arg Pro Met
370                 375                 380

Met Tyr Ile Ala Leu Ser Tyr Asp His Arg Ile Ile Asp Gly Lys Glu
385                 390                 395                 400

Ala Val Gly Phe Leu Lys Thr Ile Lys Glu Leu Ile Glu Asn Pro Glu
                405                 410                 415

Asp Leu Leu Leu Glu Ser
            420

<210> SEQ ID NO 36
<211> LENGTH: 488
<212> TYPE: PRT
<213> ORGANISM: Staphylococcus aureus

<400> SEQUENCE: 36

Met Trp Glu Ser Lys Phe Ala Lys Glu Ser Leu Thr Phe Asp Asp Val
1               5                   10                  15

Leu Leu Ile Pro Ala Gln Ser Asp Ile Leu Pro Lys Asp Val Asp Leu
            20                  25                  30

Ser Val Gln Leu Ser Asp Lys Ala Lys Leu Asn Ile Pro Val Ile Ser
        35                  40                  45

Ala Gly Met Asp Thr Val Thr Glu Ser Lys Met Ala Ile Ala Met Ala
    50                  55                  60

Arg Gln Gly Gly Leu Gly Val Ile His Lys Asn Met Gly Val Glu Glu
65                  70                  75                  80

Gln Ala Asp Glu Val Gln Lys Val Lys Arg Ser Glu Asn Gly Val Ile
                85                  90                  95

Ser Asn Pro Phe Phe Leu Thr Pro Glu Glu Ser Val Tyr Glu Ala Glu
            100                 105                 110

Ala Leu Met Gly Lys Tyr Arg Ile Ser Gly Val Pro Ile Val Asp Asn
        115                 120                 125

Lys Glu Asp Arg Asn Leu Val Gly Ile Leu Thr Asn Arg Asp Leu Arg
    130                 135                 140

Phe Ile Glu Asp Phe Ser Ile Lys Ile Val Asp Val Met Thr Gln Glu
145                 150                 155                 160

Asn Leu Ile Thr Ala Pro Val Asn Thr Thr Leu Glu Glu Ala Glu Lys
                165                 170                 175

Ile Leu Gln Lys His Lys Ile Glu Lys Leu Pro Leu Val Lys Asp Gly
            180                 185                 190

Arg Leu Glu Gly Leu Ile Thr Ile Lys Asp Ile Glu Lys Val Ile Glu
```

```
            195                 200                 205
Phe Pro Asn Ala Ala Lys Asp Glu His Gly Arg Leu Leu Val Ala Ala
210                 215                 220

Ala Ile Gly Ile Ser Lys Asp Thr Asp Ile Arg Ala Gln Lys Leu Val
225                 230                 235                 240

Glu Ala Gly Val Asp Val Leu Val Ile Asp Thr Ala His Gly His Ser
                245                 250                 255

Lys Gly Val Ile Asp Gln Val Lys His Ile Lys Lys Thr Tyr Pro Glu
                260                 265                 270

Ile Thr Leu Val Ala Gly Asn Val Ala Thr Ala Glu Ala Thr Lys Asp
            275                 280                 285

Leu Phe Glu Ala Gly Ala Asp Ile Val Lys Val Gly Ile Gly Pro Gly
        290                 295                 300

Ser Ile Cys Thr Thr Arg Val Val Ala Gly Val Gly Val Pro Gln Ile
305                 310                 315                 320

Thr Ala Ile Tyr Asp Cys Ala Thr Glu Ala Arg Lys His Gly Lys Ala
                325                 330                 335

Ile Ile Ala Asp Gly Gly Ile Lys Phe Ser Gly Asp Ile Ile Lys Ala
                340                 345                 350

Leu Ala Ala Gly Gly His Ala Val Met Leu Gly Ser Leu Leu Ala Gly
            355                 360                 365

Thr Glu Glu Ser Pro Gly Ala Thr Glu Ile Phe Gln Gly Arg Gln Tyr
        370                 375                 380

Lys Val Tyr Arg Gly Met Gly Ser Leu Gly Ala Met Glu Lys Gly Ser
385                 390                 395                 400

Asn Asp Arg Tyr Phe Gln Glu Asp Lys Ala Pro Lys Lys Phe Val Pro
                405                 410                 415

Glu Gly Ile Glu Gly Arg Thr Ala Tyr Lys Gly Ala Leu Gln Asp Thr
                420                 425                 430

Ile Tyr Gln Leu Met Gly Gly Val Arg Ala Gly Met Gly Tyr Thr Gly
            435                 440                 445

Ser His Asp Leu Arg Glu Leu Arg Glu Glu Ala Gln Phe Thr Arg Met
        450                 455                 460

Gly Pro Ala Gly Leu Ala Glu Ser His Pro His Asn Ile Gln Ile Thr
465                 470                 475                 480

Lys Glu Ser Pro Asn Tyr Ser Phe
                485

<210> SEQ ID NO 37
<211> LENGTH: 402
<212> TYPE: PRT
<213> ORGANISM: Staphylococcus aureus

<400> SEQUENCE: 37

Met Ala Gln Asp Arg Lys Lys Val Leu Val Leu Gly Ala Gly Tyr Ala
1               5                   10                  15

Gly Leu Gln Thr Val Thr Lys Leu Gln Lys Ala Ile Ser Thr Glu Glu
                20                  25                  30

Ala Glu Ile Thr Leu Ile Asn Lys Asn Glu Tyr His Tyr Glu Ala Thr
            35                  40                  45

Trp Leu His Glu Ala Ser Ala Gly Thr Leu Asn Tyr Glu Asp Val Leu
        50                  55                  60

Tyr Pro Val Glu Ser Val Leu Lys Lys Asp Lys Val Asn Phe Val Gln
65                  70                  75                  80

Ala Glu Val Thr Lys Ile Asp Arg Asp Ala Lys Lys Val Glu Thr Asn
```

-continued

Gln Gly Ile Tyr Asp Phe Asp Ile Leu Val Val Ala Leu Gly Phe Val
            85                  90                  95
                100                 105                 110

Ser Glu Thr Phe Gly Ile Glu Gly Met Lys Asp His Ala Phe Gln Ile
        115                 120                 125

Glu Asn Val Ile Thr Ala Arg Glu Leu Ser Arg His Ile Glu Asp Lys
    130                 135                 140

Phe Ala Asn Tyr Ala Ala Ser Lys Glu Lys Asp Asp Asn Asp Leu Ser
145                 150                 155                 160

Ile Leu Val Gly Gly Ala Gly Phe Thr Gly Val Glu Phe Leu Gly Glu
                165                 170                 175

Leu Thr Asp Arg Ile Pro Glu Leu Cys Ser Lys Tyr Gly Val Asp Gln
            180                 185                 190

Asn Lys Val Lys Ile Thr Cys Val Glu Ala Ala Pro Lys Met Leu Pro
        195                 200                 205

Met Phe Ser Glu Glu Leu Val Asn His Ala Val Ser Tyr Leu Glu Asp
    210                 215                 220

Arg Gly Val Glu Phe Lys Ile Ala Thr Pro Ile Val Ala Cys Asn Glu
225                 230                 235                 240

Lys Gly Phe Val Val Glu Val Asp Gly Glu Lys Gln Gln Leu Asn Ala
                245                 250                 255

Gly Thr Ser Val Trp Ala Ala Gly Val Arg Gly Ser Lys Leu Met Glu
            260                 265                 270

Glu Ser Phe Glu Gly Val Lys Arg Gly Arg Ile Val Thr Lys Gln Asp
        275                 280                 285

Leu Thr Ile Asn Gly Tyr Asp Asn Ile Phe Val Ile Gly Asp Cys Ser
    290                 295                 300

Ala Phe Ile Pro Ala Gly Glu Glu Arg Pro Leu Pro Thr Thr Ala Gln
305                 310                 315                 320

Ile Ala Met Gln Gln Gly Glu Ser Val Ala Lys Asn Ile Lys Arg Ile
                325                 330                 335

Leu Asn Gly Glu Ser Thr Glu Glu Phe Glu Tyr Val Asp Arg Gly Thr
            340                 345                 350

Val Cys Ser Leu Gly Ser His Asp Gly Val Gly Met Val Phe Gly Lys
        355                 360                 365

Pro Ile Ala Gly Lys Lys Ala Ala Phe Met Lys Lys Val Ile Asp Thr
    370                 375                 380

Arg Ala Val Phe Lys Ile Gly Gly Ile Gly Leu Ala Phe Lys Lys Gly
385                 390                 395                 400

Lys Phe

<210> SEQ ID NO 38
<211> LENGTH: 438
<212> TYPE: PRT
<213> ORGANISM: Staphylococcus aureus

<400> SEQUENCE: 38

Met Pro Lys Ile Val Val Gly Ala Val Ala Gly Gly Ala Thr Cys
1               5                   10                  15

Ala Ser Gln Ile Arg Arg Leu Asp Lys Glu Ser Asp Ile Ile Phe
                20                  25                  30

Glu Lys Asp Arg Asp Met Ser Phe Ala Asn Cys Ala Leu Pro Tyr Val
            35                  40                  45

Ile Gly Glu Val Val Glu Asp Arg Lys Tyr Ala Leu Ala Tyr Thr Pro
        50                  55                  60

```
Glu Lys Phe Tyr Asp Arg Lys Gln Ile Thr Val Lys Thr Tyr His Glu
 65                  70                  75                  80

Val Ile Ala Ile Asn Asp Glu Arg Gln Thr Val Thr Val Leu Asn Arg
             85                  90                  95

Lys Thr Asn Glu Gln Phe Glu Ser Tyr Asp Lys Leu Ile Leu Ser
            100                 105                 110

Pro Gly Ala Ser Ala Asn Ser Leu Gly Phe Glu Ser Asp Ile Thr Phe
            115                 120                 125

Thr Leu Arg Asn Leu Glu Asp Thr Asp Ala Ile Asp Gln Phe Ile Lys
130                 135                 140

Ala Asn Gln Val Asp Lys Val Leu Val Val Gly Ala Gly Tyr Val Ser
145                 150                 155                 160

Leu Glu Val Leu Glu Asn Leu Tyr Glu Arg Gly Leu His Pro Thr Leu
                165                 170                 175

Ile His Arg Ser Asp Lys Ile Asn Lys Leu Met Asp Ala Asp Met Asn
            180                 185                 190

Gln Pro Ile Leu Asp Glu Leu Asp Lys Arg Glu Ile Pro Tyr Arg Leu
            195                 200                 205

Asn Glu Glu Ile Asp Ala Ile Asn Gly Asn Glu Ile Thr Phe Lys Ser
210                 215                 220

Gly Lys Val Glu His Tyr Asp Met Ile Ile Glu Gly Val Gly Thr His
225                 230                 235                 240

Pro Asn Ser Lys Phe Ile Glu Ser Ser Asn Ile Lys Leu Asp Arg Lys
                245                 250                 255

Gly Phe Ile Pro Val Asn Asp Lys Phe Glu Thr Asn Val Pro Asn Ile
            260                 265                 270

Tyr Ala Ile Gly Asp Ile Ala Thr Ser His Tyr Arg His Val Asp Leu
            275                 280                 285

Pro Ala Ser Val Pro Leu Ala Trp Gly Ala His Arg Ala Ala Ser Ile
290                 295                 300

Val Ala Glu Gln Ile Ala Gly Asn Asp Thr Ile Glu Phe Lys Gly Phe
305                 310                 315                 320

Leu Gly Asn Asn Ile Val Lys Phe Phe Asp Tyr Thr Phe Ala Ser Val
                325                 330                 335

Gly Val Lys Pro Asn Glu Leu Lys Gln Phe Asp Tyr Lys Met Val Glu
            340                 345                 350

Val Thr Gln Gly Ala His Ala Asn Tyr Tyr Pro Gly Asn Ser Pro Leu
            355                 360                 365

His Leu Arg Val Tyr Tyr Asp Thr Ser Asn Arg Gln Ile Leu Arg Ala
370                 375                 380

Ala Ala Val Gly Lys Glu Gly Ala Asp Lys Arg Ile Asp Val Leu Ser
385                 390                 395                 400

Met Ala Met Met Asn Gln Leu Thr Val Asp Glu Leu Thr Glu Phe Glu
                405                 410                 415

Val Ala Tyr Ala Pro Pro Tyr Ser His Pro Lys Asp Leu Ile Asn Met
            420                 425                 430

Ile Gly Tyr Lys Ala Lys
            435

<210> SEQ ID NO 39
<211> LENGTH: 293
<212> TYPE: PRT
<213> ORGANISM: Staphylococcus aureus

<400> SEQUENCE: 39
```

Met Ala Thr Ile Ser Ala Lys Leu Val Lys Glu Leu Arg Lys Lys Thr
1               5                   10                  15

Gly Ala Gly Met Met Asp Cys Lys Lys Ala Leu Thr Glu Thr Asp Gly
                20                  25                  30

Asp Ile Asp Lys Ala Ile Asp Tyr Leu Arg Glu Lys Gly Ile Ala Lys
            35                  40                  45

Ala Ala Lys Lys Ala Asp Arg Ile Ala Ala Glu Gly Leu Val His Val
        50                  55                  60

Glu Thr Lys Gly Asn Asp Ala Val Ile Val Ile Asn Ser Glu Thr
65                  70                  75                  80

Asp Phe Val Ala Arg Asn Glu Gly Phe Gln Glu Leu Val Lys Glu Ile
                85                  90                  95

Ala Asn Gln Val Leu Asp Thr Lys Ala Glu Thr Val Glu Ala Leu Met
            100                 105                 110

Glu Thr Thr Leu Pro Asn Gly Lys Ser Val Asp Glu Arg Ile Lys Glu
        115                 120                 125

Ala Ile Ser Thr Ile Gly Glu Lys Leu Ser Val Arg Arg Phe Ala Ile
    130                 135                 140

Arg Thr Lys Thr Asp Asn Asp Ala Phe Gly Ala Tyr Leu His Met Gly
145                 150                 155                 160

Gly Arg Ile Gly Val Leu Thr Val Val Glu Gly Ser Thr Asp Glu Glu
                165                 170                 175

Ala Ala Arg Asp Val Ala Met His Ile Ala Ala Ile Asn Pro Lys Tyr
            180                 185                 190

Val Ser Ser Glu Gln Val Ser Glu Glu Ile Asn His Glu Arg Glu
        195                 200                 205

Val Leu Lys Gln Gln Ala Leu Asn Glu Gly Lys Pro Glu Asn Ile Val
    210                 215                 220

Glu Lys Met Val Glu Gly Arg Leu Arg Lys Tyr Leu Gln Glu Ile Cys
225                 230                 235                 240

Ala Val Asp Gln Asp Phe Val Lys Asn Pro Asp Val Thr Val Glu Ala
                245                 250                 255

Phe Leu Lys Thr Lys Gly Gly Lys Leu Val Asp Phe Val Arg Tyr Glu
            260                 265                 270

Val Gly Glu Gly Met Glu Lys Arg Glu Glu Asn Phe Ala Asp Glu Val
        275                 280                 285

Lys Gly Gln Met Lys
    290

<210> SEQ ID NO 40
<211> LENGTH: 475
<212> TYPE: PRT
<213> ORGANISM: Staphylococcus aureus

<400> SEQUENCE: 40

Met His Phe Glu Thr Val Ile Gly Leu Glu Val His Val Glu Leu Lys
1               5                   10                  15

Thr Asp Ser Lys Met Phe Ser Pro Ser Ala His Phe Gly Ala Glu
            20                  25                  30

Pro Asn Ser Asn Thr Asn Val Ile Asp Leu Ala Tyr Pro Gly Val Leu
        35                  40                  45

Pro Val Val Asn Lys Arg Ala Val Asp Trp Ala Met Arg Ala Ala Met
    50                  55                  60

Ala Leu Asn Met Glu Ile Ala Thr Glu Ser Lys Phe Asp Arg Lys Asn
65                  70                  75                  80

Tyr Phe Tyr Pro Asp Asn Pro Lys Ala Tyr Gln Ile Ser Gln Phe Asp
                85                  90                  95

Gln Pro Ile Gly Glu Asn Gly Tyr Ile Asp Ile Glu Val Asp Gly Glu
            100                 105                 110

Thr Lys Arg Ile Gly Ile Thr Arg Leu His Met Glu Glu Asp Ala Gly
            115                 120                 125

Lys Ser Thr His Lys Gly Glu Tyr Ser Leu Val Asp Leu Asn Arg Gln
130                 135                 140

Gly Thr Pro Leu Ile Glu Ile Val Ser Glu Pro Asp Ile Arg Ser Pro
145                 150                 155                 160

Lys Glu Ala Tyr Ala Tyr Leu Glu Lys Leu Arg Ser Ile Ile Gln Tyr
                165                 170                 175

Thr Gly Val Ser Asp Val Lys Met Glu Glu Gly Ser Leu Arg Cys Asp
            180                 185                 190

Ala Asn Ile Ser Leu Arg Pro Tyr Gly Gln Glu Lys Phe Gly Thr Lys
            195                 200                 205

Ala Glu Leu Lys Asn Leu Asn Ser Phe Asn Tyr Val Arg Lys Gly Leu
        210                 215                 220

Glu Tyr Glu Glu Lys Arg Gln Glu Glu Leu Leu Ser Gly Gly Glu
225                 230                 235                 240

Ile Gly Gln Glu Thr Arg Arg Phe Asp Glu Ser Thr Gly Lys Thr Ile
                245                 250                 255

Leu Met Arg Val Lys Glu Gly Ser Asp Asp Tyr Arg Tyr Phe Pro Glu
            260                 265                 270

Pro Asp Ile Val Pro Leu Tyr Ile Asp Asp Ala Trp Lys Glu Arg Val
        275                 280                 285

Arg Gln Thr Ile Pro Glu Leu Pro Asp Glu Arg Lys Ala Lys Tyr Val
        290                 295                 300

Asn Glu Leu Gly Leu Pro Ala Tyr Asp Ala His Val Leu Thr Leu Thr
305                 310                 315                 320

Lys Glu Met Ser Asp Phe Phe Glu Ser Thr Ile Glu His Gly Ala Asp
                325                 330                 335

Val Lys Leu Thr Ser Asn Trp Leu Met Gly Gly Val Asn Glu Tyr Leu
            340                 345                 350

Asn Lys Asn Gln Val Glu Leu Leu Asp Thr Lys Leu Thr Pro Glu Asn
        355                 360                 365

Leu Ala Gly Met Ile Lys Leu Ile Glu Asp Gly Thr Met Ser Ser Lys
370                 375                 380

Ile Ala Lys Lys Val Phe Pro Glu Leu Ala Ala Lys Gly Gly Asn Ala
385                 390                 395                 400

Lys Gln Ile Met Glu Asp Asn Gly Leu Val Gln Ile Ser Asp Glu Ala
                405                 410                 415

Thr Leu Leu Lys Phe Val Asn Glu Ala Leu Asp Asn Asn Glu Gln Ser
            420                 425                 430

Val Glu Asp Tyr Lys Asn Gly Lys Gly Lys Ala Met Gly Phe Leu Val
        435                 440                 445

Gly Gln Ile Met Lys Ala Ser Lys Gly Gln Ala Asn Pro Gln Leu Val
        450                 455                 460

Asn Gln Leu Leu Lys Gln Glu Leu Asp Lys Arg
465                 470                 475

<210> SEQ ID NO 41
<211> LENGTH: 309
<212> TYPE: PRT

<213> ORGANISM: Staphylococcus aureus

<400> SEQUENCE: 41

Met Ala Lys Thr Tyr Ile Phe Gly His Lys Asn Pro Asp Thr Asp Ala
1               5                   10                  15

Ile Ser Ser Ala Ile Ile Met Ala Glu Phe Glu Gln Leu Arg Gly Asn
            20                  25                  30

Ser Gly Ala Lys Ala Tyr Arg Leu Gly Asp Val Ser Ala Glu Thr Gln
        35                  40                  45

Phe Ala Leu Asp Thr Phe Asn Val Pro Ala Pro Glu Leu Leu Thr Asp
    50                  55                  60

Asp Leu Asp Gly Gln Asp Val Ile Leu Val Asp His Asn Glu Phe Gln
65                  70                  75                  80

Gln Ser Ser Asp Thr Ile Ala Ser Ala Thr Ile Lys His Val Ile Asp
                85                  90                  95

His His Arg Ile Ala Asn Phe Glu Thr Ala Gly Pro Leu Cys Tyr Arg
            100                 105                 110

Ala Glu Pro Val Gly Cys Thr Ala Thr Ile Leu Tyr Lys Met Phe Arg
        115                 120                 125

Glu Arg Gly Phe Glu Ile Lys Pro Glu Ile Ala Gly Leu Met Leu Ser
    130                 135                 140

Ala Ile Ile Ser Asp Ser Leu Leu Phe Lys Ser Pro Thr Cys Thr Gln
145                 150                 155                 160

Gln Asp Val Lys Ala Ala Glu Glu Leu Lys Asp Ile Ala Lys Val Asp
                165                 170                 175

Ile Gln Lys Tyr Gly Leu Asp Met Leu Lys Ala Gly Ala Ser Thr Thr
            180                 185                 190

Asp Lys Ser Val Glu Phe Leu Leu Asn Met Asp Ala Lys Ser Phe Thr
        195                 200                 205

Met Gly Asp Tyr Val Thr Arg Ile Ala Gln Val Asn Ala Val Asp Leu
    210                 215                 220

Asp Glu Val Leu Asn Arg Lys Glu Asp Leu Glu Lys Glu Met Leu Ala
225                 230                 235                 240

Val Ser Ala Gln Glu Lys Tyr Asp Leu Phe Val Leu Val Val Thr Asp
                245                 250                 255

Ile Ile Asn Ser Asp Ser Lys Ile Leu Val Val Gly Ala Glu Lys Asp
            260                 265                 270

Lys Val Gly Glu Ala Phe Asn Val Gln Leu Glu Asp Met Ala Phe
        275                 280                 285

Leu Ser Gly Val Val Ser Arg Lys Lys Gln Ile Val Pro Gln Ile Thr
    290                 295                 300

Glu Ala Leu Thr Lys
305

<210> SEQ ID NO 42
<211> LENGTH: 325
<212> TYPE: PRT
<213> ORGANISM: Staphylococcus aureus

<400> SEQUENCE: 42

Met Ala Gln Met Thr Met Val Gln Ala Ile Asn Asp Ala Leu Lys Thr
1               5                   10                  15

Glu Leu Lys Asn Asp Gln Asp Val Leu Ile Phe Gly Glu Asp Val Gly
            20                  25                  30

Val Asn Gly Gly Val Phe Arg Val Thr Glu Gly Leu Gln Lys Glu Phe
        35                  40                  45

Gly Glu Asp Arg Val Phe Asp Thr Pro Leu Ala Glu Ser Gly Ile Gly
            50                  55                  60

Gly Leu Ala Met Gly Leu Ala Val Glu Gly Phe Arg Pro Val Met Glu
65                  70                  75                  80

Val Gln Phe Leu Gly Phe Val Phe Glu Val Phe Asp Ala Ile Ala Gly
                85                  90                  95

Gln Ile Ala Arg Thr Arg Phe Arg Ser Gly Gly Thr Lys Thr Ala Pro
            100                 105                 110

Val Thr Ile Arg Ser Pro Phe Gly Gly Val His Thr Pro Glu Leu
            115                 120                 125

His Ala Asp Asn Leu Glu Gly Ile Leu Ala Gln Ser Pro Gly Leu Lys
            130                 135                 140

Val Val Ile Pro Ser Gly Pro Tyr Asp Ala Lys Gly Leu Leu Ile Ser
145                 150                 155                 160

Ser Ile Arg Ser Asn Asp Pro Val Val Tyr Leu Glu His Met Lys Leu
                165                 170                 175

Tyr Arg Ser Phe Arg Glu Val Pro Glu Glu Tyr Thr Ile Asp
                180                 185                 190

Ile Gly Lys Ala Asn Val Lys Lys Glu Gly Asn Asp Ile Ser Ile Ile
            195                 200                 205

Thr Tyr Gly Ala Met Val Gln Glu Ser Met Lys Ala Ala Glu Glu Leu
            210                 215                 220

Glu Lys Asp Gly Tyr Ser Val Glu Val Ile Asp Leu Arg Thr Val Gln
225                 230                 235                 240

Pro Ile Asp Val Asp Thr Ile Val Ala Ser Val Glu Lys Thr Gly Arg
                245                 250                 255

Ala Val Val Val Gln Glu Ala Gln Arg Gln Ala Gly Val Gly Ala Ala
            260                 265                 270

Val Val Ala Glu Leu Ser Glu Arg Ala Ile Leu Ser Leu Glu Ala Pro
            275                 280                 285

Ile Gly Arg Val Ala Ala Ala Asp Thr Ile Tyr Pro Phe Thr Gln Ala
            290                 295                 300

Glu Asn Val Trp Leu Pro Asn Lys Asn Asp Ile Ile Glu Lys Ala Lys
305                 310                 315                 320

Glu Thr Leu Glu Phe
                325

<210> SEQ ID NO 43
<211> LENGTH: 142
<212> TYPE: PRT
<213> ORGANISM: Staphylococcus aureus

<400> SEQUENCE: 43

Met Lys Tyr Asp Asp Phe Ile Val Gly Glu Thr Phe Lys Thr Lys Ser
1               5                   10                  15

Leu His Ile Thr Glu Glu Ile Ile Gln Phe Ala Thr Thr Phe Asp
                20                  25                  30

Pro Gln Tyr Met His Ile Asp Lys Glu Lys Ala Glu Gln Ser Arg Phe
            35                  40                  45

Lys Gly Ile Ile Ala Ser Gly Met His Thr Leu Ser Ile Ser Phe Lys
            50                  55                  60

Leu Trp Val Glu Glu Gly Lys Tyr Gly Glu Glu Val Val Ala Gly Thr
65                  70                  75                  80

Gln Met Asn Asn Val Lys Phe Ile Lys Pro Val Tyr Pro Gly Asn Thr
                85                  90                  95

-continued

Leu Tyr Val Ile Ala Glu Ile Thr Asn Lys Lys Ser Ile Lys Lys Glu
        100                 105                 110

Asn Gly Leu Val Thr Val Ser Leu Ser Thr Tyr Asn Glu Asn Glu Glu
        115                 120                 125

Ile Val Phe Lys Gly Glu Val Thr Ala Leu Ile Asn Asn Ser
    130                 135                 140

<210> SEQ ID NO 44
<211> LENGTH: 24
<212> TYPE: DNA
<213> ORGANISM: Artificial
<220> FEATURE:
<223> OTHER INFORMATION: Synthetic

<400> SEQUENCE: 44
atgaatacaa tcaaaactac gaaa                                          24

<210> SEQ ID NO 45
<211> LENGTH: 37
<212> TYPE: DNA
<213> ORGANISM: Artificial
<220> FEATURE:
<223> OTHER INFORMATION: Synthetic

<400> SEQUENCE: 45
cttctcatcg tcatctgatt tcaaaatcca tttttga                            37

<210> SEQ ID NO 46
<211> LENGTH: 43
<212> TYPE: DNA
<213> ORGANISM: Artificial
<220> FEATURE:
<223> OTHER INFORMATION: Synthetic

<400> SEQUENCE: 46
actctaggtc tcactcccat ctgaaacaac attatgacca aat                     43

<210> SEQ ID NO 47
<211> LENGTH: 45
<212> TYPE: DNA
<213> ORGANISM: Artificial
<220> FEATURE:
<223> OTHER INFORMATION: Synthetic

<400> SEQUENCE: 47
atggtaggtc tcatatcata aggatttaa cggtaattca ttact                    45

<210> SEQ ID NO 48
<211> LENGTH: 43
<212> TYPE: DNA
<213> ORGANISM: Artificial
<220> FEATURE:
<223> OTHER INFORMATION: Synthetic

<400> SEQUENCE: 48
atggtaggtc tcactccgat aagtcaaatg gcaaactaaa agt                     43

<210> SEQ ID NO 49
<211> LENGTH: 40
<212> TYPE: DNA
<213> ORGANISM: Artificial
<220> FEATURE:
<223> OTHER INFORMATION: Synthetic

<400> SEQUENCE: 49

```
atggtaggtc tcatatcatt tcatgcttcc gtgtacagtt                    40

<210> SEQ ID NO 50
<211> LENGTH: 43
<212> TYPE: DNA
<213> ORGANISM: Artificial
<220> FEATURE:
<223> OTHER INFORMATION: Synthetic

<400> SEQUENCE: 50
atggtaggtc tcactccgct tatactgtta ctaaaccaca aac                43

<210> SEQ ID NO 51
<211> LENGTH: 44
<212> TYPE: DNA
<213> ORGANISM: Artificial
<220> FEATURE:
<223> OTHER INFORMATION: Synthetic

<400> SEQUENCE: 51
atggtaggtc tcatatcatt tatattgtgg gatgtcgaag tatt               44

<210> SEQ ID NO 52
<211> LENGTH: 43
<212> TYPE: DNA
<213> ORGANISM: Artificial
<220> FEATURE:
<223> OTHER INFORMATION: Synthetic

<400> SEQUENCE: 52
actctaggtc tcactccaaa gaagattcaa aagaagaaca aat                43

<210> SEQ ID NO 53
<211> LENGTH: 40
<212> TYPE: DNA
<213> ORGANISM: Artificial
<220> FEATURE:
<223> OTHER INFORMATION: Synthetic

<400> SEQUENCE: 53
atggtaggtc tcatatcagc tatcttcatc agacggccca                    40
```

METHODS AND DEVICES FOR THE DETECTION OF BIOFILM

CROSS-REFERENCE TO RELATED APPLICATIONS

This application is the U.S. National Stage Application under 35 U.S.C. §371 of International Application No. PCT/US2008/071633, with an international filing date of Jul. 30, 2008, which claims the benefit of U.S. Provisional Patent Application Ser. Nos. 60/952,786 filed Jul. 30, 2007 and 60/974,258 filed Sep. 21, 2007, which are incorporated by reference herein in their entirety.

STATEMENT OF GOVERNMENT INTEREST

Portions of this work were supported by Allergy and Infectious Diseases, National Institutes of Health, under contract number N01-AI-15447 and by the National Institute of Allergy and Infectious Diseases, National Institutes of Health grant R01 AI69568-01A2. Thus, the U.S. government has certain rights in this application.

REFERENCE TO A SEQUENCE LISTING SUBMITTED ELECTRONICALLY VIA EFS-WEB

The content of the sequence listing (Name: Sequence_listing.txt, Size: 140,276 bytes; and Date of Creation: Jun. 21, 2010) electronically submitted via EFS-Web is incorporated by reference in its entirety.

BACKGROUND OF INVENTION

Advances in medical technology and diagnostic techniques have led to improved healthcare. Faster diagnosis leads to better treatment regimes and shorter hospital-stays. However, with the increasing understanding of microbial pathogenesis in humans, particularly the role biofilms play in microbial infections, a closer look must be taken into the efficiency of current diagnostic methods for detecting a biofilm and to determine novel diagnostic techniques that specifically target biofilm infections.

In recent years there has been heightened interest in how microbes form biofilms and in their relevance in a clinical setting. Biofilm infections are problematic in hospitals and contribute to the morbidity and mortality of immunocompromised patients. These infections can range from minor conditions such as boils, kidney stones, and gingivitis to more life-threatening illnesses such as osteomyelitis, endocarditis, pneumonia, medical device failure, and cystic fibrosis infections (Shirtliff et al., 2002; Parsek and Singh, 2003; Mack et al., 2006; Sanderson et al., 2006).

During the formation of a biofilm, planktonic bacteria, which are bacterial cells that are free to move passively or actively through bodily fluids, first attach to a surface (which can be damaged tissue or implanted medical devices), secrete a matrix of exopolymeric substance (EPS) that encase the bacteria, and mature to form heterogeneous communities of microorganisms that are resistant to antibiotics and host defenses. The biofilm community is dynamic and after maturation, clusters or individual cells detach and spread throughout the body (O'Toole et al., 2000). A biofilm can be mono- or polymicrobial and once maturity is reached, resolution is only successful upon debridement of the infected tissue or device. The matrix that surrounds the bacteria plays an important role in its virulence. For example, methicillin-resistant *Staphylococcus aureus* biofilms are up to 1,000 times more resistant to vancomycin than when they are grown in a planktonic suspension (Jefferson et al., 2005). Also, host immunity is compromised during biofilm infections as white blood cells are capable of penetrating and creating antibodies against a biofilm but the immune system is incapable of resolving the infection (Leid et al., 2002b; Jesaitis et al., 2003; Leid et al., 2005; Brady et al., 2006).

Diagnosis of biofilm infections is currently accomplished though a variety of testing methods. Elevated white blood cell counts and C-reactive protein levels are good indicators of inflammation but these tests are not specific for the presence of biofilm (Trampuz and Zimmerli, 2006). Culturing is one of the most routine methods used in identifying microorganisms causing disease but contamination and long processing times are common problems. The inefficiency of traditional culturing methods to correctly identify microbes is exacerbated with biofilms. For example, biofilm microorganisms are difficult or impossible to culture on standard agar plates (Veeh et al., 2003). Nonetheless, since biofilm organisms are inherently attached to a surface, they are not readily cultured by standard techniques.

There are several non-culturing methods used to diagnose biofilm infections. These include imaging tests such as X-ray, CT scans or MRI and are advantageous because they identify the location of infection. These procedures are most useful when used secondarily to a diagnostic technique that first confirms the presence of an infection (Trampuz and Zimmerli, 2006). Drawbacks of imaging techniques, however, include their lack of ability to differentiate between infection and inflammation as well as the costly equipment required to perform these tests. Specificity of these tests for a particular pathogen are not yet available. Serology based assays are becoming more fashionable and address the problem of insensitivity with the previous techniques described. These assays function on the principle of antigen/antibody interaction and can diagnose infection by identifying antibodies in sera that are not normally present in healthy hosts. However, since *S. aureus* is such a ubiquitous pathogen, this approach can lead to reduced sensitivity as most of the population has either been colonized or infected by *S. aureus*. For these reasons, it is important to develop new, rapid, and inexpensive techniques to diagnose biofilm infections.

SUMMARY OF THE INVENTION

In a first aspect the invention provides methods for detecting the presence of a biofilm comprising:

a) contacting a test sample with one or more detectably labeled proteins, wherein the one or more detectably labeled proteins are capable of binding antibodies present in the test sample, wherein the binding produces labeled antibodies;

b) contacting the labeled antibodies to a substrate comprising one or more immobilized biofilm markers; wherein the one or more immobilized biofilm markers derived from one or more proteins selected from the group consisting of SEQ ID NO:1 (hypothetical protein SA 0486; YP_039889), SEQ ID NO:2 (hypothetical protein SAR0056, YP_039527), SEQ ID NO:3 (glucosaminidase, YP_040441), SEQ ID NO:13 (lipoprotein ABC transporter protein; accession no. 15923621), and SA0037 (conserved hypothetical protein; SEQ ID NO: 43) or antigenic fragments thereof; and c) detecting binding of the labeled antibodies to the one or more immobilized biofilm markers, wherein binding indicates the presence of a biofilm in the test sample.

In a second aspect the invention provides a method for diagnosing biofilm related diseases, comprising:
  a) contacting a test sample from a subject with one or more detectably labeled proteins, wherein the one or more detectably labeled proteins are capable of binding antibodies present in the test sample, wherein the binding produces labeled antibodies;
  b) contacting the labeled antibodies to a substrate comprising one or more immobilized biofilm markers; wherein the one or more immobilized biofilm markers comprises one or more proteins derived from the group consisting of SEQ ID NO:1, SEQ ID NO:2, SEQ ID NO:3, SEQ ID NO:13, and SEQ ID NO: 43 or antigenic fragments thereof; and
  c) detecting binding of the labeled antibodies to the one or more immobilized biofilm markers, wherein binding indicates the presence of a biofilm related disease in the subject.

In a third aspect the invention provides a method for diagnosing osteomyelitis, comprising:
  a) contacting a test sample from a subject with one or more detectably labeled proteins, wherein the one or more detectably labeled proteins are capable of binding antibodies present in the test sample, wherein the binding produces labeled antibodies;
  b) contacting the labeled antibodies to a substrate comprising one or more immobilized biofilm markers; wherein the one or more immobilized biofilm markers comprises one or more proteins derived from the group consisting of SEQ ID NO:1, SEQ ID NO:2, SEQ ID NO:3, SEQ ID NO:13, and SEQ ID NO: 43 or antigenic fragments thereof; and
  c) detecting binding of the labeled antibodies to the one or more immobilized biofilm markers, wherein binding indicates the presence of osteomyelitis in the subject.

In a fourth aspect the invention provides biofilm detection substrates comprising:
  a) a test well comprising one or more detectably labeled proteins, wherein the one or more detectably labeled proteins are capable of binding to biofilm antibodies present in a test sample; and
  b) one or more immobilized biofilm markers capable of binding to labeled antibodies, wherein the one or more immobilized biofilm markers comprises one or more proteins derived from the group consisting of SEQ ID NO:1, SEQ ID NO:2, SEQ ID NO:3, SEQ ID NO:13. and SEQ ID NO: 43.

DETAILED DESCRIPTION OF INVENTION

Figure 1:
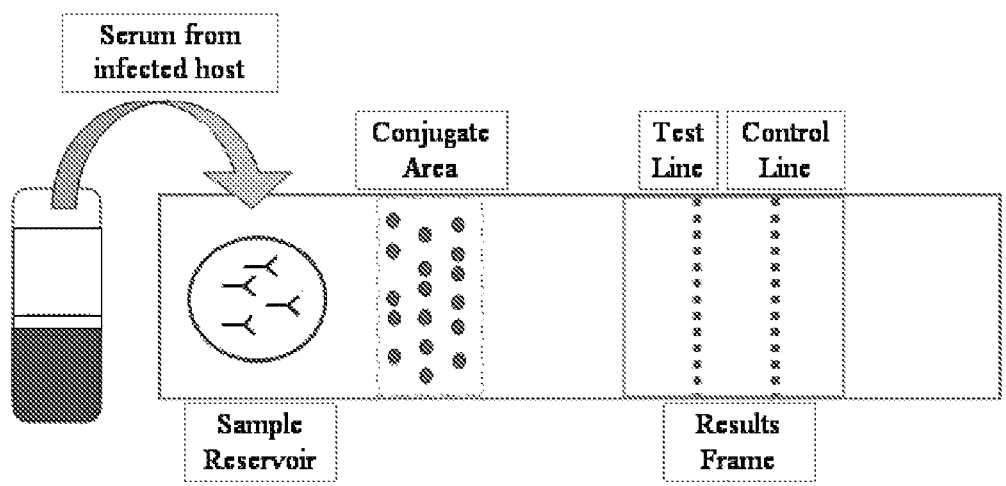
FIG. 1. Schematic of lateral flow immunoassay for detection of biofilm infection.

In a first aspect the invention provides methods for detecting the presence of a biofilm comprising:
  a) contacting a test sample with one or more detectably labeled proteins, wherein the one or more detectably labeled proteins are capable of binding antibodies present in the test sample, wherein the binding produces labeled antibodies;
  b) contacting the labeled antibodies to a substrate comprising one or more immobilized biofilm markers; wherein the one or more immobilized biofilm markers comprises one or more proteins derived from the group consisting of SEQ ID NO:1, SEQ ID NO:2, SEQ ID NO:3, SEQ ID NO:13, and SEQ ID NO: 43 or antigenic fragments thereof; and
  c) detecting binding of the labeled antibodies to the one or more immobilized biofilm markers, wherein binding indicates the presence of a biofilm in the test sample.

The present invention provides methods and devices for rapid and minimally invasive detection of biofilm infections and the diseases associated with biofilm infections. The methods and device can be used, for example, to identify antibodies to biofilm markers in a test sample taken from a patient, with much greater speed, specificity and sensitivity than traditional methods of biofilm detection which are slow and have poor sensitivity and selectivity, require an invasive test sample taken directly from the source of the infection and require secondary diagnostics to confirm the presence of a biofilm infection. Furthermore, measuring the interactions between an antibody and biofilm markers has a higher accuracy relative to the culturing and imaging diagnostics currently used. In addition to the reductions in cost and the less invasive availability of sample material required, the detection techniques of the present invention are faster due to the rapid detection of binding between the labeled antibodies and the immobilized markers. Faster diagnosis can allow for more effective and rapid treatment, thereby reducing the cost of treatment as well.

"Biofilms" are biological films of surface-attached communities of microorganisms that form and persist at the surfaces of biological objects in aqueous environments from the adsorption of microbial cells onto the solid surfaces. This adsorption can provide a competitive advantage for the microorganisms since they can reproduce, are accessible to a wider variety of nutrients and oxygen conditions, are not washed away, and are less sensitive to antimicrobial agents. Biofilms can develop into macroscopic structures several millimeters or centimeters in thickness and cover large surface areas causing pathogenic problems in the body, including but not limited to teeth, gums, ears, prostate, systemic vasculature, lungs, and heart and in medical devices, including, but not limited to catheters, orthopedic devices, implants, prosthetic heart valves, prosthetic joints, orthopedic implants, shunts, pacemaker and defibrillator, endotracheal intubation, hemodialysis/peritoneal dialysis devices, dental implants, intravascular catheters, intrauterine devices (IUDs), and any inert and chemically modified plastic used for implant or medical device purposes. Biofilms are a major source of hospital infections and bacteria growing in biofilms are more resistant to antibiotics and disinfectants than other microorganisms. Biological objects subject to biofilm formation include, but are not limited to damaged tissue, catheters, orthopedic devices, implants, prosthetic heart valves, prosthetic joints, orthopedic implants, shunts, pacemaker and defibrillator, endotracheal intubation, hemodialysis/peritoneal dialysis devices, dental implants, intravascular catheters, intrauterine devices (IUDs), and any inert and chemically modified plastic used for implant or medical device purposes, and such biofilm infections form more readily in immunocompromised patients. Biofilms can comprise or consist of microorganisms including, but not limited to bacteria, archaea, protozoa, fungi and algae. Bacteria present in a biofilm can be any gram positive or gram negative bacteria. In non-limiting embodiments, the bacteria present in the biofilm comprise or consist of *Staphylococcus aureus, Coliforms, Enterococcus,* or *Escherichia coli*. In a non-limiting embodiment, the *Staphylococcus aureus* may comprise or consist of methicillin-resistant *Staphylococcus aureus* (MRSA) or methicillin-susceptible *Staphylococcus aureus* (MSSA).

The "test sample" may be any suitable sample that can be tested using the devices and methods of the invention, including but not limited to body fluid samples including but not limited to, for example, plasma, serum, blood, spinal fluid, semen, lymph fluid, tears, saliva, and breast milk. The test sample can be taken from a patient suspected of having a biofilm infection, including, but not limited to, those suspected of having osteomyelitis, endocarditis, and heart valve issues. The test sample can thus be derived from patient samples for use in, for example, clinical diagnostics, clinical prognostics, and assessment of an ongoing course of therapeutic treatment for biofilm infection in a patient. Further uses include, but are not limited to, drug discovery and basic research use. Such test samples can be obtained from any suitable subject population at risk of developing a biofilm infection, including but not limited to hospital patients, immunocompromised individuals, individuals suffering from or suspected to have contracted a bacterial infection, subjects suffering from one or more of osteomyelitis, endocarditis, chronic rhinosinusitis, chronic lung infections, catheter occlusion, biofilm related heart valve defects and medical device failure, or any subject with an implanted medical device, including but not limited to orthopedic devices, cosmetic implants, prosthetic heart valves, prosthetic joints, orthopedic implants, shunts, pacemaker and defibrillator, endotracheal intubation, hemodialysis/peritoneal dialysis devices, dental implants, intravascular catheters, intrauterine devices (IUDs), and any inert and chemically modified plastic used for implant or medical device purposes.

According to the methods of the invention the test sample is contacted with one or more detectably labeled proteins which are capable of binding to antibodies present in the test sample. Contacting of the test sample with the detectably labeled proteins can occur in any way suitable for use in the inventions including, but not limited to, in solution, on a substrate, and in a test well. In non-limiting embodiments the test well is independent from the substrate or is located on or adjacent to the substrate. The test well or substrate may also comprise liquid buffers or buffer salts for facilitating binding of the one or more proteins to the antibodies in the test sample.

The "detectably labeled proteins" can be any protein, aptamer or non-protein molecule suitable for nonspecific binding to antibodies present in the test sample or which are capable of binding to the antibodies without affecting the antigen binding site in the antibody. Suitable proteins include, but are not limited to Protein A, Protein G, secondary antibodies (e.g. rabbit anti-human), or specific peptide sequences, such as peptides expressed by phage display.

In the instant invention, the protein is detectably labeled. The "detectable label" can be any one or more detectable labels suitable for binding to the protein, including but not limited to fluorescent dyes, quantum dots, enzyme markers, biotin, avidin, colloidal gold, radioactive iodine and magnetic, latex or sepharose beads. Binding of the detectable label to the protein can be by any means known in the art including, but not limited to covalent and non-covalent binding. Non-covalent binding methods can include avidin/biotin, lectin/carbohydrate, and Van der Waals forces of hydrophobic interactions. In a non-limiting embodiment, Protein A conjugated to colloidal gold binds to antibodies present in the test sample producing gold-labeled antibodies which are capable of binding to a biofilm marker.

The detectably labeled antibodies are then contacted to the substrate. Contacting of the detectably labeled antibodies to the substrate can be by any suitable means, including placement of a liquid test sample on the substrate or placement of the substrate into the test well. The substrate may comprise, for example, a test well, a well of a microtiter plate or a sample pad or test strip.

The "substrate" can be any surface suitable for use in the invention. Such surfaces include, but are not limited to, those comprising cellulose, cotton, nitrocellulose, paper, PVDF paper, silica gel, glass, plastic, and metal. In a non-limiting embodiment, the substrate comprises a pre-coated, poly lysine, plate. In a preferred embodiment the substrate comprises nitrocellulose suitable for use in chromatography.

According the methods of the invention the substrate comprises one or more immobilized biofilm markers. "Biofilm markers" can comprise or consist of any molecular entity suitable for binding antibodies, including but not limited to polypeptides. In non-limiting embodiments the biofilm markers comprise bacterial polypeptides expressed in bacteria including, but not limited to, *Staphylococcus aureus*, methicillin-resistant *Staphylococcus aureus*, and *Escherichia coli*. The biofilm specific molecules can be specific for different types of biofilm infections or diseases. The one or more immobilized biofilm markers may comprise or consist of 1, 2, 3, 4, 5, or more biofilm markers. For example, in embodiments where it is desired to multiplex the detection assay (i.e.: detect more than one biofilm antibody at a time), a plurality of different biofilm markers (that will bind to different antibodies) can be used.

The biofilm specific molecules are immobilized on the substrate via any suitable covalent or non-covalent binding, including but not limited to, hydrogen bonding, ionic bonding, hydrophobic interactions, Van der Waals forces, and dipole-dipole bonds, including both direct and indirect binding.

In accordance with the instant invention, the one or more immobilized biofilm markers comprise one or more proteins derived from the group consisting of SEQ ID NO:1, SEQ ID NO:2, SEQ ID NO:3, SEQ ID NO:13, and SEQ ID NO: 43 or antigenic portions thereof. As used herein, "derived from" means that the marker may be the entire protein, or a polypeptide containing one or more epitopes thereof (antigenic fragments). Those of skill in the art understand that antibodies can be characterized by their ability to specifically and/or selectively bind to one or more epitopes on a target protein, and methods for "epitope mapping" are well known in the art. An epitope as described herein may comprise amino acid residues directly involved in the binding of the antibody (the immunodominant component of the epitope) and other amino acid residues, which are not directly involved in the binding, such as amino acid residues which are effectively blocked by bound antibody. As is also well known in the art, bacterial proteins mutate over time, and thus it is possible that, within a population of S. aureus isolates, the proteins would vary by one or a few amino acid substitutions, insertions, deletions, etc., while maintaining one or more epitopes for the antibody of interest. Thus, as used herein, the proteins are "derived from" the recited sequences, and thus minor deviations in amino acid sequence from the recited SEQ ID NO are encompassed by the claims, so long as the protein function is maintained, which can be determined by its incorporation into growing bacterial biofilm as disclosed herein.

In various non-limiting embodiments the immobilized biofilm markers include one, two, three, four, or all five of the proteins selected from the group consisting of SEQ ID NO:1 (hypothetical protein 0486), SEQ ID NO:2 (hypothetical protein SAR0056), SEQ ID NO:3 (Glucosaminidase; bifunctional autolysin precursor); SEQ ID NO:13 (lipoprotein ABC transporter protein; accession no. 15923621), and SA0037 (conserved hypothetical protein; SEQ ID NO: 43) from *Staphylococcus aureus*. These proteins have been shown to be associated with biofilm infections as demonstrated below. In one non-limiting embodiment, the one or more immobilized biofilm markers comprises the protein of SEQ ID NO:13 or antigenic fragments thereof. In another embodiment, the one or more immobilized biofilm markers comprises the protein of SEQ ID NO:13 and the protein of SA0037, or antigenic fragments thereof. In another embodiment, the one or more immobilized biofilm markers comprises the protein of SEQ ID NO:13 and the protein of SEQ ID NO:1, or antigenic fragments thereof. In another embodiment, the one or more immobilized biofilm markers comprises the protein of SEQ ID NO:13 and the protein of SEQ ID NO:3, or antigenic fragments thereof. In another embodiment, the one or more immobilized biofilm markers comprises the protein of SEQ ID NO:3 or antigenic fragments thereof. In another embodiment, the one or more immobilized biofilm markers comprises the protein of SEQ ID NO:3 and the protein of SEQ ID NO:1, or antigenic fragments thereof. In another embodiment, the one or more immobilized biofilm markers comprises the protein of SEQ ID NO:13 the protein of SEQ ID NO:1, and the protein of SEQ ID NO:3 or antigenic fragments thereof. Any further such embodiments will be clear to those of skill in the art based on the teachings herein.

In accordance with the instant invention the immobilized biofilm markers can also include any other protein which can serve as a marker of biofilm specific infection. Non-limiting examples of other proteins which could be used as biofilm specific markers are SEQ ID NOS: 4-12 and 14-42 (See, for example, Brady et al. 2006. *Infection and Immunity* 74(6): 3415-3426)

In various non-limiting embodiments the biofilm markers can comprise antigenic portions of the biofilm marker proteins. "Antigenic portions" may be any portion of the protein that elicits an antibody response that is specific for the protein from which the fragment was obtained and to which an antibody can bind.

Detecting binding of the labeled antibody can be accomplished by any suitable means for detecting the label on the labeled antibody including, but not limited to, spectroscopy, absorption, fluorescent detection, surface reflectance, dynamic or static light scattering, surface plasmon resonance, calorimetry, and optical or electron microscopy.

The methods of the invention can be used in accordance with any molecular assay or screening methods suitable for detecting biofilm antibodies including, but not limited to, Enzyme-linked Immunoabsorbant Assay (ELISAs), Lateral Flow Chromatography, and enzyme inhibition assays. In ELISAs the labeled antibodies are contacted to the substrate comprising immobilized biofilm markers. The substrate is then washed to remove unbound labeled antibodies. If biofilm antibodies are present in the test sample, they will form a complex with the biofilm markers immobilized on the substrate, resulting in a remaining detectable signal after completion of the wash. In Lateral Flow Chromatography, the labeled antibodies are contacted to the substrate and then migrate along the substrate to the one or more immobilized biofilm markers. In one embodiment, the biofilm markers are organized in predefined locations on the substrate and organized in a stripe or bar conformation. The labeled biofilm antibodies, if present, bind to the one or more biofilm markers that are immobilized in discrete locations on the substrate. In a non-limiting embodiment, the biofilm antibodies bind to Protein A conjugated to colloidal gold, then the gold-labeled Protein A antibodies migrate along the substrate until reaching the stripe of biofilm markers, where the labeled biofilm antibodies, if present, bind to and form a complex with biofilm specific molecules which results in a detectable colored line, indicating a positive result that biofilm specific antibodies are present in the test sample.

The substrate can optionally comprise immobilized non-specific molecules organized in a separated discrete location, stripe or bar from the biofilm markers. The binding of the labeled antibody to the nonspecific molecules can function as a positive control to determine the proper functioning of the assay.

In a second aspect the invention provides a method for diagnosing biofilm related diseases, comprising:

a) contacting a test sample from a subject with one or more detectably labeled proteins, wherein the one or more detectably labeled proteins are capable of binding antibodies present in the test sample, wherein the binding produces labeled antibodies;

b) contacting the labeled antibodies to a substrate comprising one or more immobilized biofilm markers; wherein the one or more immobilized biofilm markers comprises one or more proteins derived from the group consisting of SEQ ID NO:1, SEQ ID NO:2, SEQ ID NO:3, SEQ ID NO:13, and SEQ ID NO: 43 or antigenic fragments thereof; and c) detecting binding of the labeled antibodies to the one or more immobilized biofilm markers, wherein binding indicates the presence of a biofilm related disease in the subject.

Biofilm related diseases include, but are not limited to, osteomyelitis, endocarditis, chronic rhinosinusitis, chronic lung infections in cystic fibrosis, boils, keratitis, and septicemia, catheter occlusion, biofilm related heart valve defects and medical device failure.

In a third aspect the invention provides a method for diagnosing osteomyelitis, comprising:

a) contacting a test sample from a subject with one or more detectably labeled proteins, wherein the one or more detectably labeled proteins are capable of binding antibodies present in the test sample, wherein the binding produces labeled antibodies;

b) contacting the labeled antibodies to a substrate comprising one or more immobilized biofilm markers; wherein the one or more immobilized biofilm markers comprises one or more proteins derived from the group consisting of SEQ ID NO:1, SEQ ID NO:2, SEQ ID NO:3, SEQ ID NO:13, and SEQ ID NO: 43 or antigenic fragments thereof; and c) detecting binding of the labeled antibodies to the one or more immobilized biofilm markers, wherein binding indicates the presence of osteomyelitis in the subject.

Osteomyelitis is an infection of bone or bone marrow, usually caused by bacteria, most commonly *S. aureus* bacteria. Osteomyelitis often requires prolonged antibiotic therapy, including intravenous antibiotics or surgical debridement. Immunocompromised patients are at a higher risk of developing osteomyelitis. Compromised host resistance can be due to debilitation, HIV, cancer treatment, intravenous drug abuse, or immunosupression therapy used in the treatement of rheumatoid arthritis and to prevent organ rejection after transplant.

In a fourth aspect the invention provides biofilm detection substrates comprising:

a) a test well comprising one or more detectably labeled proteins, wherein the one or more detectably labeled proteins are capable of binding to biofilm antibodies present in a test sample; and b) one or more immobilized biofilm markers capable of binding to labeled antibodies, wherein the one or more immobilized biofilm markers comprises one or more proteins derived from the group consisting of SEQ ID NO:1, SEQ ID NO:2, SEQ ID NO:3, SEQ ID NO:13, and SEQ ID NO: 43.

As used herein "test well" can be any receptacle or substrate suitable for use in the invention, including, but not limited to a container, fiber pad, or membrane The invention also provides a kit for detecting a biofilm specific antibody in a test sample selected from a patient bodily fluids, wherein the kit which comprises the substrates of the fourth aspect of the invention.

The terms, definitions, and embodiments of the first aspect are the same for the second, third and fourth aspects.

EXAMPLE 1

Serum Samples

Serum samples were collected from three New Zealand White female rabbits with methicillin-resistant *Staphylococcus aureus* (MRSA)-induced osteomyelitis as previously described (Brady et al., 2006). This animal model of osteomyelitis have been characterized as a biofilm-specific, chronic infection in rabbits (Brady et al., 2006). Samples were collected from each rabbit before inoculation with MRSA (day 0) and during the chronic stage of infection (day 42). Bone cultures of infected rabbit tibias were performed at the end of this study to confirm the presence of *S. aureus*. Additionally, sera from healthy human subjects were obtained and tested as negative controls for human exposure to MRSA biofilm-specific proteins.

EXAMPLE 2

Purification of Recombinant Biofilm-Specific Proteins

*Escherichia coli* expressing MRSA biofilm proteins lipase (Ag01, Accession No. 28195801; SEQ ID NO:4), hypothetical protein 0486 (Ag02, Accession No. YP_039889; SEQ ID NO:1), or lipoprotein ABC transporter protein (Ag03, Accession No. 15923621; SEQ ID NO:13) were grown while shaking at room temperature in Luria-Bertani (LB) broth with 1 µg/ml ampicillin until $OD_{600}$=0.6. The cells were then induced with 10 µg/ml anhydrotetracycline (IBA, St. Louis, Mo.) and allowed to shake for an additional 3 hours. After induction, the cells were pelleted by centrifugation (3500 rpm for 30 minutes) and resuspended in a periplasmic lysis buffer containing 100 mM Tris/HCl (pH 8), 500 mM sucrose and 1 mM EDTA. After a 30-minute incubation on ice the spheroplasts were centrifuged as before and the lysate was collected for purification.

Lysate containing a recombinant biofilm-specific protein was added to a 5 CV bed volume Strep-tactin flow column (IBA, St. Louis, Mo.) and the protein of interest was purified according to the strep-tag purification protocol. Six elutions of 3 ml each were collected for each protein and western blot analysis was performed to confirm purity. The elutions containing purified protein were concentrated and dialyzed in PBS (pH 7.4) using Microcon 10,000 MWCO filters (Millipore, Billerica, Mass.). Protein concentration was determined using a standard BCA protein assay (Pierce, Rockford, Ill.). This procedure was repeated for each of the three diagnostic protein candidates: Ag01, Ag02, and Ag03.

EXAMPLE 3

Microarray Analysis

Genetic expression of the three proteins in this study were observed in early biofilm growth (8 hr), maturing biofilm (48 hr), and late biofilm (366 hrs). These data were then compared with genetic expression in planktonic log (2 hr), late log (6 hr), and stationary (48 hr) phases. Biofilm to planktonic (non-biofilm) expression ratios of 1.5 or more were considered significantly up-regulated in the biofilm form and ratios of 0.5 or less were considered significantly down-regulated ($P<0.05$).

The microarray data for each gene expressing a biofilm-protein is presented in Table 1. Ag01 expression was slightly up-regulated in early biofilm growth and slightly down-regulated in late biofilm growth when compared to planktonic expression but was not statistically significant. Ag02 expression was up-regulated in early, maturing, and late biofilm stages when compared to planktonic expression. Ag03 was down-regulated in immature biofilms but up-regulated in maturing and late biofilms. Both Ag02 and Ag03 were significantly up-regulated during in vivo biofilm growth and were therefore considered biofilm-specific targets for the development of our Lateral Flow Assay (LFA). While Ag01 was expressed in the biofilm mode of growth, it was also expressed during planktonic growth.

TABLE 1

Microarray data for MRSA gene expression in 8 hr, 48 hr, and 336 hr biofilm compared with 2 hr, 6 hr, and 48 hr planktonic expression.

| | Early Biofilm vs. Planktonic | | | Maturing Biofilm vs. Planktonic | | | Late Biofilm vs. Planktonic | | |
|---|---|---|---|---|---|---|---|---|---|
| | 8 vs. 2 | 8 vs. 6 | 8 vs. 48 | 48 vs. 2 | 48 vs. 6 | 48 vs. 48 | 336 vs. 2 | 336 vs. 6 | 336 vs. 48 |
| Ag01 | 3.49+ | 0.55 | 1.24 | 2.14+ | 0.34− | 0.76 | 1.14 | 0.18− | 0.40− |
| Ag02 | 4.30+ | 2.33+ | 8.11+ | 1.97+ | 1.07 | 3.71+ | 5.49+ | 2.98+ | 10.3+ |
| Ag03 | 1.10 | 0.76 | 0.35− | 3.24+ | 2.25+ | 1.03 | 1.75+ | 1.21 | 0.56 |

+Ratios of biofilm/planktonic expression levels above 1.5 are significantly up-regulated
−Ratios of biofilm/planktonic expression levels below 0.5 are significantly down-regulated ($P < 0.05$)

EXAMPLE 4

Lateral Flow Assay

Figure 2:
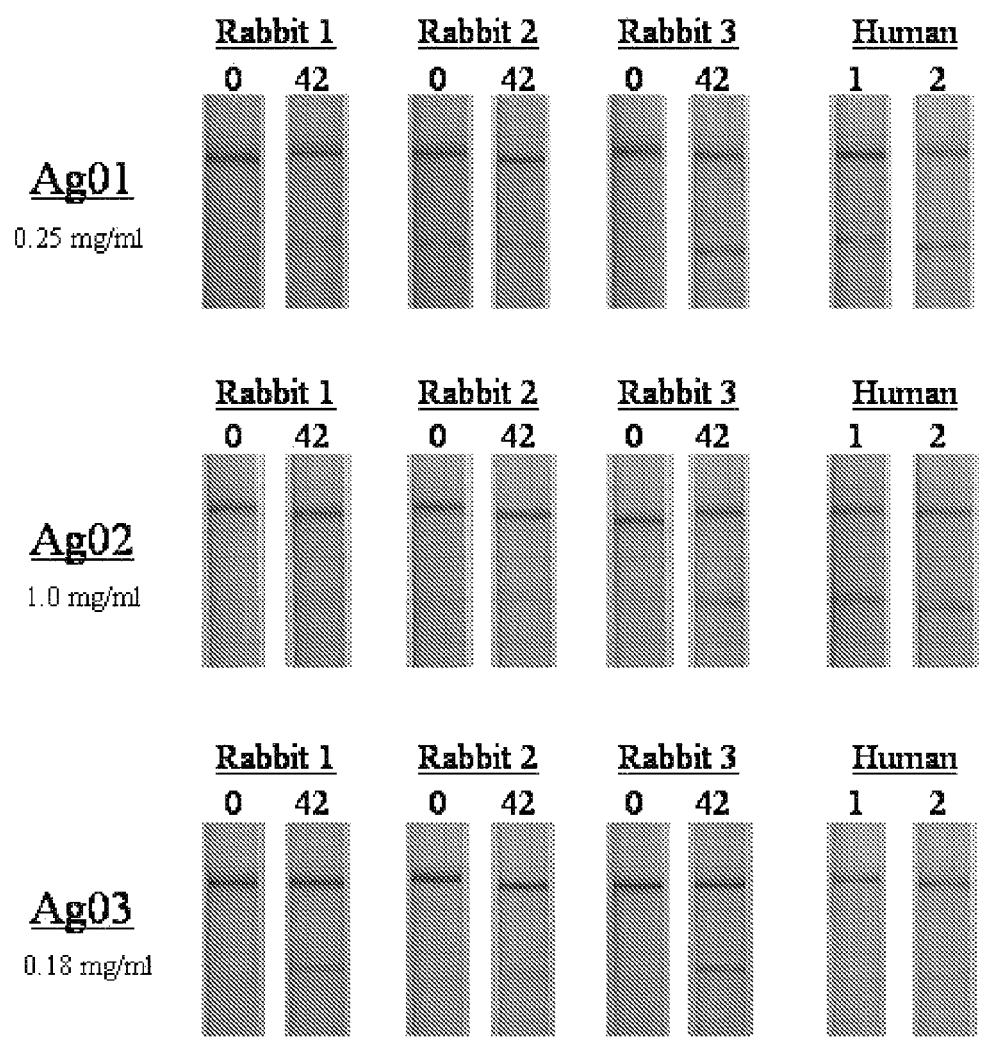
FIG. 2. Results of Lateral Flow Immunoassay in Osteomyelitis.

A control line consisting of a 1/5 anti-protein A antibody (Biomeda, Foster City, Calif.) was striped towards the top of a piece of nitrocellulose. About 1 cm below the control line, Ag01, Ag02, or Ag03 was striped onto the nitrocellulose at concentrations of 0.25 mg/ml, 1.0 mg/ml, and 0.18 mg/ml, respectively. The nitrocellulose was then cut into 0.5 cm×5 cm strips. The distal end of the test strip was saturated with a 1/200 dilution of protein A/colloidal gold (courtesy of Dr. Shang Li) and a 1/100 dilution of rabbit sera in 200 μl of running buffer (50 mM HEPES, 0.35% BSA and 0.1% PEG, pH 7.4). Excess colloidal gold bound at the control line and produced a visible signal that functioned as a positive control for each assay. If the sera contained antibodies against the biofilm proteins a visible line formed at the test line. FIG. 1 depicts a schematic of the lateral flow immunoassay. Six rabbit samples were tested from three rabbits and run in triplicate. Each assay was allowed to run for 10 minutes and results were recorded as positive if two lines were detected visually or negative if only the control line appeared (FIG. 2).

Each of the three protein candidates were striped onto separate pieces of nitrocellulose and the six sera samples, pre-infection sera and 42 days post inoculation, were tested against each antigen in a lateral flow assay system. The percentages of true positives (sensitivity) and true negatives (specificity) were calculated for each assay, and the degree of efficacy was determined. Both the Ag01 and Ag02 LFAs had a sensitivity of 89% and a specificity of 56% (Table 2). In these assays, eight out of nine samples from infected rabbits were positive and five out of nine rabbit pre-infection samples were negative. Additionally, the human sera tested in these assays reacted with the biofilm proteins at the test lines. The Ag03 LFA had a sensitivity and specificity of 100%. All three rabbits before infection were negative and during infection were positive. These results were consistently observed for each repeated trial. Examples of the LFAs using the three proteins as test line candidates are illustrated in FIG. 2.

EXAMPLE 5

ELISA Testing

The wells of a micro-titer plate were coated with 0.3 μg/well protein (Ag01, Ag02, or Ag03) in a coating buffer of 32 mM $Na_2CO_3$ (anhydrous) and 68 mM $NaHCO_3$ and incubated overnight at 4° C. The wells were then blocked with 200 μl/well of PBS containing 0.1% BSA and 0.02% Tween 20 for one hour at room temperature. The blocking buffer was removed and 2-fold serial dilutions were performed for each serum sample (in duplicate) starting with a 1/10 dilution and ending with a 1/1,280 dilution in a diluting buffer of PBS with 0.1% BSA and 0.02% Tween 20. The plates were incubated for 1 hour at room temperature and then washed three times in PBS with 0.4% Tween 20. In each well, 50 μl of a 1/1000 dilution of anti-rabbit-HRP antibody (Pierce, Rockford, Ill.) was added and the plates were incubated for 1 hour at room temperature. The wells were rinsed 3 times with washing buffer. Finally, 50 μl of the chromogenic substrate, 10 ml citrate/phosphate buffer with 10 mg ABTS and 100 μl $H_2O_2$, was added to each well and incubated for 10 minutes at room temperature. Absorbance values were read at 450 nm using an Opsys MR microtiter plate reader. A two-sample paired t-test was performed for each set of sera dilutions to determine if there was a significant difference ($P<0.05$) between infected sera and pre-infected sera in all three rabbits (Table 3).

Figure 3:
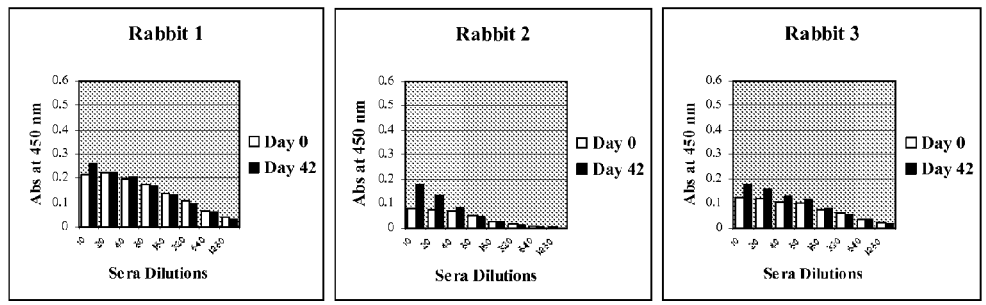
FIG. 3. Results of ELISA Testing in Osteomyelitis. (A) provides ELISA results for Ag01. (B) provides ELISA results for Ag02. (C) provides ELISA results for Ag03.
Figure 3:
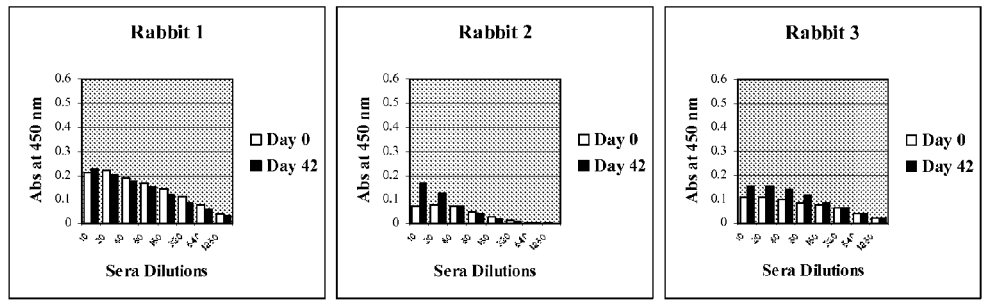
Figure 3:
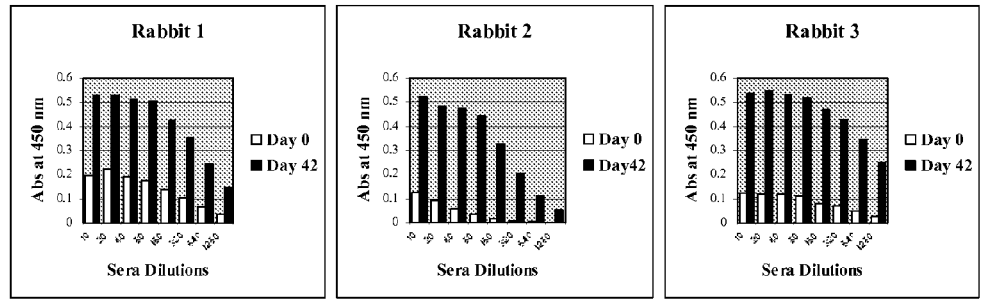

At the 1/10 dilution, all three ELISAs showed a significant elevation in infected sample absorbances from their pre-infected counterparts ($P<0.05$). For the ELISA using Ag01, there was no longer a significant difference between day 0 and day 42 serum samples after the 1/40 dilution. For the ELISA using Ag02, significance was maintained at a 1/10 dilution. Ag03 demonstrated a significance difference from pre-inoculation levels at a dilution of (1/1,280) (Table 3). ELISA results are shown in FIG. 3.

TABLE 2

Summary of results for each LFA. Each rabbit sample was tested three times and sensitivity and specificity were calculated.

| LFA | Concentration | Negative Results True Negative | Negative Results False Negative | Positive Results True Positive | Positive Results False Positive | Sensitivity (%) | Specificity (%) |
|---|---|---|---|---|---|---|---|
| Ag01 | 0.25 mg/ml | 5 | 1 | 8 | 4 | 89 | 56 |
| Ag02 | 1 mg/ml | 5 | 1 | 8 | 4 | 89 | 56 |
| Ag03 | 0.18 mg/ml | 9 | 0 | 9 | 0 | 100 | 100 |

TABLE 3

Summary of ELISA statistics for Ag01, Ag02, and Ag03.

| ELISA | Two-sample paired t-test on 1:10 Dilution | | Titer of least significant difference |
|---|---|---|---|
| | t-value | P-value | |
| Ag01 | 5.81 | 0.0011 | 40 |
| Ag02 | 3.32 | 0.0106 | 10 |
| Ag03 | 21.4 | <0.0005 | 1280+ |

A two-sample paired t-test was performed at each serial dilution set to determine statistical difference between rabbit samples before infection and 42 days post inoculation with MRSA. Titers of the last dilution set demonstrating a significant difference between infected and pre-infected sera samples were determined for each ELISA.

EXAMPLE 6

Biofilm Specific Protein Staining

Biofilms of MRSA were grown in a flow cell for 7 days as described (Brady et al., 2006). After 7 days of growth, biofilms were stained with the nucleic acid dye Syto 9, which stained all biofilm bacteria green, for 20 mins.

Figure 4:
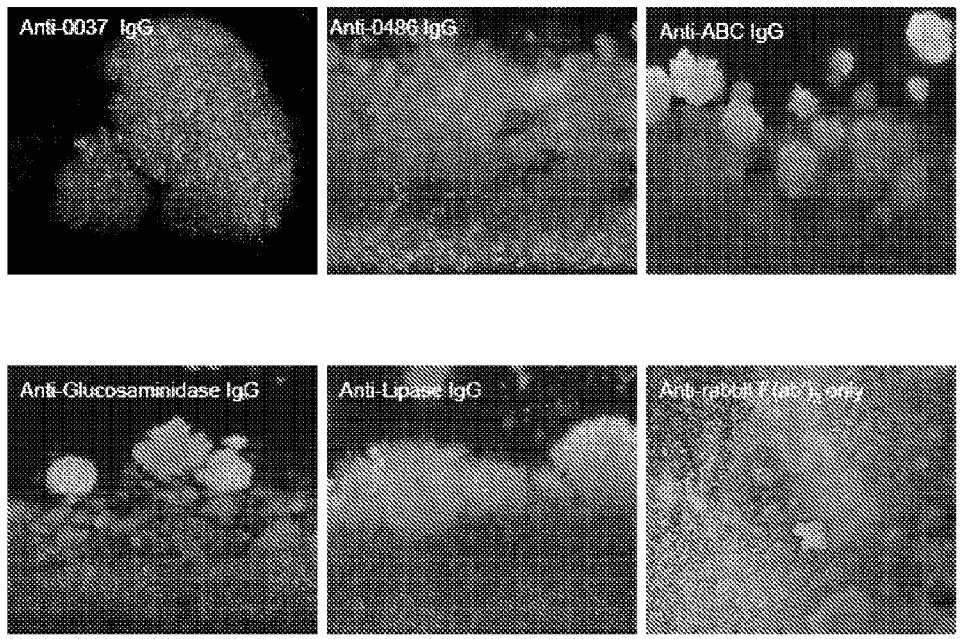
FIG. 4. S. aureus biofilm staining with biofilm specific ligands.

Excess stain was rinsed by flow and antibodies to the specific proteins Glucosaminidase (Accession No. YP_040441; SEQ ID NO:3), Lipase (Accession No. 28195801), hypothetical protein SAR0056 (Accession No. YP_039527; SEQ ID NO:2), 0486 (Ag02, Accession No. YP_039889; SEQ ID NO:1), and ABC transporter protein (Accession No. 15923621; SEQ ID NO:13) were added to the biofilm samples and allowed to bind to their native receptors for 30 mins. Antibody binding was visualized by goat anti-rabbit IgG labeled with PE. Fluorescence, and therefore presence and location of the biofilm-specific antigens, was determined by confocal microscopy (FIG. 4).

EXAMPLE 7

In this example, we created purified, recombinant forms of selected antigens and biofilm up-regulated, cell wall-associated proteins. These proteins were shown to cause a robust polyclonal IgG response when used to immunize rabbits. Antibodies against these recombinant proteins bound to the native forms of each protein as harvested from MRSA in vitro-grown biofilms, both via Western blot and in immunofluorescence confocal microscopy. These IgGs could be utilized as imaging tools that localize to areas of specific protein production within a biofilm. This work illustrates that immunogenic, cell wall-associated, biofilm-upregulated proteins are promising for in vitro visualization of biofilm growth, architecture, and spatial-functional relationships.

Materials and Methods

Organisms.

MRSA strain MRSA-M2, which was isolated from a patient with osteomyelitis at the University of Texas Medical Branch, as well as *Staphylococcus epidermidis* ATCC 35984 were utilized for biofilm growth studies. *Escherichia coli* TOP10 cells were utilized for protein production experiments.

Biofilm Growth Conditions.

MRSA biofilms were grown for all experiments as described in Brady et al. *Infect. Immun.* 74:3415-3426 (2006). For imaging studies, modification of the silicon tubing was made so that 1 mm square glass tubing (Friedrich and Dimmock, Millville, N.J.) was incorporated. *Staphylococcus epidermidis* biofilms were cultured using the same system as for MRSA, with the exception that a 1:10 dilution of CY broth was used without the addition of oxacillin.

Selection of Imaging Targets.

In order to identify biofilm up-regulated genes to pursue as potential imaging targets, microarray analysis was performed comparing biofilm to planktonic growth conditions as in Brady et al. (2006).

Candidate Antigens.

Those proteins that are shown to be immunogenic in our rabbit model of tibial osteomyelitis (Brady et al., 2006) and/or are found to be cell wall-associated by analysis with pSORTb and have been shown to be biofilm-upregulated via microarray analysis were utilized in this work. As well, we selected one antigen whose cellular localization and gene regulation during biofilm growth led us to believe it would serve well as a negative control. For a complete listing of antigens tested refer to Table 4.

TABLE 4

| Candidate antigens | | | | | |
|---|---|---|---|---|---|
| | SA0037 | Lipase | SA0688 | Glucosaminidase | SA0486 |
| Up-regulated during in vitro biofilm | + | – | + | + | + |
| Cell wall associated | + | – | + | + | + |
| Immunogenic in biofilm infection | – | + | + | + | – |

Cloning and Expression of Recombinant Antigens.

Nucleic acid sequences for each protein were obtained using the GenBank™ database and primers were constructed that allowed for amplification of the entire coding region minus the signal sequence (see Table 5).

TABLE 5

Primers and plasmids utilized in this study.

| Primer name | Sequence (5'-3') | Product, size |
|---|---|---|
| 5' SA0037 | ATGAATACAATCAAAACTACGAAA (SEQ ID NO: 44) | Conserved hypo. protein, 519 bp |
| 3' SA0037 | CTTCTCATCGTCATCTGATTTCAAAATCCATTTTGA (SEQ ID NO: 45) | |
| 5' Lipase | ACTCTAGGTCTCACTCCCATCTGAAACAACATTATGACCAAAT (SEQ ID NO: 46) | Lipase, 966 bp |
| 3' Lipase | ATGGTAGGTCTCATATCATAAAGGATTTAACGGTAATTCATTACT (SEQ ID NO: 47) | |

TABLE 5-continued

Primers and plasmids utilized in this study.

| | | |
|---|---|---|
| 5' SA0688 | ATGGTAGGTCTCACTCCGATAAGTCAAATGGCAAACTAAAAGT (SEQ ID NO: 48) | ABC trans. lipoprotein, 860 bp |
| 3' SA0688 | ATGGTAGGTCTCATATCATTTCATGCTTCCGTGTACAGTT (SEQ ID NO: 49) | |
| 5' Glucosaminidase | ATGGTAGGTCTCACTCCGCTTATACTGTTACTAAACCACAAAC (SEQ IDNO: 50) | Glucosaminidase, 1443 bp |
| 3' Glucosaminidase | ATGGTAGGTCTCATATCATTTATATTGTGGGATGTCGAAGTATT (SEQ ID NO: 51) | |
| 5' SA0486 | ACTCTAGGTCTCACTCCAAAGAAGATTCAAAAGAAGAACAAAT (SEQ ID NO: 52) | Hypo. lipoprotein, 683 bp |
| 3' SA0486 | ATGGTAGGTCTCATATCAGCTATCTTCATCAGACGGCCCA (SEQ ID NO: 53) | |

| Plasmid | Genotype or Characteristics | Source |
|---|---|---|
| pBAD-Thio/TOPO | 4454 bp<br>pUC ori, Amp$^R$, pBAD promoter, for arabinose-inducible expression of PCR product<br>3001 bp | Invitrogen Life Technologies |
| pASK-IBA14 | pUC ori, Amp$^R$, tetA promoter, for tetracycline-inducible expression of PCR product | IBA, Göttingen, Germany |

In these experiments, two different expression vectors were used: pASK-IBA14 (IBA, Göttingen, Germany) and pBAD-Thio/TOPO (Invitrogen Life Technologies). Primers used for cloning into pASK-IBA14 contained BsaI restriction sites in the 5' ends (underlined). SA-0037 was cloned into pBAD-Thio/TOPO, as part of the pBAD/TOPO® ThioFusion™ Expression System, and transformed into TOP10 *E. coli* cells (Invitrogen Life Technologies) as per the manufacturer's instructions. The other candidate genes were cloned into pASK-IBA14 using BsaI restriction digestion and transformed into TOP10 *E. coli*. The clones were grown in Luria broth overnight, diluted 1:50, and grown to exponential phase ($A_{600}$~0.5) with shaking (225 rpm). SA0037 was grown at 37° C. while the candidates cloned into pASK-IBA14 were cultured at room temperature. A zero-time sample was taken from each culture, after which exponential phase cultures were supplemented with arabinose (SA0037) at a final concentration of 0.2%. These cultures were allowed to grow for 4 hours for induction. Cultures of lipase, glucosaminidase, SA0688, and SA0486 were induced by the addition of anhydrotetracycline to a final concentration of 0.2 µg/ml. These cultures were allowed to continue shaking at room temperature for 3 hours as per the manufacturer's directions. Cells were collected by centrifugation at 12,000×g.

Purification of recombinant SA0037. As SA0037 was found to be an insoluble protein (data not shown), we utilized the ProBond Purification System (Invitrogen Life Technologies, as per the manufacturer's instructions) with hybrid purification conditions. The protein was purified using the ProBond Purification System's nickel columns, the fractions ("protein-stripped" supernatant, washes, and eluate) were all retained, and samples thereof were resolved on a SDS-PAGE gel to assure that purification was complete and that all of the recombinant protein was being retained in the eluate (data not shown). Eluted protein was then dialyzed against PBS using Slide-A-Lyzer 3500 MWCO dialysis membranes (Pierce Biotechnology, Rockford, Ill.).

Purification of Recombinant Lipase, SA0688, Glucosaminidase, and SA0486.

Cells were pelleted and lysed through the addition of Buffer P (100 mM Tris/HCl pH8, 500 mM sucrose, 1 mM EDTA) and incubation on ice for 30 minutes. A 10 µl sample was removed for analysis to ensure that protein induction was successful. Spheroplasts were removed by centrifugation at 13,000 rpm for 5 minutes. The supernatant was retained (containing the periplasmic proteins), and a 10 µl sample of the spheroplasts was retained for comparison of the target protein's periplasmic vs. cytoplasmic localization. The target protein was then purified using Strep-Tactin Spin Columns (IBA, Göttingen, Germany) as per the manufacturer's instructions. At each step, 10 µl aliquots were retained for subsequent SDS-PAGE analysis. Proteins were eluted from the columns via the addition of 3, 150 µl volumes of Buffer BE (Biotin Elution Buffer; 100 mM Tris•Cl, 150 mM NaCl, 1 mM EDTA, 2 mM D-biotin, pH 8), in order to allow for maximum protein yield. The eluted proteins were then concentrated approximately 10× using Centricon Centrifugal Filters with a 10,000 MWCO (Millipore, Billerica, Mass.).

Polyclonal IgG Production.

Purified recombinant antigen (10 µg) was combined with Titermax Gold® adjuvant and mixed via sonication. Each antigen was then injected intramuscularly into 8 week old female New Zealand White rabbits. Rabbits were bled prior to immunization as a negative control. Booster immunizations were administered two times at 10 day intervals. Ten days after the second boost, animals were bled again. IgG was harvested from the serum via the Melon Gel® IgG Purification Kit (Pierce Biotechnology, Rockford, Ill.) according to the manufacturer's instructions, and IgG ammonium precipitated overnight. The precipitated IgG was resuspended and dialyzed three times against 1× Melon Gel® Purification Buffer. Purified IgG was quantified using the modified method of Bradford et al., Anal. Biochem. 72:248-254 (1976).

Western Blotting.

In order to determine if the purified, recombinant proteins were eliciting a robust IgG response upon vaccination, 5 µg of each protein were resolved on SDS-PAGE gels. The protein was then transferred to PVDF membranes and immunoblotted using the appropriate polyclonal IgG at a 1:100 dilution. Goat anti-rabbit IgG with a horseradish peroxidase tag was utilized as a secondary antibody at a 1:5000 dilution. Western blots were visualized using a chemiluminescent substrate (SuperSignal, Pierce Biotechnologies).

To analyze the ability of the purified recombinant forms of the proteins to react with serum from animals suffering from MRSA biofilm infections, each protein was resolved and transferred as above, and serum from our animal model of osteomylitis was used as the primary antibody.

In order to determine if IgG created against the purified recombinant forms of these proteins could effectively bind to their cognate proteins found in the biofilm mode of growth, total biofilm protein as well as cell wall and protoplast fractions were resolved using SDS-PAGE, and transferred to PVDF. These membranes were then probed using purified anti-recombinant IgG at a 1:100 dilution and goat anti-rabbit IgG-HRP at a 1:5000 dilution as a secondary antibody, with SuperSignal applied for visualization.

In Vitro IgG Immunofluorescence Experiments.

In order to evaluate the ability of the anti-recombinant IgGs to bind to their cognate proteins in their native forms within an intact biofilm, we grew 14 day MRSA or *S. epidermidis* biofilms as described above with the modification that a flow cell was inserted into the silicon tubing. After 14 days, the tubing on either side of each flow cell was clamped and the flow cell was excised. The biofilm cells were not fixed or embedded in any way prior to immunofluorescence. The cells were flushed with PBS-3% BSA and then the polyclonal IgG was injected into the flow cell and incubated at room temperature for 45 minutes. IgG for each candidate antigen was used in separate experiments: IgG was diluted according to normalization to anti-lipase diluted 1:100 into PBS-1% BSA. The flow cell was flushed by injecting PBS-3% BSA, followed by incubation with a 1:200 (10 μg/ml) dilution of Alexa Fluor 633-conjugated goat anti-rabbit F(ab')$_2$ (Invitrogen) in the dark for 45 minutes. The flow cells were again flushed with PBS-3% BSA. SYTO 9 DNA intercalating stain (Invitrogen) was applied at 3.34 nM in order to stain all cells within the biofilm, and allowed to incubate in the dark for 15 minutes. Confocal laser scanning microscopy (CLSM) was employed to visualize the biofilm and binding of the candidate IgG via fluorescence using a Zeiss LSM510 Metalaser scanning confocal microscope. This microscope was not inverted. The microscope was configured with 2 lasers (Argon 488 nm/514 nm/543 nm and HeNe 633 nm), and micrographs were taken at random with the Plan-Apochromat 63×/1.4 oil immersion DIC objective. Filters were set to a bandpass of 505-530 nm for visualization of SYTO 9 and a longpass of 650 nm for visualization of the conjugated antibody. The sections examined were all approximately 40 μm thick as determined by the LSMix software (Zeiss).

Results

Figure 5:
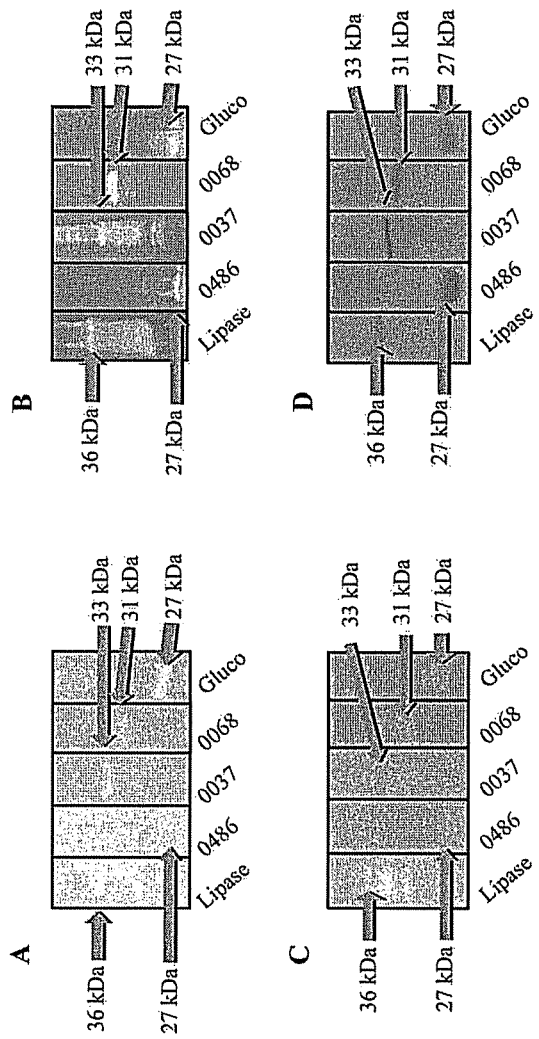
FIG. 5. Purified recombinant proteins elicit a strong antibody response. (A) Purified recombinant proteins were run on a SDS-PAGE gel and probed with convalescent serum from the biofilm infection model. (B) Purified recombinant proteins were run on a SDS-PAGE gel and probed with serum drawn from rabbits vaccinated with individual recombinant proteins. (C) Total protein from the cell wall fraction of an in vitro grown biofilm were run on a SDS-PAGE gel and probed with serum drawn from rabbits immunized with individual recombinant proteins. Arrows point to bands corresponding to the molecular masses of lipase, SA0486, SA0037, SA0688, and glucosaminidase predicted to be 36, 27, 33, 31, and 27 kDA, respectively.

Immunogenicity of candidate proteins. In the work presented herein, we wished to attempt to visualize MRSA biofilms grown in vitro using IgG antibodies specifically targeted to these proteins. Thus, we generated purified, recombinant forms of each protein in order to produce IgG in rabbits. In order to determine if the epitope structure of the purified recombinant form of each protein matched well with that of the proteins found within the biofilm, an aliquot (5 μg) of each recombinant protein was resolved via SDS-PAGE and proteins were transferred to a PVDF membrane. The membrane was then immunoblotted with serum from our rabbit model of osteomyelitis infection (FIG. 5A). All but SA0486 robustly reacted with this serum. Therefore, it can be assumed that the recombinant form of the protein is able to be recognized by antibodies directed against the native protein produced during a biofilm infection. With respect to SA0486, this antigen may not elicit a significant antibody response in an in vivo infection due to competition with other antigens. However, due to its high levels of up-regulation and its localization to the cell wall, we thought it could still be quite useful as a potential imaging target.

Polyclonal Antibody Production and Analysis.

The recombinant proteins were injected into rabbits (10 μg per injection combined with Titermax Gold® adjuvant, three injections, each 10 days apart) and serum was collected. Polyclonal antibodies to each protein showed a strong, specific response to both the recombinant protein and the cognate protein from MRSA in vitro biofilms via Western blot (FIG. 5B). Preimmune serum did not react with the recombinant proteins or total biofilm protein (data not shown). IgG against each recombinant protein was isolated from whole serum via the Melon™ Gel IgG Purification Kit (Pierce, Rockford, Ill.), ammonium precipitated, and dialyzed. When these antibodies were tested against total protein from the cell wall fraction of an in vitro biofilm separated by SDS-PAGE, they bound to proteins that corresponded to the molecular weight of the native protein (FIG. 5C). Therefore, it can be assumed that the recombinant forms of the candidate antigens effectively mimic the in vivo and in situ properties of the native form.

Recombinant SA0486 was not recognized by antibodies directed against the native protein produced during a biofilm infection (FIG. 5A). There are several reasons why this may be occurring. First, there may have been a less than robust immune response to SA0486 in vivo, as this protein may be hidden within the biofilm. However, although an immune response to this antigen may not develop in a biofilm, IgG has been shown previously in our laboratory as well as by others to flow freely through the exopolysaccharide matrix. Therefore, this does not prevent this gene product being used as a potential imaging target. Also, while we saw significantly higher expression of the SA0486 gene in biofilm growth in vitro (via microarray analysis) compared to planktonic growth, the expression levels in vivo may not match. Therefore, there may be relatively low levels of SA0486 protein present during infection, and thus, a lesser immune response. Regardless, when we performed the converse study, SA0486 protein, as isolated from the biofilm, was bound strongly by its anti-recombinant IgG antibody (FIG. 5C). This illustrates that, even though this protein was non-immunogenic in vivo, it is still able to be targeted by anti-SA0486 IgG. The high levels of binding seen also indicate that this protein is present in high levels within the biofilm, at least in vitro.

In Vitro Visualization of MRSA Biofilms Using Anti-Recombinant IgG.

Figure 6:
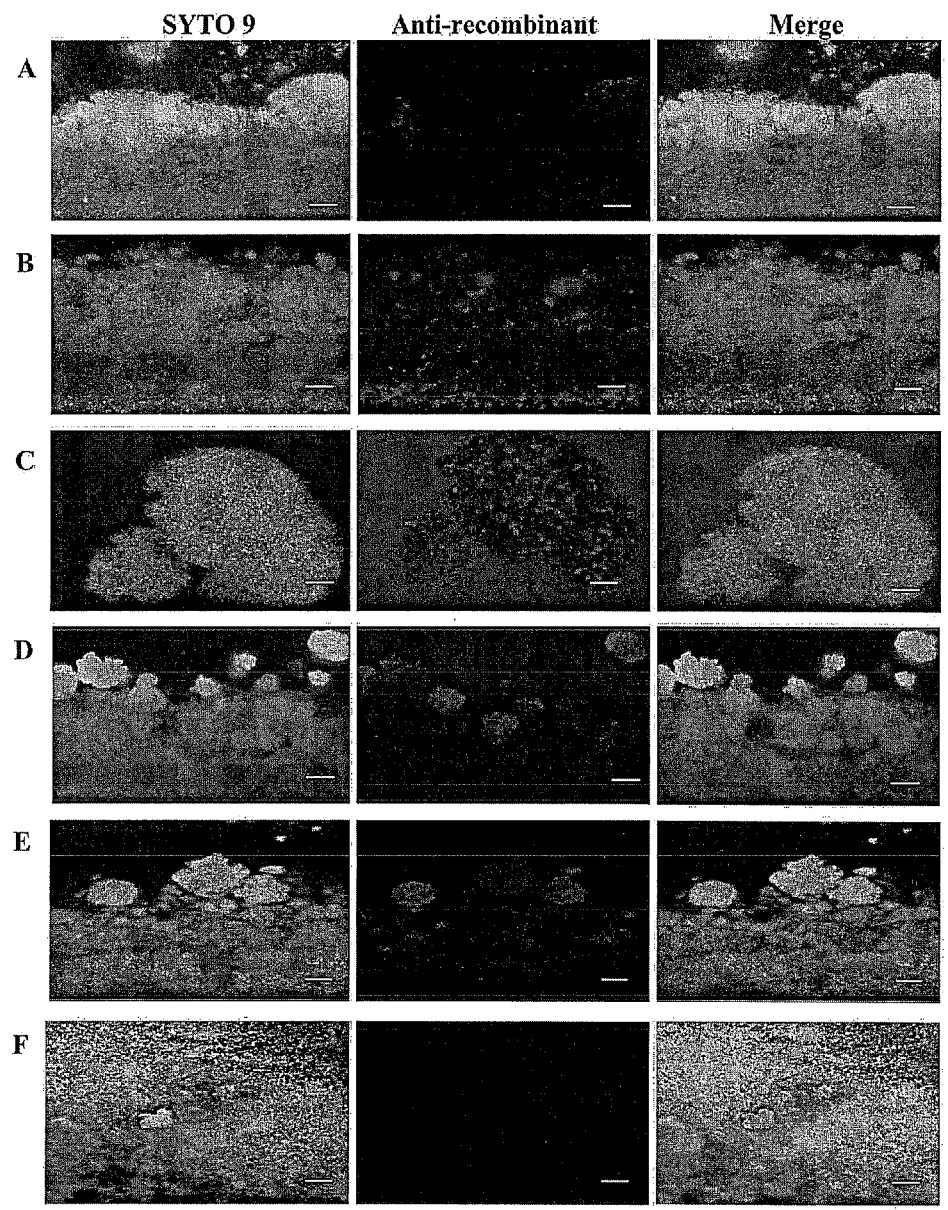
FIG. 6. IgGs against recombinant forms of cell wall-associated biofilm proteins bind to intact MRSA biofilms. MRSA biofilms were grown and IgG against each selected candidate protein was applied (A-E), followed by the secondary goat anti-rabbit F(ab')$_2$ (A-F). After washing, SYTO9 was applied to stain all bacterial cells. Biofilms were probed with A: anti-lipase IgG and secondary; B: anti-SA0486 IgG and secondary; C: anti-SA0037 IgG and secondary; D: anti-SA0688 IgG and secondary; E: anti-glucosaminidase IgG and secondary; F: secondary alone (F(ab')$_2$ only [negative control]). The base of the glass is located at the bottom of each image and each image is a cross-sectional view of the biofilm from the base into the lumen. Size bar=20 μm.

We next applied the resulting IgG to a 14-day in vitro-grown *S. aureus* biofilm. A *S. aureus* biofilm was cultured as discussed in Brady 2006, with the modification of using 1 meter sections of silicon tubing with square flow cells. The flow cell was flushed followed by incubation with specific antibodies and then Alexa Fluor 633 goat anti-rabbit F(ab')$_2$ (Invitrogen). SYTO 9 DNA intercalating stain was also applied in order to stain all cells within the biofilm. Confocal laser scanning microscopy (CLSM) was employed to visualize the biofilm and binding of the candidate IgG via fluorescence. As is evident in FIG. 6, IgG against proteins that are cell wall-associated and were found, via microarray analysis, to be up-regulated in a biofilm (recombinant SA0486, SA0037, glucosaminidase, and SA0688) bound strongly to the intact MRSA biofilm. However, IgG against the gene product that has a low level of secretion into the flowing media (lipase) did not bind. This illustrates that cell wall-associated proteins that are found at increased levels in the biofilm can be targeted for specific binding by polyclonal IgG. The lack of binding by anti-lipase IgG also demonstrates that the binding by the other IgGs are not due to nonspecific binding to Protein A. The lack of reactivity when only secondary antibody was applied (FIG. 6F) also shows that the binding of the antibodies against biofilm-associated antigens is specific.

Specificity of Some Anti-Recombinant IgG to *S. aureus* Biofilms.

We also applied these antibodies to *S. epidermidis* biofilms in order to determine the specificity of each IgG to *S. aureus*. While the anti-glucosaminidase, anti-SA0688, and anti-lipase IgGs were unable to bind to *S. epidermidis*, the IgGs against the highly conserved proteins of SA0486 did specifically bind the biofilm, and anti-SA0037 IgG bound weakly. This allows us to conclude that anti-glucosaminidase and anti-SA0688 IgGs bind specifically to *S. aureus*. Anti-SA0037 and anti-SA0486 IgGs may be *Staphylococcus* genus specific.

Discussion

In this work, antibodies that were cell wall-associated, biofilm-upregulated, antigenic proteins, allowed for the visualization of not only the architecture of the *S. aureus* biofilm, but also the expression patterns of the target antigens from the observed staining patterns.

The target antigens chosen for this study included one of the two components of autolysin (glucosaminidase) and an uncharacterized ABC transporter lipoprotein (SA0688). *S. aureus* contains cell wall-associated virulence factor Protein A. This protein effectively binds to the Fc portion of mammalian IgG as an immunoavoidance strategy. Since the present study is designed to utilize IgG against MRSA biofilm antigens, the IgG-binding ability of Protein A may reduce the ability to specifically target certain antigens. Therefore, antibodies against lipase, a secreted antigen that was not significantly up-regulated in a biofilm, were developed as a negative control. As well, two candidates that were previously shown in our lab to be cell wall or membrane-associated and up-regulated in biofilm conditions were studied for their possible immunogenic potential. These two antigens were not found in previous screening studies to be immunogenic. However, due to their highly increased transcriptomic levels and their localization to the cell wall, we believed these proteins could indeed be immunogenic but not seen in previous experiments due to shielding by the extracellular matrix, which could lead to a less robust B cell response. These include SA0037, a conserved hypothetical protein and SA0486, an uncharacterized lipoprotein. All antigens tested were present in all screened strains.

In order to confirm the similarity of the epitope structure of the recombinant forms of the antigens, as well as to verify the cell wall localization of SA0037 and SA0486, we first undertook a simple Western blot study in which we tested the ability of the recombinant proteins to react with serum from a rabbit model of tibial osteomyelitis. The strong reactivity of rLipase, rSA0688, and rGlucosaminidase with the convalescent serum confirms previous information. rSA0037 was also reactive with this serum, meaning that SA0037 is immunogenic during *S. aureus* biofilm infection and indicates that the protein is exposed to the immune response at some point during the infection, though protein mapping tools (i.e., pSORT) give an unknown localization.

However, rSA0486 was not reactive with the convalescent sera (FIG. 5A). This means SA0486, which has a known cell wall association, was not immunogenicity during an in vivo infection. This lack of immunogenicity may have been due to the protein being hidden within the biofilm or masked by another antigen. Nevertheless, SA0486 can still be used as an imaging target since IgG to the recombinant antigen was able to freely flow through the exopolysaccharide matrix and interact with the native form of SA0486 during these in vitro studies.

Although SA0486 transcript levels may have been higher as shown by earlier microarray studies, this may not necessarily reflect translated products. As a target for a possible imaging tool, this also may not be an issue, as any SA0486 that is present should be bound by the antibody. Regardless, when we performed the converse study, both SA0037 and SA0486 proteins, as isolated from the biofilm, were bound strongly by their respective anti-recombinant IgG antibodies (FIG. 5C). This shows that, in the case of SA0037, its localization is on the outer portion of the cell, and thus tells us information about its localization that was previously unattainable. For SA0486, these results illustrate that, even though this protein was non-immunogenic in vivo, it is still able to be targeted by anti-SA0486 IgG. The high levels of binding seen also indicate that this protein is present in high levels within the biofilm, at least in vitro. Thus we hypothesized that SA0486 may still be a worthwhile target for imaging.

In the final part of this work, the ability of the anti-recombinant antibodies to bind to their cognate proteins within an intact, mature *S. aureus* biofilm grown in vitro was monitored. In these experiments, antibodies generated against purified, recombinant forms of *S. aureus* biofilm proteins bound to those proteins in their native form in an intact biofilm. To our knowledge, this is the first report to show in situ binding to specific cell localized biofilm-associated proteins.

This is also the first report that utilized immunofluorescence to give functional and spatial information about the proteins within the biofilm itself. As is evident in FIG. 6, the staining of the *S. aureus* biofilm with each of the reactive IgG antibodies is quite different. Anti-SA0486 antibodies stain the entire biofilm. However, anti-SA0688 and anti-glucosaminidase antibodies stained individual microcolonies within the biofilm, while other microcolonies were not stained at all. Anti-SA0037 IgG stained individual cells within each microcolony, giving a punctate staining pattern. Therefore, the antibodies we used in this study demonstrate that the chosen candidate proteins are being produced in the biofilm and are present on the cellular envelope. In addition, they provide insight into where their target proteins are being expressed within the biofilm. For example, it is evident that glucosaminidase is only being produced in some microcolonies, and its expression is not homogenous throughout the biofilm structure. This protein is part of the autolysin Atl and is involved in peptidoglycan hydrolysis. Because peptidoglycan cleavage will occur at high levels within cells that are actively replicating and dividing, it may be that the microcolonies where we see positive staining with anti-glucosaminidase IgG are microcolonies in which the cells are actively dividing. In addition, cellular metabolism may be high in certain microcolonies. Therefore, the specific microcolony staining pattern with the anti-SA0688 IgG may demonstrate that this ABC transporter lipoprotein is expressed in microcolonies that are metabolically active. The extremely punctate staining of anti-SA0037 antibodies is of specific interest. However, we are unable to speculate to the role of SA0037 based on this staining, as there are no known proteins with any homology to it that have a described function.

Finally, we also attempted to visualize the closely related *S. epidermidis* biofilm with the same antibodies in order to test the specificity of our anti-recombinant IgGs. While anti-glucosaminidase and anti-SA0688 IgG did not bind to *S. epidermidis*, anti-SA0037 bound weakly and anti-SA0486 bound strongly. Thus, we do see specificity of some of our antibodies for *S. aureus* biofilms. Another interesting aspect to the microscopy results show that homologous proteins from different species may have high sequence identity but have markedly different epitope presentation. For example, BlastP shows 61% identity between *S. aureus* and *S. epidermidis* glucosaminidase sequences, and the anti-*S. aureus* glucosaminidase IgG does not bind to *S. epidermidis* biofilms. Conversely, other, lesser related proteins have similar epitope presentation, such as is the case with SA0486. Anti-*S. aureus* SA0486 IgG does bind to *S. epidermidis* biofilms, and yet the similarity between this protein between the two species is only 50%. Thus, the specificity of binding to *S. aureus* vs. *S. epidermidis* may have more to do with temporal expression of these proteins or specific epitopes on the outside of the cells that are disparate between the species. These antibodies were applied to a gram-negative biofilm as well, in order to test specificity to the *Staphylococcus* genus in general. When we utilized *Pseudomonas aeruginosa* in a 14 day biofilm, we only saw relatively weak non-specific binding of all antibodies, including our secondary F(ab')$_2$ alone (data not shown) due to a small proportion of the antibodies collecting in the PAO1 biofilm matrix. Therefore, the fidelity of the IgGs against staphylococcal antigens was demonstrated since they did not interact with homologous proteins in *P. aeruginosa*. Thus we were able to show that anti-glucosaminidase and anti-SA06988 IgGs are useful to image *S. aureus* while other IgGs are cross-reactive with epitopes expressed in *S. epidermidis*. However, our focus of interest is in *S. aureus* biofilms grown in vitro. This research could be expanded to include antibodies generated against the recombinant forms of *S. epidermidis* proteins to pursue the investigation of those proteins' expression within the biofilm of that species.

Overall, the work presented herein supports the method that recombinant forms of biofilm up-regulated, cell wall and membrane-associated proteins can be used to create IgG antibodies to be used as imaging tools that are specific to *S. aureus* biofilms. As well, this study also begins to delve into functional research regarding the expression patterns of *S. aureus* biofilm proteins within the biofilm architecture. This data could have useful applications in dissecting the various microniches within the entirety of the biofilm, work which could be extremely important in further understanding how these structures form and persist. Lastly, these IgGs may also have great promise for use as in vivo diagnostics; research into utilizing these antibodies in this way is ongoing in our laboratory.

REFERENCES

Brady, R. A., Leid, J. G., Camper, A. K., Costerton, J. W. and Shirtliff, M. E., 2006. Identification of *Staphylococcus aureus* proteins recognized by the antibody-mediated immune response to a biofilm infection. Infect. Immun. 74, 3415.

Cosgrove, S. E., Qi, Y., Kaye, K. S., Harbarth, S., Karchmer, A. W. and Carmeli, Y., 2005. The impact of methicillin resistance in *Staphylococcus aureus* bacteremia on patient outcomes: mortality, length of stay, and hospital charges. Infect. Control Hosp. Epidemiol. 26, 166.

Costerton, W., Veeh, R., Shirtliff, M., Pasmore, M., Post, C. and Ehrlich, G., 2003. The application of biofilm science to the study and control of chronic bacterial infections. J. Clin. Invest. 112, 1466.

Jefferson, K. K., Goldmann, D. A., Pier, G. B., 2005. Use of confocal microscopy to analyze the rate of vancomycin penetration through *Staphylococcus aureus* biofilms. Antimicrob Agents Chemother. 49, 2467.

Jesaitis, A. J., Franklin, M. J., Berglund, D., Sasaki, M., Lord, C. I., Bleazard, J. B., Duffy, J. E., Beyenal, H. and Lewandowski, Z., 2003. Compromised host defense on *Pseudomonas aeruginosa* biofilms: characterization of neutrophil and biofilm interactions. J. Immunol. 171, 4329.

Kobayashi, N., Bauer, T. W., Tuohy, M. J., Fujishiro, T. and Procop, G. W., 2007. Bried ultrasonication improves detection of biofilm-formative bacteria around a metal implant. Clin. Orthop. Relat. Res. 457, 210.

Lambert, P. A., Krikler, S. J., Patel, R., Parvathan, S., 1992. Enzyme-linked immunosrobent assay for the detection of antibodies to exocellular proteins of *Staphylococcus aureus* in bone infection. FEMS Microbiology Letters. 100, 67.

Leid, J. G., Costerton, J. W., Shirtliff, M. E., Gilmore, M. S. and Engelbert, M., 2002a. Immunology of Staphylococcal biofilm infections in the eye: new tools to study endophthalmitis. DNA Cell Biol. 21, 405.

Leid, J. G., Shirtliff, M. E., Costerton, J. W., Stoodley, P., 2002b. Human Leukocytes Adhere to, Penetrate, and Respond to *Staphylococcus aureus* Biofilms. Infect. Immun. 70, 6339.

Leid, J. G., Willson, C. J., Shirtliff, M. E., Hassett, D. J., Parsek, M. R. and Jeffers, A. K., 2005. The exopolusaccharide alginate protects *Pseudomonas aeruginosa* biofilm bacteria from IFN-gamma-mediated macrophage killing. J. Immunol. 175, 7512.

Mack, D., Rohde, H., Harris, L. G., Davies, A. P., Horskotte, M. A., Knobloch, J. K., 2006. Biofilm formation in medical device-related infection. Int. J. Artif. Organs. 29, 343.

O'Toole, G., Kaplan, H. B., Kolter, R., 2000. Biofilm Formation as Microbial Development. Annu Rev. Microbiol. 54, 49.

Parsek, M. R. and Singh, P. K., 2003. Bacterial Biofilms: An Emerging Link to Disease Pathogenesis. Annu Rev. Microbiol. 57, 677.

Sanderson, A. R., Leid, J. G., Hunsaker, D., 2006. Bacterial biofilms on the sinus mucosa of human subjects with chronic rhinosinusitis. Laryngoscope. 116, 1121.

Selan, L., Passariello, C., Rizzo, L., Varesi, P., Speziale, F., Renzini, G., Thaller, M. C., Fiorani, P. and Rossolini, G. M., 2002. Diagnosis of vascular graft infections with antibodies against staphylococcal slime antigens. Lancet. 359, 2166.

Shirtliff, M. E., Mader, J. T., Camper, A. K., 2002. Molecular interactions in biofilms. Chem. Biol. 9, 859.

Trampuz, A. and Zimmerli, W., 2006. Diagnosis and treatment of infections associated with fracture-fixation devices. Injury. 37, S59.

Tyski, S., Colgue-Navarro, P., Hryniewicz, W., Granstrom, M. and Mollby, R., 1991. Lipase versus teichoic acid and alpha-toxin as antigen in an enzyme immunoassay for serological diagnosis of *Staphylococcus aureus* infections. Eur. J. Clin. Microbiol. Infect. Dis. 10, 447.

Veeh, R. H., Shirtliff, M. E., Petik, J. R., Flood, J. A., Davis, C. C., Seymour, J. L., Hansmann, M. A., Kerr, K. M., Pasmore, M. E. and Costerton, J. W., 2003. Detection of *Staphylococcus aureus* biofilm on tampons and menses components. J. Infect. Dis. 188, 519.

Watkin, R. W., Lang, S., Lambert, P. A., Littler, W. A., Elliot, T. S., 2006. The serological diagnosis of staphylococcal infective endocarditis. J. Infect. 53, 301.

Ymele-Leki, P. and Ross, J. M., 2007. Erosion from *Staphylococcus aureus* biofilms grown under physiologically relevant fluid shear forces yields bacterial cells with reduced avidity to collagen. Appl. Environ. Microbiol. 73, 1834.

We claim:

1. A method for detecting a probability for the presence of a *Staphylococcus* biofilm comprising:
   a) contacting a test sample with one or more detectably labeled proteins,
      wherein the one or more detectably labeled proteins are capable of binding antibodies present in the test sample, wherein the binding produces labeled antibodies;
   b) contacting the labeled antibodies to a substrate comprising one or more immobilized biofilm markers selected from the group consisting of SEQ ID NO:1, SEQ ID NO:2, SEQ ID NO:3, SEQ ID NO:13, SEQ ID NO: 43 and a polypeptide comprising one or more antigenic fragments thereof; and
   c) detecting binding of the labeled antibodies to the one or more immobilized biofilm markers, wherein binding indicates a probability for the presence of the *Staphylococcus* biofilm in the test sample.

2. The method of claim 1 wherein the contacting the labeled antibodies to a substrate comprises allowing the labeled antibodies to migrate along the substrate prior to contacting the one or more immobilized biofilm markers.

3. The method of claim 1 wherein the biofilm comprises *Staphylococcus aureus*.

4. The method of claim 3 wherein the *Staphylococcus aureus* comprises methicillin-resistant *Staphylococcus aureus*.

5. A method for diagnosing a probability for the presence of a *Staphylococcus* biofilm related disease in a subject, comprising:
   a) contacting a test sample from the subject with one or more detectably labeled proteins, wherein the one or more detectably labeled proteins are capable of binding antibodies present in the test sample, wherein the binding produces labeled antibodies;
   b) contacting the labeled antibodies to a substrate comprising one or more immobilized biofilm markers selected from the group consisting of SEQ ID NO:1, SEQ ID NO:2, SEQ ID NO:3, SEQ ID NO:13, SEQ ID NO: 43 and a polypeptide comprising one or more antigenic fragments thereof; and
   c) detecting binding of the labeled antibodies to the one or more immobilized biofilm markers, wherein binding indicates a probability for the presence of a *Staphylococcus* biofilm related disease in the subject.

6. The method of claim 5, wherein the biofilm related disease is osteomyelitis.

7. Biofilm detection substrates for detecting a probability for the presence of a *Staphylococcus* biofilm comprising:
   a) a test well comprising one or more detectably labeled proteins, wherein the one or more detectably labeled proteins are capable of binding to biofilm antibodies present in a test sample; and
   b) one or more immobilized *Staphylococcus* biofilm markers capable of binding to labeled antibodies selected from the group consisting of SEQ ID NO: 1, SEQ ID NO:2, SEQ ID NO:3, SEQ ID NO:13, SEQ ID NO: 43 and a polypeptide comprising one or more antigenic fragments thereof.

8. A kit for detecting a probability for the presence of a *Staphylococcus* biofilm comprising the substrates of claim 7, wherein the one or more detectably labeled proteins of a) are capable of binding to biofilm antibodies present in a test sample, wherein the test sample is a bodily fluid sample from a patient.

9. The method of claim 1, wherein the one or more immobilized biofilm markers of b) is SEQ ID NO:1 or a polypeptide comprising one or more antigenic fragments thereof.

10. The method of claim 1, wherein the one or more immobilized biofilm markers of b) is SEQ ID NO:2 or a polypeptide comprising one or more antigenic fragments thereof.

11. The method of claim 1, wherein the one or more immobilized biofilm markers of b) is SEQ ID NO:3 or a polypeptide comprising one or more antigenic fragments thereof.

12. The method of claim 1, wherein the one or more immobilized biofilm markers of b) is SEQ ID NO:13 or a polypeptide comprising one or more antigenic fragments thereof.

13. The method of claim 1, wherein the one or more immobilized biofilm markers of b) is SEQ ID NO:43 or a polypeptide comprising one or more antigenic fragments thereof.

14. The method of claim 5, wherein the one or more immobilized biofilm markers of b) is SEQ ID NO:1 or a polypeptide comprising one or more antigenic fragments thereof.

15. The method of claim 5, wherein the one or more immobilized biofilm markers of b) is SEQ ID NO:2 or a polypeptide comprising one or more antigenic fragments thereof.

16. The method of claim 5, wherein the one or more immobilized biofilm markers of b) is SEQ ID NO:3 or a polypeptide comprising one or more antigenic fragments thereof.

17. The method of claim 5, wherein the one or more immobilized biofilm markers of b) is SEQ ID NO:13 or a polypeptide comprising one or more antigenic fragments thereof.

18. The method of claim 5, wherein the one or more immobilized biofilm markers of b) is SEQ ID NO:43 or a polypeptide comprising one or more antigenic fragments thereof.

19. The biofilm detection substrates of claim 7, wherein the one or more immobilized biofilm markers of b) is SEQ ID NO:1 or a polypeptide comprising one or more antigenic fragments thereof.

20. The biofilm detection substrates of claim 7, wherein the one or more immobilized biofilm markers of b) is SEQ ID NO:2 or a polypeptide comprising one or more antigenic fragments thereof.

* * * * *

UNITED STATES PATENT AND TRADEMARK OFFICE
CERTIFICATE OF CORRECTION

| | | |
|---|---|---|
| PATENT NO. | : 8,541,006 B2 | |
| APPLICATION NO. | : 12/671398 | |
| DATED | : September 24, 2013 | |
| INVENTOR(S) | : Jeffrey G. Leid et al. | |

It is certified that error appears in the above-identified patent and that said Letters Patent is hereby corrected as shown below:

IN THE SPECIFICATION

In Column 1, lines 17-22, delete "Portions of this work were supported by Allergy and Infectious Diseases, National Institutes of Health, under contract number N01-AI-15447 and by the National Institute of Allergy and Infectious Diseases, National Institutes of Health grant R01 AI69568-01A2. Thus, the U.S. government has certain rights in this application." and insert therein -- This invention was made with government support under Grant Numbers AI015447 and AI069568 awarded by the National Institutes of Health. The government has certain rights in the invention. --.

Signed and Sealed this
Third Day of December, 2013

Margaret A. Focarino
*Commissioner for Patents of the United States Patent and Trademark Office*

UNITED STATES PATENT AND TRADEMARK OFFICE
CERTIFICATE OF CORRECTION

PATENT NO. : 8,541,006 B2  Page 1 of 1
APPLICATION NO. : 12/671398
DATED : September 24, 2013
INVENTOR(S) : Leid et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 368 days.

Signed and Sealed this

Fifteenth Day of September, 2015

Michelle K. Lee
*Director of the United States Patent and Trademark Office*